United States Patent
Korakianitis et al.

(10) Patent No.: US 6,632,169 B2
(45) Date of Patent: Oct. 14, 2003

(54) OPTIMIZED PULSATILE-FLOW VENTRICULAR-ASSIST DEVICE AND TOTAL ARTIFICIAL HEART

(75) Inventors: Theodosios Korakianitis, St. Louis, MO (US); Lonn Grandia, Brussels, IL (US)

(73) Assignee: LTK Enterprises, L.L.C., St. Louis, MO (US)

(*) Notice: Subject to any disclaimer, the term of this patent is extended or adjusted under 35 U.S.C. 154(b) by 298 days.

(21) Appl. No.: 09/805,523

(22) Filed: Mar. 13, 2001

(65) Prior Publication Data

US 2003/0032853 A1 Feb. 13, 2003

(51) Int. Cl.$^7$ ................................................. A61F 2/02
(52) U.S. Cl. ........................................................ 600/16
(58) Field of Search ........................ 600/16–18; 128/898

(56) References Cited

U.S. PATENT DOCUMENTS

| | | |
|---|---|---|
| 3,842,440 A | 10/1974 | Karlson |
| 3,911,898 A | 10/1975 | Leahman, Jr. |
| 4,102,610 A | 7/1978 | Taboada et al. |
| 4,210,409 A | 7/1980 | Child |
| 4,375,941 A | 3/1983 | Child |
| 4,541,787 A | 9/1985 | DeLong |
| 4,610,658 A | 9/1986 | Buchwald et al. |
| 4,888,011 A | 12/1989 | Kung et al. |
| 4,965,864 A | 10/1990 | Roth et al. |
| 5,089,017 A | 2/1992 | Young et al. |
| 5,676,162 A | 10/1997 | Larson, Jr. et al. |
| 5,676,651 A | 10/1997 | Larson, Jr. et al. |
| 5,693,091 A | 12/1997 | Larson, Jr. et al. |
| 5,702,430 A | 12/1997 | Larson, Jr. et al. |
| 5,722,429 A | 3/1998 | Larson, Jr. et al. |
| 5,722,930 A | 3/1998 | Larson, Jr. et al. |
| 5,758,666 A | 6/1998 | Larson, Jr. et al. |
| 5,843,129 A | 12/1998 | Larson, Jr. et al. |
| 5,879,375 A | 3/1999 | Larson, Jr. et al. |

OTHER PUBLICATIONS

Elias P. Gyftopoulos and Gian Paolo Beretta; Thermodynamics: Foundations and Applications; book; 1991; Macmillan Publishing Co.; U.S.

David Gordon Wilson; Theodosios Korakianitis; The Design of High–Efficiency Turbomachinery and Gas Turbines; book; 1998; $2^{nd}$ ed.; Prentice–Hall, Inc.; U.S.; 1984; MIT Press Simon & Schuster.

O. E. Balje; Turbomachiones; Publication; 1981; John Wiley & Sons, Inc.; U.S.; CA.

(List continued on next page.)

Primary Examiner—Jeffrey R. Jastrzab
(74) Attorney, Agent, or Firm—Blackwell Sanders Paper Martin LLP

(57) ABSTRACT

A method of optimizing a mechanical cardiac pumping device includes modeling the circulatory system of the patient who will receive the mechanical cardiac pumping device and identifying an operating condition of the native heart to which the device will respond. The model is used to determine the required blood volume to be ejected from the device and an initial estimate of the power required to be provided to the mechanical cardiac pumping device is provided in order to provide the required ejected blood volume. The resultant ejected blood volume is evaluated with data obtained from the model and the estimate of the power requirement is then updated. The above steps are iteratively performed until the power required to obtain the necessary ejected blood volume is identified. Possible variations of power and pumping rate that allow the mechanical cardiac pumping device to provide the required volume are determined and the variation that best matches the physiological constraints of the patient and minimizes the power required by the mechanical cardiac pumping device is selected. The steps are iteratively performed until the mechanical cardiac pumping device is optimized to respond to each desired operating condition of the native heart.

3 Claims, 22 Drawing Sheets

OTHER PUBLICATIONS

Barna Szabó and Ivo Babuŝka; Finite Element Analysis; book; 1991; John Wiley & Sons, Inc.

Eugene Braunwald, M.D.; Heart Disease; textbook; 1984; vol. 1; W. B. Saunders Co.; 1980; W. B. Saunders Co.; U.S.; CA.

Y. C. Fung; Biodynamics; book; 1984; Springer–Verlag; U.S.

Wilmer W. Nichols and Michael F. O'Rourke; McDonald's Blood Flow in Arteries; book; 1998; 4$^{th}$ Edition; Oxford University Press, Inc.; U.S.

Ronald L. Panton; Incompressible Flow; book; 1994; John Wiley & Sons, Inc.; U.S.

Frank M. White; Viscous Fluid Flow; book; 1991; 2$^{nd}$ ed.; 1974; McGraw–Hill, Inc.

Dr. Hermann Schlichting; Boundary–Layer Theory; book; 7$^{th}$ Edition; 1979, 1968, 1960, 1955; 7$^{th}$, 6$^{th}$, 4$^{th}$, 2$^{nd}$ eds.; McGraw–Hill Book Co.; US; AG; DE.

J. O. Hinze; Turbulence; book; 1975; 2$^{nd}$ ed.; 1959; McGraw–Hill Book Co., Inc.; U.S.

H. Power, Editor; Bio–Fluid Mechanics (M. Rahman, Series Editor: Advances in Fluid Mechanics); book; vol. 3; Computational Mechanics Publications; U.S.; CA; MX.

Altman, Lawrence K.;Self–Contained Mechanical Heart Throbs for First Time in a Human; Article; Jul. 4, 2001; Three (3) pages; The New York Times.

Altman, Lawrence K.; Artificial–Device Recipient Said to Make Excellent Progress; Article; Jul. 5, 2001; Four (4) pages; The New York Times; Internet.

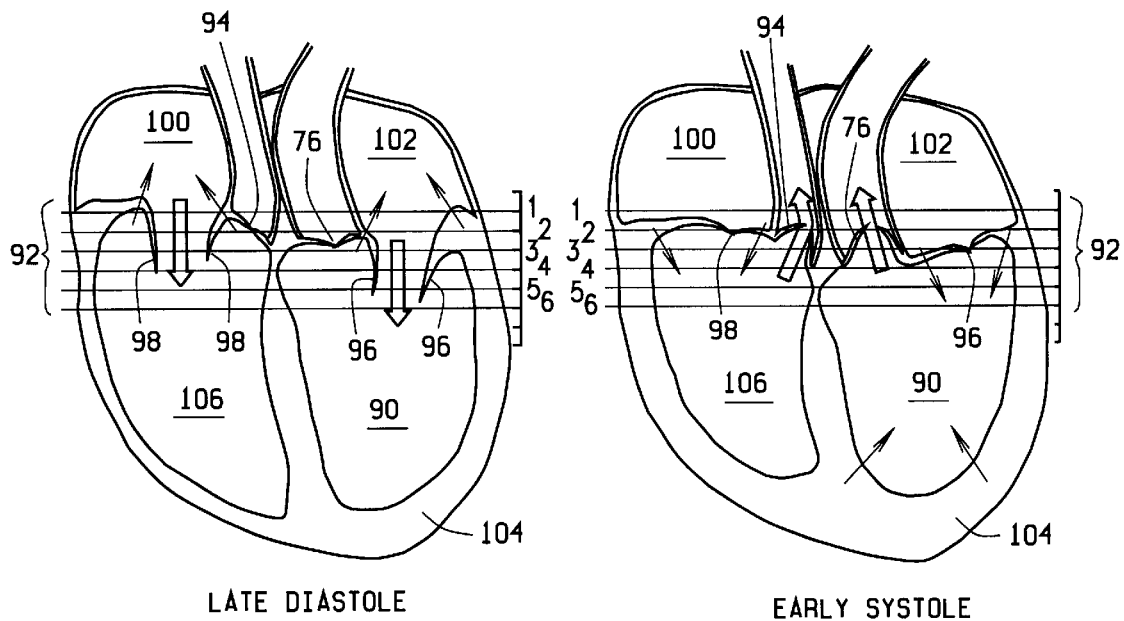
LATE DIASTOLE
FIG. 10
EARLY SYSTOLE
FIG. 11
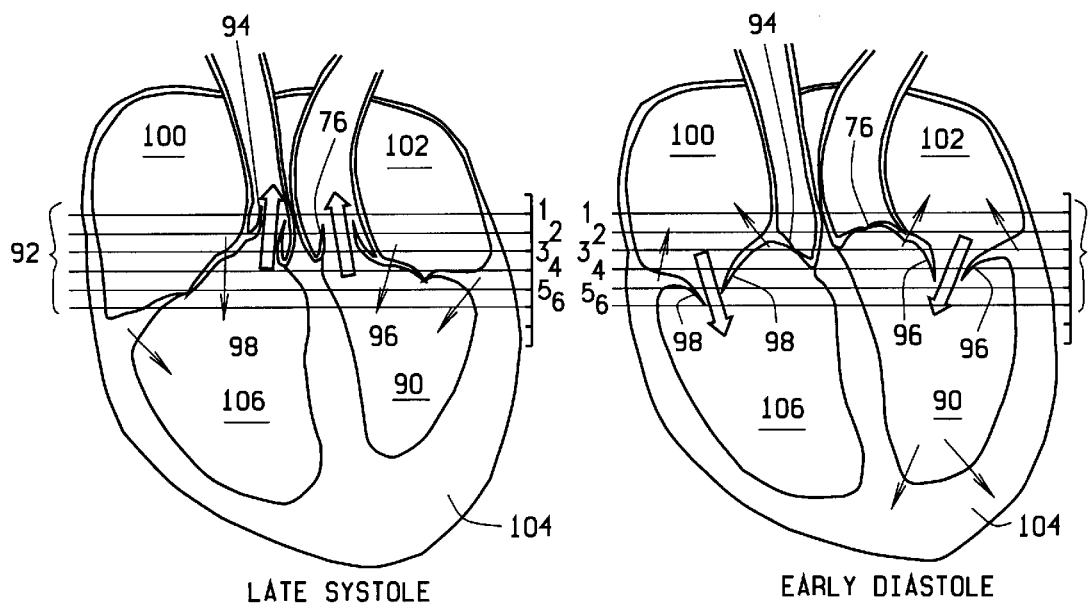
LATE SYSTOLE
FIG. 12
EARLY DIASTOLE
FIG. 13

OPTIMIZED PULSATILE-FLOW VENTRICULAR-ASSIST DEVICE AND TOTAL ARTIFICIAL HEART

BACKGROUND OF THE INVENTION

1. Field of the Invention

This invention relates generally to the field of mechanical cardiac pumping devices, and, more particularly, to a ventricular assist device (VAD) and a total artificial heart (TAH) device and method of using same. More specifically, this invention relates to a VAD and a TAH that are optimized by the new method to produce customized pulsatile blood flow mimicking that of the healthy native heart for each individual patient case.

2. Description of Related Art

Introduction:

Some medical studies indicate: a) 400,000 new cases of congestive heart failure are diagnosed annually in the United States; b) a mortality rate of 75 percent in men and 62 percent in women; c) standard medical therapies benefit only a limited percentage of patients with ventricular dysfunction; and d) from 17,000 to 66,000 patients per year, in the United States alone, may benefit from a permanent implantable blood pump. Presently, potential cardiac transplant recipients with hemodynamic compromise (inadequate perfusion of the systemic circulation by the native heart) sometimes receive temporary mechanical circulatory support as a "bridge" to permit them to survive until cardiac transplantation is possible. It is foreseen that some day mechanical blood pumps will provide a cost-effective alternative to either cardiac transplantation or long term medical management of patients. It is to this end that the devices and methods described herein have been developed.

It is to be understood that for purposes of this document a "ventricular-assist device (VAD)" is a mechanical blood pump that assists a diseased native heart to circulate blood in the body, and a "total artificial heart (TAH)" is another type of mechanical blood pump that replaces the native heart and provides all of the blood pumping action in the body.

In order for a VAD to function optimally, it must both complement the diseased native heart and make the combined output of the VAD and native diseased heart emulate the pumping action of the natural healthy human heart. That is, it should provide pulsatile flow similar to that of the healthy heart. In order for a TAH to function optimally, it must mimic the pulsatile pumping action of the natural healthy human heart. In either case, the device must be sized such that it fits within the required areas in the patient's body. In order to minimize the size of the power supply portion of the device, each device (VAD or TAH) must use as little energy and as little power as possible to accomplish the required function. Thus, there is a need for bio-emulating efficient pump (BEEP) systems for VAD and TAH applications.

It is known that VADs can be implanted to assist a functioning heart that does not have adequate pumping capability. Often, however, residual cardiac function is not taken into account in the design of such devices, resulting in less than optimal effects. What is needed is a bio-emulating efficient pump (BEEP) system, which works in concert with the native human heart. The new VAD device and system and optimization procedure described herein utilize patient specific information concerning residual cardiac output to optimize the pumping action provided for each individual patient, thereby providing such a BEEP system. The TAH device and optimization procedure described in this document optimize the pumping function provided for each individual patient, thereby providing such a BEEP system which is customized for each such patient. Known Heart Pump Devices:

Previously, a number of devices were developed for blood pumping. Highly specialized pumps have been used to completely replace a biological heart which has been surgically removed. Such known heart pumps may be temporary, or permanently implantable. Temporary heart pump devices usually involve either: 1) an attempt to augment a compromised native heart while it recovers from surgery or some other short-term problem; or 2) use of the device as a "bridge" to extend the life of a patient by temporarily replacing the native heart until a suitable donor heart can be found for cardiac transplantation.

Many types of permanently implantable heart pumps have been proposed and several have been developed. Because the left ventricle of the heart, which pumps blood to the entire body except for the lungs, becomes diseased far more commonly than the right ventricle (which pumps blood only to the lungs), most heart pumps have been developed to assist or replace the left ventricle. Fewer pumps have been proposed, tested, and used for bi-ventricular function (i.e. assisting both the left and right ventricles).

Known mechanical blood pumps can be roughly divided into three major categories: a. pulsatile sacks; b. reciprocating piston-type pumps; and c. pumps with axial or centrifugal impellers. Each category has distinct advantages and disadvantages.

a. Pulsatile Sacks

Pulsatile sack devices are the most widely tested and used implantable blood pumps. These devices employ flexible sacks or diaphragms which are compressed and released in a periodic manner to cause pulsatile flow of blood. Sack or diaphragm pumps are subject to fatigue failure of compliant elements. They are generally used as temporary heart-assist devices, and they are mechanically and functionally different from the present invention described hereafter.

The intra-aortic balloon (IAB) counter-pulsation device, a pulsatile sack device, is readily available. It is a catheter-mounted intra-vascular device designed to improve the balance between myocardial oxygen supply and demand. The first successful clinical application of the balloon was reported by Kantrowitz et al. in 1968. The IAB is positioned in the thoracic aorta and set to inflate at the dicrotic notch of the atrial pressure waveform when monitoring aortic pressure. The diastolic rise in aortic pressure augments coronary blood flow and myocardial oxygen supply. The IAB is deflated during the isovolumetric phase of left ventricular contraction. The reduction in the afterload component of cardiac work decreases peak left ventricular pressure and myocardial oxygen consumption. These units are not portable and are limited to in-hospital critical care use only. Use of the IAB is now a standard form of therapy for a variety of patients with cardiovascular disease, primarily reserved for patients with deteriorating heart function while awaiting revascularization procedure. In 1993, nearly 100,000 IABs were inserted in the United States alone.

Another example of a pulsatile sack device is the Abiomed™ BVS® device (Abiomed, Inc., Boston, Mass.). It is an externally placed dual-chamber device that is capable of providing short term univentricular or biventricular support. It has pneumatically driven polyurethane blood sacks and it is not intended for long-term support. Also, U.S. Pat. No. 4,888,011 to Kung and Singh discloses a hydraulically driven dual-sack system; and U.S. Pat. No. 5,743,845 to Runge discloses a sack-operated bi-ventricular assist device that balances the flow in the left and right side of the circulatory system.

b. Reciprocating Piston-Type Pumps

Several types of implantable blood pumps containing a piston-like member have been proposed to provide a mechanical device for augmenting or totally replacing the blood pumping action of a damaged or diseased heart. For example, the HeartMate® (Thermo Cardiosystems, Inc., Woburn, Mass.) is a pneumatically powered device that is implanted in the left upper quadrant of the abdomen. A pneumatic air hose exits from the lower half of the abdominal wall and is attached to a pneumatic power unit. Blood from the cannulated left ventricular apex empties into a pump, at which point an external control system triggers pumping. The blood chamber is pressurized by a pusher plate forcing a flexible plastic diaphragm upward. This motion propels the blood through an outflow conduit grafted into the aorta, the main artery supplying the body with blood. This device is unique in that the textured, blood-containing surface promotes the formation of a stable neointima, hence full anticoagulation is not necessary, only anti-platelet agents are required. This device is designed for left ventricular support only. It uses trileaflet polyurethane valves. There is an electrically powered version with percutaneous electric leads connecting the pump to external batteries.

The Thoratec® VAD (Thoratec Laboratories, Pleasanton, Calif.) is a pneumatically powered device that is placed externally on the anterior abdominal wall. Cannulas pass through the chest wall in a manner similar to that of a conventional chest tube. The device takes blood from the left ventricular apex and returns it to the aorta. Full systemic anticoagulation is required with this device. It can be used to support either ventricle and uses tilting disc type mechanical valves.

Novacor® (Cedex, France) produces an electrically driven device that is implanted in the left upper quadrant of the abdomen and the electric line and vent tube are passed through the lower anterior abdominal wall. This system also incorporates a polyurethane blood sac that is compressed by dual symmetrically opposed pusher plates. Blood is taken from the left ventricular apex and returned to the aorta. Full anticoagulation is required.

U.S. Pat. No. 3,842,440 to Karlson discloses an implantable linear motor prosthetic heart and control system containing a pump with a piston-like member which reciprocates in a magnetic field. The piston includes a compressible chamber in the prosthetic heart which communicates with the vein or aorta.

U.S. Pat. Nos. 3,911,897 and 3,911,898 to Leachman, Jr. disclose heart assist devices controlled in the normal mode of operation to copulsate and counterpulsate with the heart, respectively, and produce a blood flow waveform corresponding to the blood flow waveform of the assisted heart. The heart assist device is a pump connected serially between the discharge of a heart ventricle and the vascular system. This pump has cylindrical inlet and discharge pumping chambers of the same diameter and a reciprocating piston in one chamber fixedly connected with a reciprocating piston of the other chamber.

U.S. Pat. No. 4,102,610 to Taboada et al. discloses a magnetically operated constant volume reciprocating pump which can be used as a surgically implantable heart pump or assist. The reciprocating member is a piston carrying a check valve positioned in a cylinder.

U.S. Pat. Nos. 4,210,409 and 4,375,941 to Child disclose a pump used to assist the pumping action of the heart with a piston movable in a cylindrical casing in response to magnetic forces. A tilting-disk type check valve carried by the piston provides for flow of fluid into the cylindrical casing and restricts reverse flow.

U.S. Pat. No. 4,965,864 to Roth discloses a linear motor using multiple coils and a reciprocating element containing permanent magnets, driven by microprocessor-controlled power semiconductors. A plurality of permanent magnets is mounted on the reciprocating member. U.S. Pat. No. 4,541,787 to DeLong describes a pump configuration wherein a piston containing a permanent magnet is driven in a reciprocating fashion along the length of a cylinder by energizing a sequence of coils positioned around the outside of the cylinder.

U.S. Pat. No. 4,610,658 to Buchwald et al. discloses an implantable fluid displacement peritoneovenous shunt system. The device is a magnetically driven pump, which can be a reciprocating diaphragm, or piston type, or rotary pump.

U.S. Pat. No. 5,089,017 to Young et al. discloses a drive system for artificial hearts and left ventricular assist devices comprising one or more implantable pumps driven by external electromagnets. The pump utilizes working fluid, such as sulfur hexafluoride to apply pneumatic pressure to increase blood pressure and flow rate.

Larson et al. in a series of patents (1997–1999, U.S. Pat. Nos. 5,879,375; 5,843,129; 5,758,666; 5,722,930; 5,722,429; 5,702,430; 5,693,091; 5,676,651; 5,676,162) describe a piston-type pump for ventricular assist or total replacement, and associated driving equipment and power supply. The piston is an artificial heart valve, with valves that have at least two leaflets, acting as a check valve and reciprocating in a cylinder. The walls of the cylinder are a few millimeters thick because they contain the coils of a linear electric motor that must provide pumping power to the VAD. Around the artificial heart valve and inside the cylinder is a hollow cylindrical rare-earth permanent magnet, which is driven by the linear electric motor. In one embodiment one device is implanted in series to the aorta (left VAD), or another device is implanted in series to the pulmonary artery (right VAD), or two devices are used on both aorta and pulmonary artery (BI-VAD). In a second embodiment one device replaces the left ventricle, or another device replaces the right ventricle, or two devices replace the whole heart.

Measurements on experimental devices made with hollow pump cores indicate that such devices are too large to fit in the available space in the chest cavity in the aorta or pulmonary artery, due to the size of the coils necessary to drive the device. For a given volume of blood pumped per stroke, if the length of the cylinder is restricted such that the device fits lengthwise in the human body, then the diameter must be increased until the desired volume is reached. The outer diameter of the device is severely restricted by the surrounding tissue, and this leaves little room available in the diameter for the linear magnet motor. In a bi-ventricular application, if the axes of the two cylinders are located in parallel, then even more space is needed due to the diameters required; and if they are not parallel the magnetic fields of the two motors introduce additional electromagnetic losses because the linear magnet motors are not parallel. Even if the volumetric displacement of the device is reduced in order to fit in the available space at the expense of throughput, much of the outside diameter of the device must still be devoted to the linear motor. However, the most important disadvantage is that the linear motor is driving an annular magnet containing a one-way valve, so that the ferromagnetic material can not be in the core (center) of the motor coils, leading to lower efficiency.

At the geometric center (axis) of the motor described by Larson et al. is the artificial valve acting as the piston, and the blood itself. This structure introduces electromagnetic losses in the device that make it less desirable than devices that have ferromagnetic material in the geometric center (axis) of the motor coils. In addition, voltage propagates at constant velocity from coil to coil in the linear magnet motor of the Larson et al. device, and motion of the magnet carrying the artificial heart valve is coupled to this application of voltage, so that the application of current in the Larson et al. device is not optimized to minimize the power required to effect the blood-pumping action.

c. Pumps with Axial or Centrifugal Impellers

After pulsatile devices, rotary pumps, having either centrifugal or axial impellers, are the most widely used and tested devices. In centrifugal pumps, the blood flow enters axially into a centrifugal impeller, centrifugal acceleration increases the blood flow velocity, the flow exits radially, and the flow is subsequently decelerated to increase blood static pressure in the diffusion process. Most such centrifugal pumps provide continuous (non-pulsatile) flow; or flow with a small fluctuating pressure trace superimposed on a larger steady-pressure component, such as U.S. Pat. No. 5,928,131 to Prem and U.S. Pat. No. 6,179,773 to Prem and Kolenik.

Axial pumps direct blood flow along a cylindrical axis, which is in a straight (or nearly straight) line with the direction of the inflow and outflow. The impeller looks like an axial fan, or propeller, inside a nozzle. The impeller imparts acceleration to the fluid, and the subsequent deceleration (diffusion) process increases the blood pressure. Most such axial pumps provide continuous (non-pulsatile) flow.

Some types of axial rotary pumps use impeller blades mounted on a center axle, which is mounted inside a tubular conduit. As the blade assembly spins, it functions like a fan or an outboard motor propeller. Another type of axial blood pump, called the "haemopump" uses a screw-type impeller with a classic screw (also called an Archimedes screw; also called a helifoil, due to its helical shape and thin cross-section). In screw-type axial pumps, the screw spins at very high speed (up to about 10,000 rpm). The entire haemopump unit is usually less than one centimeter (approximately 0.4 inches) in diameter. The pump can be passed through a peripheral artery into the aorta, through the aortic valve, and into the left ventricle. An external motor and drive unit powers it.

Axial and centrifugal pumps provide mostly steady (continuous) flow with an imperceptible high-frequency low-amplitude pulsatile component. Various mechanisms have been proposed to convert this practically steady-flow output into pulsatile flow. However, both axial and centrifugal impeller pumps introduce rapid acceleration and deceleration forces and large shear stresses in the blood. As is well known to those with ordinary skill in the art (Balje, 1981), both types of turbomachines (axial and centrifugal) are a balanced compromise between diameter and speed to provide the specified flow rate and pressure increase. Imposing limits in diameter in order to reduce shear stresses means that the optimum machine requires a higher-speed axial component. Imposing speed limits in order to reduce shear stresses means that the optimum machine requires a higher-diameter centrifugal component. It is well know to those with ordinary skill in the art (Wilson and Korakianitis, 1998) that small impellers that can fit inside the spaces available in the human body will result in high blood shear, due to the high operational speed required.

The Jarvik 2000® (registered trademark of R. Jarvik, New York, N.Y.) System consists of a small axial flow pump (about the size of a C-cell battery) that is placed in the left ventricular apex and pumps blood into the aorta. It is still currently being developed and will use external batteries and control electronics utilizing induction coils to carry the control signals through the skin. Power is also delivered transcutaneously.

Medical Complications:

According to several medical studies, the above devices are subject to a number of complications. Insertion of a cannula to feed a pump can cause damage to the left ventricle. At least 50 percent of patients who are supported for prolonged periods develop infections, including those associated with pneumatic lines or electrical leads. Septic emboli may occur, and the mortality rate is up to 50 percent. VADs may also activate the coagulation cascade, resulting in thrombi formation. This occurs in the approximate range of nine to forty-four percent of patients. Stasis of blood within the pump may lead to thrombus deposition. Right ventricular failure may occur peri-operatively with placement of a left VAD. The right heart failure rate may be as high as 33 percent, with one-fifth of those patients dying from the complication. Rapid recognition of this complication and implantation of a right VAD may reduce the mortality rate resulting from right heart failure. Hemorrhage occurs in about 27 to 87 percent of patients who require mechanical ventricular assistance. Hemorrhage is also related to inflow and outflow cannulae and to anticoagulation required with the devices.

One of the most important problems in axial and centrifugal rotary pumps involves the interface between the edges of the blades and the blood flow. The outer edges of the blades move at high speeds and generate high levels of shear. Red blood cells are particularly susceptible to shear stress damage, as their cell membranes do not include a reinforcing cytoskeleton to maintain cell shape. Lysis of red blood cells can result in the release of cell contents and trigger subsequent platelet aggregation. Lysis of white blood cells and platelets also occurs upon application of high shear stress. Even sublytic shear stress leads to cellular alterations and direct activation and aggregation of platelets. Rotary pumps generally are not well tolerated by patients for prolonged periods. In medical tests, animals placed on these units for a substantial length of time often suffer from strokes, renal failure, and other organ dysfunction.

The device and method of optimization disclosed herein minimizes the above, and other, known complications resulting from implantation of either a VAD or a TAH.

Desirable Pump Characteristics:

In many patients with end stage heart disease, there is enough residual function left in the native heart to sustain life in a sedentary fashion, but insufficient reserve for even minimal activity, such as walking a short distance. This residual function of the diseased native heart is typically not considered in the design of most VADs. Most known VADs are designed to assume complete circulatory responsibility and to receive blood from the cannulated ventricular apex of the particular ventricle they are "assisting," in what is commonly called "fill to empty" mode. It generally takes one or more contractions of the diseased native ventricle to supply enough blood to the VAD. Once a pre-specified volume of blood is accumulated in the VAD, then the ejection phase of the VAD is initiated. Thus, most known VADs operate in this "fill-to-empty" mode that is in random association with native heart contraction, and can be installed in parallel to the native ventricle or in series. These constructions are not considered to "complement" the native heart, as does the present invention.

At least some residual cardiac function is present in the majority of patients who would be candidates for mechanical circulatory assistance. It is preferable for the natural heart to continue contributing to the cardiac output even after a mechanical circulatory device is installed. This points away from the use of total cardiac replacements and suggests the use of assist devices whenever possible. However, the use of assist devices also poses a very difficult problem. In patients suffering from severe heart disease, temporary or intermittent crises often require artificial pumps to provide bridging support which is sufficient to entirely replace ventricular pumping capacity for limited periods of time. Such requirements arise in the hours or days following a heart attack or cardiac arrest, or during periods of certain life threatening arrhythmias. Therefore, there is an important need to provide a pump and method that can meet a wide spectrum of requirements by providing two different and distinct pumping functions, assisting the native heart and total substitute pump support.

SUMMARY OF THE INVENTION

The present invention provides a cardiac ventricular-assist device and method of optimizing any design of VAD or TAH wherein the amount of power required by the device is minimized to the extent necessary to complement the cardiac output of the native heart, and no more. In this manner, the weight and size of the device are kept within suitable reasonable ranges to permit placement of the VAD/TAH within the body of the subject patient using the new device.

The present invention further provides a VAD and method wherein the principles of unsteady thermodynamics and fluid mechanics are used to provide a uniquely optimized pulsatile blood flow which complements the cardiac output of the individual native human heart. It is to be understood that throughout this document, when the terms "optimize" and "complement" are used in reference to the devices and systems of the present invention, it is meant that at each heart beat and stroke of the VAD (used here to mean either the L-VAD, R-VAD, BI-VAD or TAH as described below), several actions are carefully timed such that:

a) the native heart is allowed to pump as much blood as it can on its own before the VAD is activated;
  b) as the blood-ejection phase of the native heart nears completion, the VAD is energized to provide additional pumping action;
  c) the additional pumping action reduces the back pressure in that native ventricle so that the native ventricle pumps more than it would have pumped unaided;
  d) the timing of the action, length of pumping stroke, and rate of pumping (stroke displacement versus time and resulting power input versus time) of the VAD are related to the native heart ejected blood volume and rhythm in a manner that minimizes power input to the VAD while meeting physiological constraints;
  e) the optimization processes in d) take into account the dynamic interaction between the native heart and the VAD; and
  f) the optimization process and the control scheme are integrated with the resulting changes in blood ejected per heart beat and heart rate (beats per minute) by the combined action of the native heart and the VAD.

Before turning to the Figures, it is considered useful to provide some introductory material. The present invention, described below, is distinct from each of the three categories of mechanical circulatory support devices previously described, and consolidates the advantages and avoids the disadvantages of each category. First, it is carefully noted that several of the devices described in the known art mention that the power input is "optimized", but they do not describe how this is accomplished. The optimization method described herein can be applied to all existing VAD and TAH devise that have been devised to date, or will be devised in the future.

The pump of the present invention has ferromagnetic material as the solid center of the motor coils, thus providing a more compact arrangement of the electromagnetic fluxes than pumps with non-ferromagnetic centers, and simultaneously permitting reduction of electromagnetic losses in use. Ultimately this permits placement of a device that can pump sufficient volume per stroke at the outlet of the native ventricles and allows the power supply to be smaller than was possible with previous cardiac pumping devices. The remote hydraulic drive and power supply/controller assembly are located in the abdomen, thus allowing practically all available space in the vicinity of the heart for use by the device. Power is transmitted hydraulically from the abdomen to the blood pump in the vicinity of the heart. Also, electromagnetic losses are not introduced by the location of the two pumping devices (artificial heart valves) in non-parallel configuration in the vicinity of the aorta and pulmonary artery.

Details of the dynamics of the pumping action of the human heart have been incorporated for the first time into the design of the VADs and TAHs in the present invention. Understanding these details:

1) is essential for optimization of the timing of unsteady-flow events in the heart-pumping cycle;
  2) directly impacts the optimum geometric shape of the artificial devices; and
  3) identifies prerequisite means to minimize shear stresses on the blood (reducing blood-cell lysis) and optimizing energy flows (reducing the power input required to produce the required blood flow and pressure characteristics).

The adult heart is located between the lungs and is about the size of a large grapefruit, weighing 0.2 to 0.5 kg (0.44 to 1.1 pounds), depending on the size of the individual. The cardiovascular system performs two major tasks: it delivers oxygen and nutrients to body organs; and removes waste products of metabolism from tissue cells. Its major components are: the heart (a two-sided biological pump); and the circulatory system of elastic blood vessels (veins and arteries) that transport blood. As an example, the heart of a 70 kg (154 pounds) human circulates about 6 kg (13.2 pounds), or 6 L (6.34 qt.s), of blood.

The human heart is divided into four chambers: the right atrium and right ventricle; and the left atrium and left ventricle. The walls of the chambers are made of a special muscle called the myocardium that contracts rhythmically under electric stimulation. The left and right atria are separated from each other by the atrial septum; and the left and right ventricles are separated from each other by the ventricular septum.

In the circulatory system, blood returns by the venous system from the body and enters the heart through the right atrium, then subsequently blood enters the right ventricle. Each time the right ventricle contracts, it propels this blood (low in oxygen content) into the lungs, where it is enriched with oxygen. Pulmonary veins return the blood to the left atrium, then subsequently the blood enters the left ventricle. The left ventricle, which traditionally has been considered as the main pumping instrument of the heart, ejects the blood through the main artery, the aorta, to supply oxygenated blood to the various organs of the body. The organs use the oxygen and with capillary action between the arterioles and the venules return the blood to the venous system and the right atrium. The pumping action of the left and right side of the heart generates pulsatile flow and pressure on the aorta and pulmonary artery, discussed further below.

Blood is kept flowing in this pulsatile cycle by a system of four one-way valves in the heart, each closing an inlet or outlet in one of the heart's four chambers at the appropriate time in the cardiac cycle. The valve system helps maintain a pressure difference between the right and left sides of the heart. The aortic valve and the pulmonary valve each have three tissue cusps (leaflet flaps), referred to as "semilunar valves" because of the crescent shape of these cusps. The tricuspid and mitral valves separate the atria from the ventricles. The mitral valve has two cusps and the tricuspid valve has three cusps. In addition, the cusps have thin chords of fibrous tissue (chordae tendineae), which tether the valves to the ventricular walls. When the ventricles contract, small muscles in their walls (papillary muscles) restrict closure of the mitral and tricuspid valve leaflets, preventing them from overextending.

Electric currents control the pumping motion of the heart. The currents originate in the sinus node (the heart's natural pacemaker), a microscopic bundle of specialized cells located in the superior portion of the atria. The currents travel through a network of conducting fibers to the atrioventricular or AV node, the bundle of His, and the Purkinje fibers. The electric currents cause impulses that are transmitted and propagate in a wave fashion through the muscle fibers of the left and right atria to the atrioventricular node, located on the juncture between the right and left sides of the heart where the right atrium and right ventricle meet. From the atrioventricular node, they travel along the bundle of His and the Purkinje fibers through the muscles of the right and left ventricles. Most currents in the heart are less than a millionth of an Ampere, but they exert a powerful influence on the heart muscle.

The new VAD utilizes electromagnetic coils to drive a high-ferromagnetic-constant driving magnet in a reciprocating fashion so as to act as a piston for hydraulic fluid. The resultant movement of hydraulic fluid through the system in turn moves another magnet, which is annular, and which also drives in a reciprocating fashion. The movement of the driven annular magnet in turn moves still another magnet, an annular valve seat magnet, which supports a one-way valve. This valve seat magnet is located inside the annular driven magnet, the two magnets sharing a common center axis, hence coupling them together. The one-way valve pushes blood through the ascending aorta of the heart when the valve is pushed forward, and allows blood to flow freely past when the one-way valve is moved backward.

The present invention provides a ventricular-assist device and method for optimizing same that can be utilized to assist either the left ventricle (L-VAD) or right ventricle (R-VAD) of the native human heart or, if necessary, to assist both cardiac ventricles (BI-VAD). The L-VAD, R-VAD and BI-VAD devices all utilize principles of unsteady fluid mechanics to provide a uniquely individualized optimized pulsatile blood flow for each particular patient.

In an alternative embodiment, a total artificial heart (TAH) device that utilizes the principles of unsteady fluid mechanics provides a uniquely individualized optimized pulsatile blood flow for each particular patient. The optimized pulsatile blood flow mimics that of the native heart while simultaneously minimizing the power required to drive the TAH device.

Accordingly, it is among the goals of the present invention to provide a cardiac pump (VAD or TAH) device and system, and method for controlling and operating same which permit customized, optimized "assist" or "total" ("complete") cardiac pumping support for an indefinite period of time. Under appropriate conditions, the new VAD acts synergistically with the native heart to provide a seamless augmentation to the otherwise suboptimal output of the diseased native heart. This allows the new pump device (VAD) to take advantage of the natural, non-hemolytic pumping action of the native heart to the fullest extent possible to minimize red blood cell lysis, and to reduce mechanical stress on the VAD system pump, requiring less volume, less energy, and hence allowing longer pump life and longer battery life.

Accordingly, in furtherance of the above objects and goods, the present invention is, briefly, a method of optimizing a mechanical cardiac pumping device includes modeling the physical system, or portions thereof, of the patient who will receive the mechanical cardiac pumping device and identifying an operating condition of the native heart to which the device will respond. The model is used to determine the required blood volume to be ejected from the device and an initial estimate of the power required to be provided to the mechanical cardiac pumping device is provided in order to provide the required ejected blood volume. The resultant ejected blood volume is evaluated with data obtained from the model and the estimate of the power requirement is then updated. The above steps are iteratively performed until the power required to obtain the necessary ejected blood volume is identified. Possible variations of power and pumping rate that allow the mechanical cardiac pumping device to provide the required volume are determined and the variation that best matches the physiological constraints of the patient and minimizes the power required by the mechanical cardiac pumping device is selected. The steps are iteratively performed until the mechanical cardiac pumping device is optimized to respond to each desired operating condition of the native heart.

The mechanical system for accomplishing the new method is, briefly, a system for assisting cardiac ventricular function, the system including a hydraulic pumping assembly and a cardiac ventricular assist device (VAD) in fluid communication with the hydraulic pumping assembly, wherein the hydraulic pumping assembly includes an encapsulated hydraulic pump having a pumping chamber for retaining hydraulic fluid therein. The pumping chamber has opposed first and second ends and at least one electromagnetic coil surrounding the pumping chamber. A substantially solid high ferromagnetic-constant magnet is disposed longitudinally, slideably and reciprocally within the pumping chamber to act as a piston for driving hydraulic fluid within the pumping chamber in response to signals from a battery/controller assembly. A fluid line has a first end and a second end. The first end of the fluid line is connected to and in fluid communication with the first end of the pumping chamber and the second end of the fluid line is connected to and in fluid communication with the second end of the pumping chamber. The VAD is in fluid communication with the fluid line at a point on the fluid line after the point of connection of the check valve and before the connection of the second end of the fluid line and the second end pump chamber. A battery/controller assembly is operatively connected to the check valve and to the at least one electromagnetic coil to provide electric power and control signals to the pump. The battery controller assembly is in electrical communication with the native heart of the patient using the system, to thereby receive signals corresponding to physiological parameters from the native heart for transfer to the VAD.

The new VAD device is, briefly, a device to assist the function of a cardiac ventricle, the device having a first magnet with an open center and formed of high ferromagnetic-constant material. A first vessel of the device surrounds the first magnet and defines a space in fluid communication with the blood flow output great vessel associated with the diseased ventricle of a patient using the device, the first magnet being movable within the first vessel in substantially fluid-tight relation thereto. A second magnet is formed of high ferromagnetic-constant material in magnetic communication with the first magnet, so that the magnetic fluxes of the first magnet and the second magnet affect each other, so that the first magnet and the second magnet are biased toward and tend to lock to one another, to thereby move in the same direction as one another. A second vessel encases the second magnet and defines a space and is movable within the space in substantially fluid-tight relation to the second vessel, the space being defined by the second vessel being in fluid communication with a hydraulic pump for actuation the second magnet. A one-way valve is connected to the first magnet, the one-way vale being movable with the first magnet, and adapted to cause movement of blood from the diseased ventricle to and into the great vessel associated with the diseased ventricle.

These and other advantageous features of the present invention will be in part apparent and in part pointed out herein below.

BRIEF DESCRIPTION OF THE DRAWINGS

FIG. 10 is a concept illustration of the human heart illustrating the KG diaphragm in late diastole.

FIG. 11 is a concept illustration of the human heart illustrating the KG diaphragm in early systole.

FIG. 12 is a concept illustration of the human heart illustrating the KG diaphragm in late systole.

FIG. 13 is a concept illustration of the human heart illustrating the KG diaphragm in early diastole.

DETAILED DESCRIPTION OF THE INVENTION

FIGS. 1 through 4 are schematic illustrations of the BEEP system of the present invention, and the structural elements thereof. For the convenience of the reader, the unique power-optimizing and controller-optimizing methods, which are major aspects of the invention, and they are incorporated in the new BEEP system, are illustrated schematically by flow charts in FIGS. 28–34, to be described further, later herein.

Figure 1:
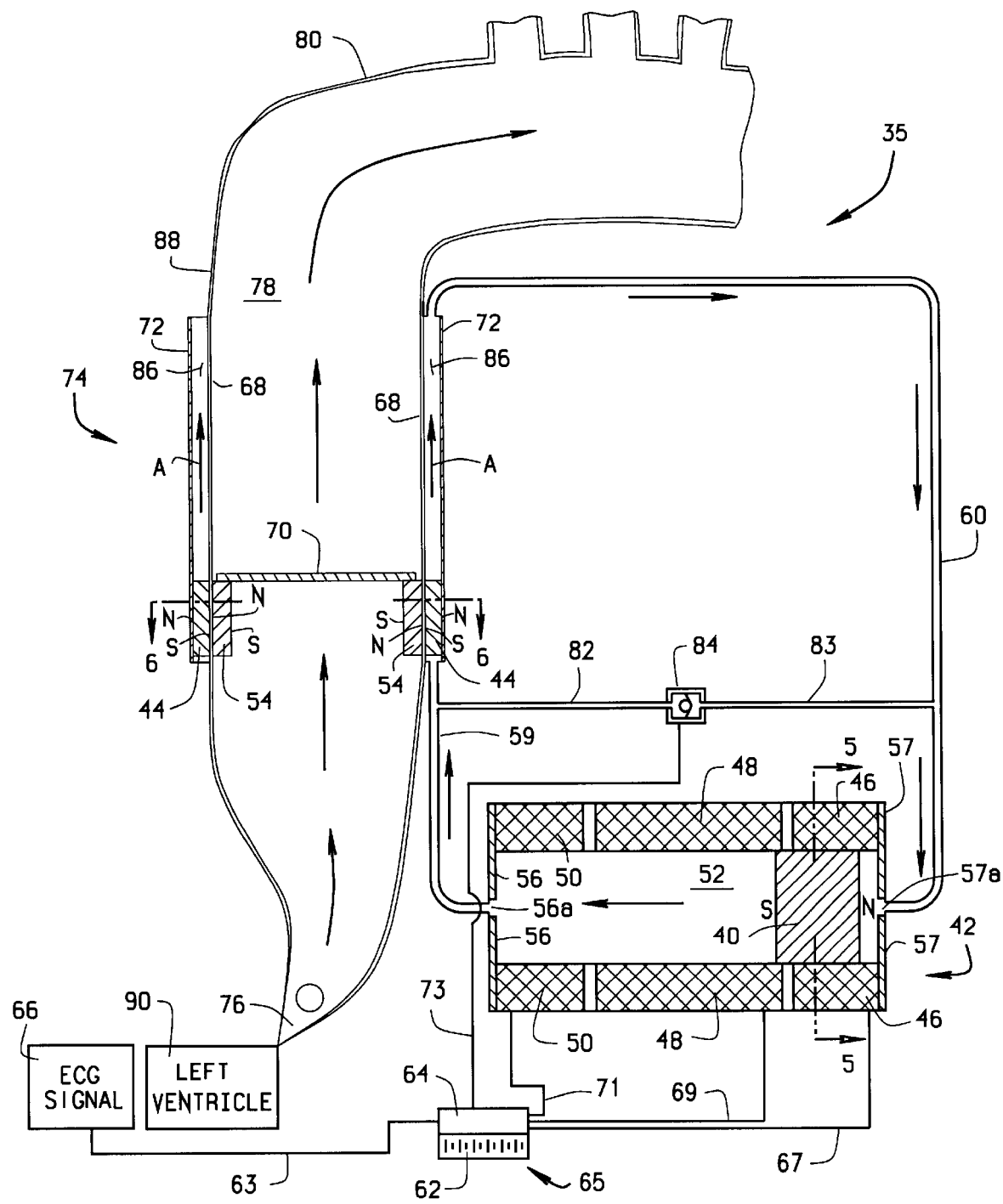
FIG. 1 is a schematic view generally identifying a bio-emulating efficient pump (BEEP) system. The Figure specifically illustrates the left ventricular-assist device (L-VAD) embodiment of a BEEP system at the beginning of the blood-pumping stroke.

The elements of the new BEEP system, as shown in FIG. 1, for example, and generally designated 35, compose three primary components: a ventricular assist device (VAD), which in this embodiment is an L-VAD, generally designated 74 (shown on the left side of FIG. 1). L-VAD 74 is actuated by a hydraulic pump, generally designated 42, and controlled by a battery/controller assembly, generally designated 65. It is to be understood that the new BEEP system 35 will be referred to throughout this document by the same reference numeral, in relation to a variety of embodiments. Thus, BEEP system 35 may include a L-VAD, R-VAD, BI-VAD, or TAH, all of which are described further herein, or the system may include alternative embodiments of any of the VADs or the TAH described below. The BEEP system is only a vehicle for the other aspects of the invention, the optimization process described in FIGS. 28–34. The optimization process can be applied to any current or future apparatus design of L-VAD, R-VAD, BI-VAD or TAH. The BEEP system per se, however, is nonetheless considered to be another important aspect of the invention, regardless of which embodiments of the various components are included in the system. Further in regard to the various embodiments of the system, if certain aspects of the overall system are not described in detail as being different or distinguishable from the other embodiments, they are considered to be the same or equivalent to those previously or later described.

BEEP system 35 utilizes electromagnetic coils 46, 48, and 50 to drive a high ferromagnetic-constant solid cylindrical driving magnet 40 in reciprocating fashion along the length of hydraulic pump 42. While three such coils are preferred, it is to be understood that the new system 35 and the alternative embodiments thereof can operate adequately with more than or fewer than three electromagnetic coils on pump 42. Driving magnet 40 is acting as a piston in a hydraulic pump. The interior vessel of the hydraulic pump may or may not incorporate end caps 56 and 57 as part of its hydraulic-vessel design. However, the presence of the end caps made of ferromagnetic material assist in directing the flux lines from the surrounding coils to the driving magnet 40. It will be obvious to those skilled in the art that several alternative embodiments can be contemplated by changing the cross sectional areas of the components, which may be circular, rectangular, or a number of other closed shapes.

Figure 5:
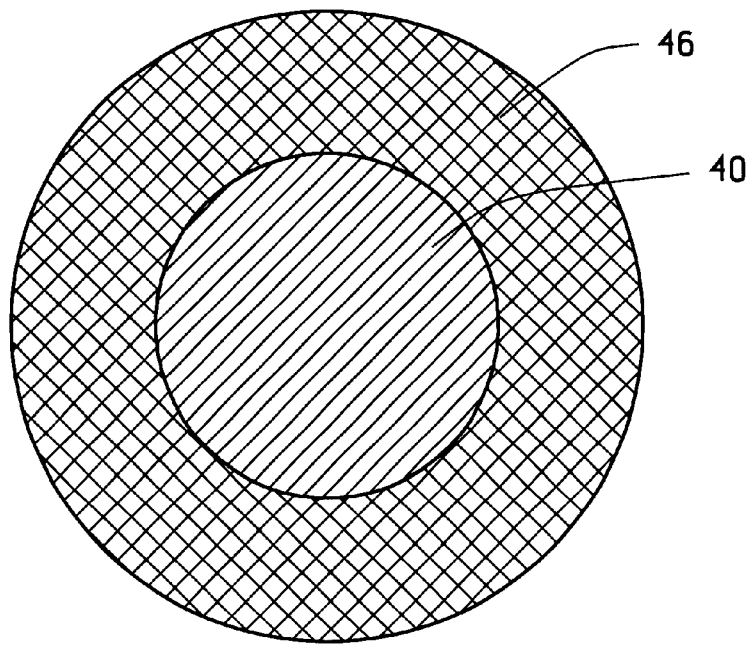
FIG. 5 is a cross-sectional view of the hydraulic pump of the BEEP system of FIG. 1, along line 5—5.

FIG. 5 shows pump 42 in cross section and illustrates the external cylindrical surface of driving magnet 40 mating with the interior cylindrical surface of electromagnetic coils 46, 48, and 50. These surfaces, whether shaped as the preferred cylinders, or otherwise, are nevertheless sized and shaped to slidingly interact as well as to minimize leakage of hydraulic fluid therebetween. It is understood that the function of pump 42 is to use one or more electromagnetic coils to drive one or more magnets in a way to provide motion to driven magnet 44; and several alternative embodiments can be used to accomplish this function. It will be obvious to those with ordinary skill in the art that there can be many variations on the cross-sectional view of the components, on the exact orientation of the electromagnetic fields, on the exact orientation of the magnets, on the type of hydraulic or pneumatic fluid, and on the details of the design of the vessel containing the hydraulic or pneumatic fluid etc, and these alternative embodiments are herein included. It is understood that several alternative embodiments to minimize leakage from the high to the low pressure of the hydraulic fluid and blood, and alternative embodiments to minimize friction between sliding components, are conceived and considered acceptable alternative designs in the present invention.

End caps 56, 57 are also made of ferromagnetic material, and are disposed on opposite ends of pump 42. End caps 56, 57 are provided with central openings 56a, 57a, so that the interior space defined by the electromagnetic coils is in fluid communication with main hydraulic line 60 at each end of the pump cylinder, permitting the hydraulic fluid to flow in and out of the pump cylinder, as described further hereafter.

Figure 19:
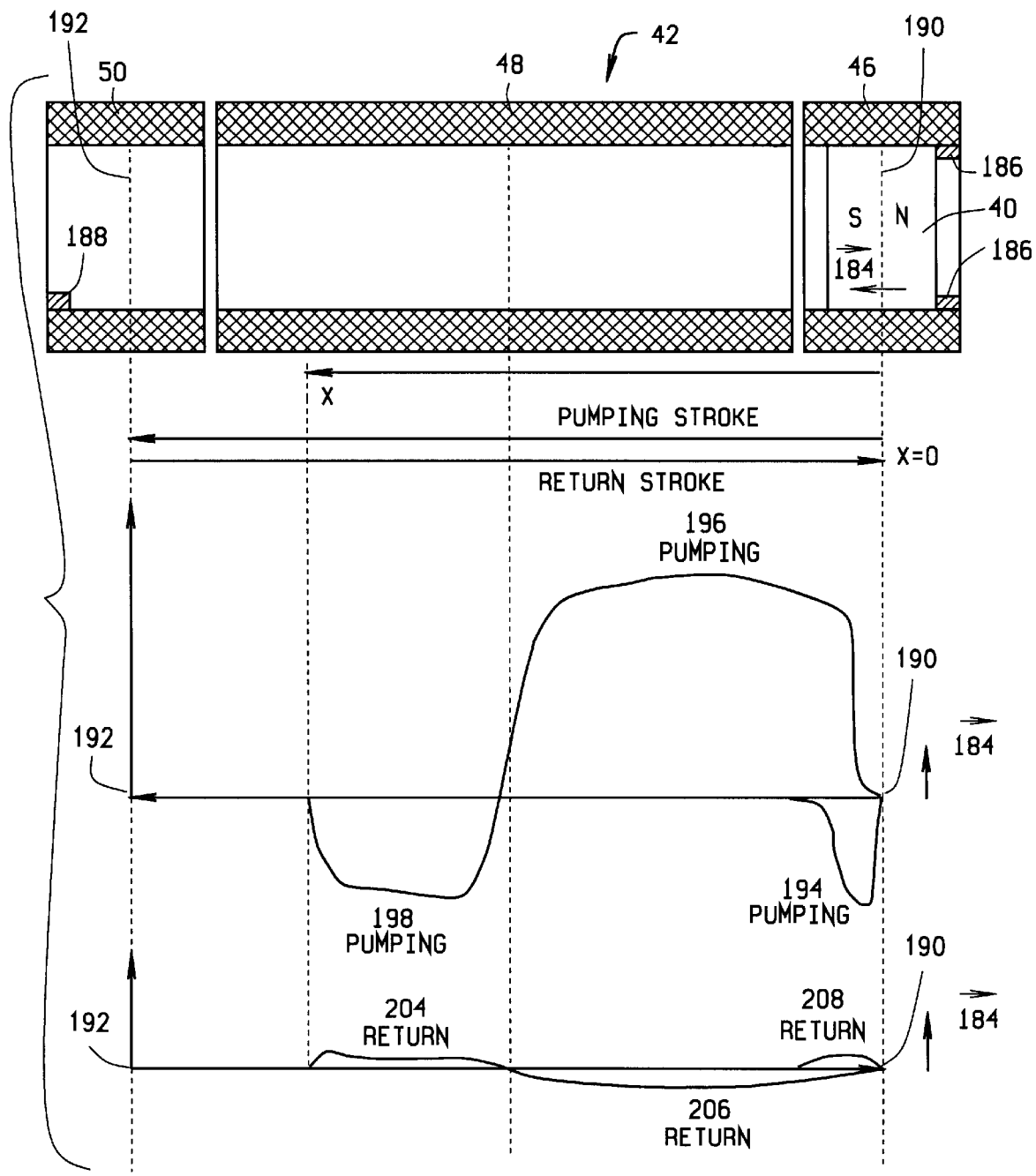
FIG. 19 illustrates the location of three electromagnetic coils in one embodiment of the BEEP system and the corresponding current flow sequence in the coils when only two of the coils are used to move the piston.

End caps 56, 57 also serve to concentrate the magnetic flux of electromagnetic coils 46, 48 and 50 in a smaller combined area, thereby improving pump efficiency. The shape of end caps 56 and 57 assists in the optimal placement and concentration of magnetic flux lines and minimization of the weight and dimensions of system components. While end caps 56, 57 act as "stops" for the piston, there may also be provided with separate "stops" of known construction, for example, as illustrated in FIG. 19.

Magnet 40 is preferably entirely solid and thus is sometimes referred to herein as "solid magnet 40" for convenience of the reader. However, magnet 40 may be only substantially solid; i.e., there could be a small through-hole plugged with plastic, for example, or other conceivable interruptions to the integrity of the magnet 40 which would not prohibit system 35 from working sufficiently in the present system. However, for most efficient, ideal operation, magnet 40 is entirely solid.

Solid magnet 40 acts as a piston to apply force to hydraulic fluid 52 to thereby ultimately move a driven annular magnet 44 (as indicated by arrows A, in FIG. 1) along the length of L-VAD 74. The magnetic flux of annular driven magnet 44 and annular valve-seat magnet 54 are along the axial length of L-VAD 74 so that they are biased toward and tend to lock to one another. Movement of annular driven magnet 44 in turn moves high-ferromagnetic-constant annular valve-seat magnet 54. Blood 78 is therefore pumped by L-VAD 74 in the direction of the flow arrows B through aortic arch 80, as shown in FIG. 1.

Except for hydraulic fluid leakages, the reciprocating motion of solid driving magnet 40 is in phase with the reciprocating motion of annular driven magnet 44, but is slightly out of phase with the reciprocating motion of valve-seat magnet 54 due to flood, hydraulic fluid, and electromagnetic inertia effects. The out-of-phase separation of driven magnet 44 from valve-seat magnet 54 varies throughout the reciprocating cycle. These delays are accounted for in the time {t} expressions in equation (7) of the new process described later herein.

The reciprocating movement of driving magnet 40 along the length of hydraulic pump 42 is controlled by power, voltage and current from battery 62 to electromagnetic coils 46, 48 and 50 in the sequence depicted in FIGS. 17, 18 and 19 and described below. The timing and magnitude of the current from battery 62 is controlled by controller 64 in response to ECG signals initiated from the ECG signal 66, signals from measurements of ejected blood volume, and as a result of the optimization process explained below. Battery 62 and controller 64 can be connected as a battery/controller assembly 65, as illustrated, or utilized as separate components. The movement of driving magnet 40 is slightly out of phase with the magnetic field along electromagnetic coils 46, 48 and 50 due to electromagnetic hysteresis effects, which are also accounted for in the time {t} expression of equation (7) described herein below. The out-of-phase separation of driving magnet 40 from the magnetic field of electromagnetic coils 46, 48 and 50 varies throughout the reciprocating cycle and is mathematically accounted for by the optimization method described later herein to minimize the power required for operation of the new system.

Inside an inner sleeve 68 is contained an annular valve-seat magnet 54 which contains one-way valve 70. The sliding facing surfaces of annular valve-seat magnet 54 and the inner sleeve 68 are sized and shaped to be substantially fluid-fight to minimize leakage of blood therebetween. Similarly, the mating surfaces of annular driven magnet 44 and the inner sleeve 68 and outer sleeve 72 (shown in FIG. 6) are designed to minimize leakage between sliding facing surfaces thereof.

It is to be understood that several alternative embodiments to minimize leakage from the various mating elements are conceived. It is further to be understood that all elements of the new pumping device and the entire system for operation thereof are formed of suitable biocompatible, surgical grade materials. Such materials may be appropriately selected from materials that are now known, as well as new materials, which may yet be developed.

Hydraulic pump 42 drives hydraulic fluid 52 in the direction of the flow arrows through hydraulic line 59 and into annular space 86, located between inner sleeve 68 and outer sleeve 72. The reciprocating motion of hydraulic fluid 52 moves annular driven magnet 44, also located between inner sleeve 68 and outer sleeve 72. By reversing the direction of current flow in electromagnetic coils 46, 48 and 50, the direction of driving magnet 40 is reversed, hence the direction of hydraulic fluid 52 is also reversed; it follows that the direction of driven magnet 44 is reversed as well. As annular driven magnet 44 is moved by the flow of hydraulic fluid 52, magnetic interaction with valve-seat magnet 54 causes valve-seat magnet 54 to move along with annular driven magnet 44. Because one-way heart valve, for example, as indicated schematically at 70, is secured to valve-seat magnet 54, one-way valve 70 moves in the same direction as valve-seat magnet 54 and annular driven magnet 44. When one-way valve 70 moves in a direction away from aortic valve 76, it is closed and pushes blood 78 through aortic arch 80.

One-way valve 70 can be any artificial or natural heart valve. Some known valves are mechanical, some are biological and some are made with compliant man-made materials. Some one-way valves may also eventually be made with stem cell research. Depending upon the particular type of valve selected for the one-way valve 70, limits may be imposed on the optimization process of equation (7), due to the pressure differences the particular valves can withstand (e.g. prolapse may occur with some compliant heart valves). Such differences are taken into account in the selection for a particular system as may be necessary.

FIG. 1 depicts the state of BEEP system 35 at late systole of the native human heart, when valve-seat magnet 54 is at the beginning of its pumping stroke along the length of L-VAD 74. At the stage of the cycle shown in FIG. 1 the ECG signal 66 and other volume and pressure signals have been transmitted along wire 63 to controller 64. (Wire 63 may also be inside of conductor 410 in the embodiment shown in FIG. 27 and discussed hereafter.) In response to these signals and the new optimization process, controller 64 discharges electrical power, voltage and current to hydraulic pump 42 along wires 67, 69 (and 71, in some cases). Specifically, current from battery 62 has energized electromagnetic coils 46 and 48. In response to the energization of coils 46 and 48, driving magnet 40 has begun to move away from its position within electromagnetic coil 46 and has moved partially within the walls of electromagnetic coil 48 (a cross-sectional view of driving magnet 40 and electromagnetic coil 46 is shown in FIG. 5).

Figure 6:
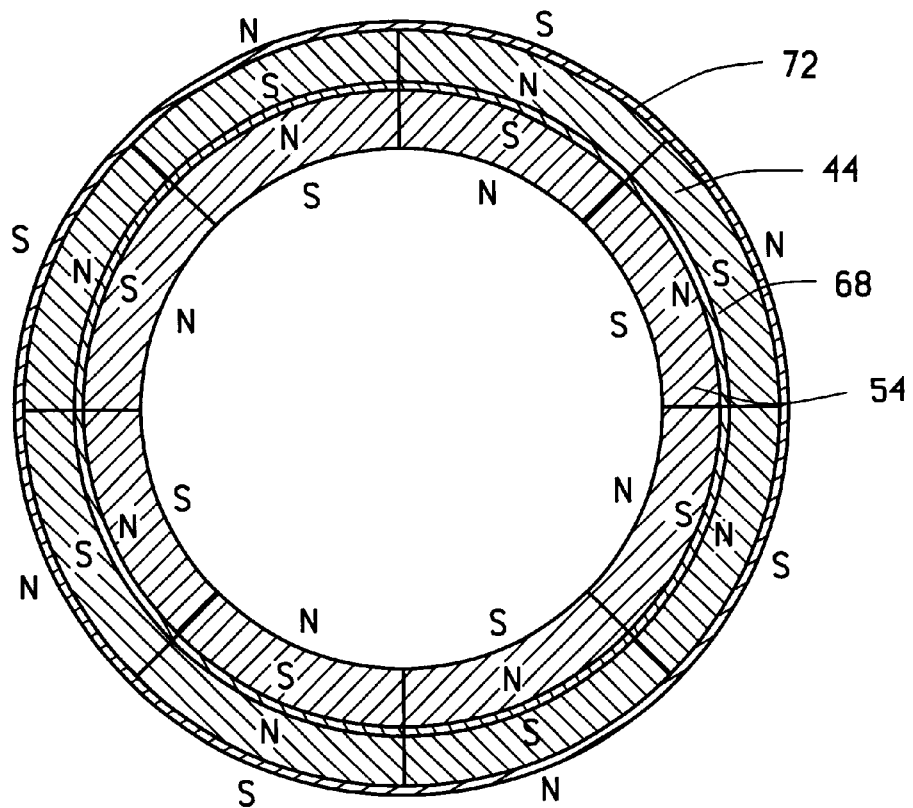
FIG. 6 is a cross-sectional view of the L-VAD of the BEEP system of FIG. 1, along line 6—6.

Further with reference to FIG. 1, the movement of driving magnet 40 has forced hydraulic fluid 52 to move through main hydraulic line 60 and secondary hydraulic line 82. The motion of hydraulic fluid 52 places pressure on both driven magnet 44 and check valve 84. Check valve 84 is closed, as is normally the case, securing the required pressure gradient between the high-pressure and low-pressure imposed by the motion of driving magnet 40 within hydraulic pump 42. Due to pressure from hydraulic fluid 52, annular driven magnet 44 has just begun to move along the length of L-VAD 74, within annular space 86. Magnetic interactions have caused valve-seat magnet 54 to move in a corresponding manner. Driven magnet 44 is located slightly ahead of valve-seat magnet 54 due to electromagnetic and fluid inertia. A cross-sectional view of L-VAD 74, through outer sleeve 72, annular driven magnet 44, inner sleeve 68, and valve-seat magnet 54 is shown in FIG. 6. The function of the two magnets, 44 and 54, is to magnetically "lock" to each other so that the movement of magnet 54 is affected by the movement of magnet 44. By "lock" it is meant that the motion of one magnet affects the motion of the other magnet via their magnetic interaction, even though the dynamics of the system may dictate that the motions of the two magnets may be out of phase. Hydraulic vessel (or "sleeve" in some cases) 72 for magnet 54 and blood vessel 68 for magnet 44 may be concentric or not, parallel or not, and may have any cross-section. It will be obvious to those with ordinary skill in the art that there are several alternative embodiments for the cross-sectional view of the hydraulic and blood vessels (parallel axes or not, concentric axes or not, circular, rectangular or other cross section etc) and the exact location and orientation of north and south poles of the magnets, and these are included herein.

Aortic valve 76, located at the outlet of the left ventricle 90, has been retained open by the beginning of the movement of one-way valve 70, which is closed and is being moved upward by driven magnet 44. The difference in axial location of driven magnet 44 and valve-seat magnet 54 is due to fluid inertia, but also due to magnetic inertia. Neither fluid inertia nor magnetic inertia is accounted for in the prior art. Although in this embodiment it is preferred that one-way valve 70 is an artificial valve of known or newly developed variety, valve 70 may also, if desired or necessary, be a natural heart valve or a one-way valve formed of tissue (human or other animal).

The movement of closed one-way valve 70 is beginning to pump blood along the length of the ascending aorta 88 and into the aortic arch 80.

Figure 2:
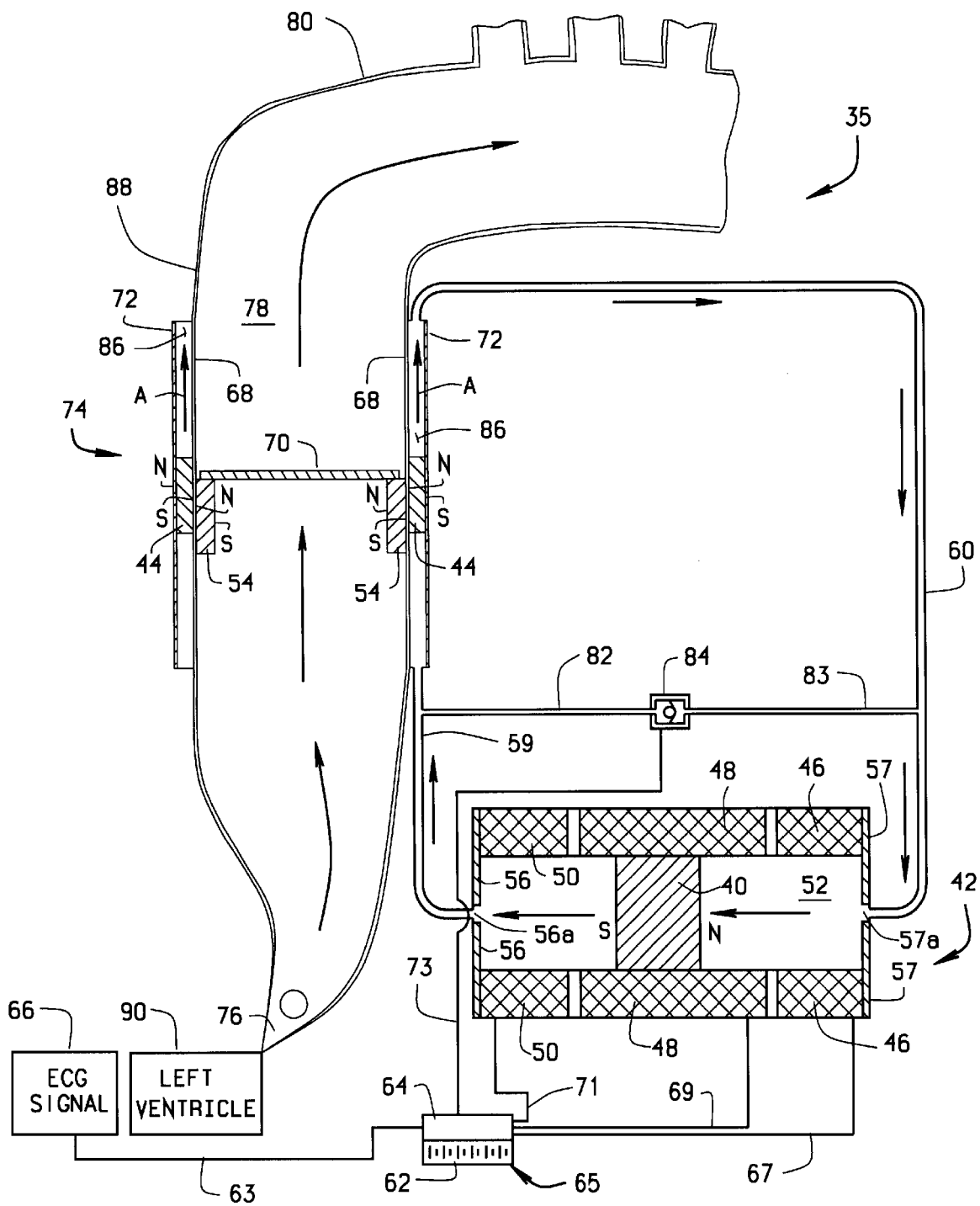
FIG. 2 is a schematic view of the L-VAD embodiment of a BEEP system of FIG. 1, wherein the system is near the middle of the blood-pumping stroke.

FIG. 2 depicts the state of BEEP system 35 halfway through the pumping motion of L-VAD 74. In this figure driving magnet 40 has moved within the walls of electromagnetic coil 48, approximately halfway through its motion along the length of hydraulic pump 42, and electromagnetic coil 50 has been energized by current from battery 62. The continued motion of driving magnet 40 has placed further pressure, via hydraulic fluid 52, on annular driven magnet 44. Due to magnetic interactions with annular driven magnet 44, valve-seat magnet 54 has moved approximately halfway through its motion along the length of L-VAD 74. Still closed, one-way valve 70 has pumped more blood, that would otherwise not have been pumped by the native heart, out of the left ventricle along the length of the ascending aorta 88 and into aortic arch 80. Aortic valve 76 remains open, allowing the flow of blood from the left ventricle 90 into ascending aorta 88.

Figure 3:
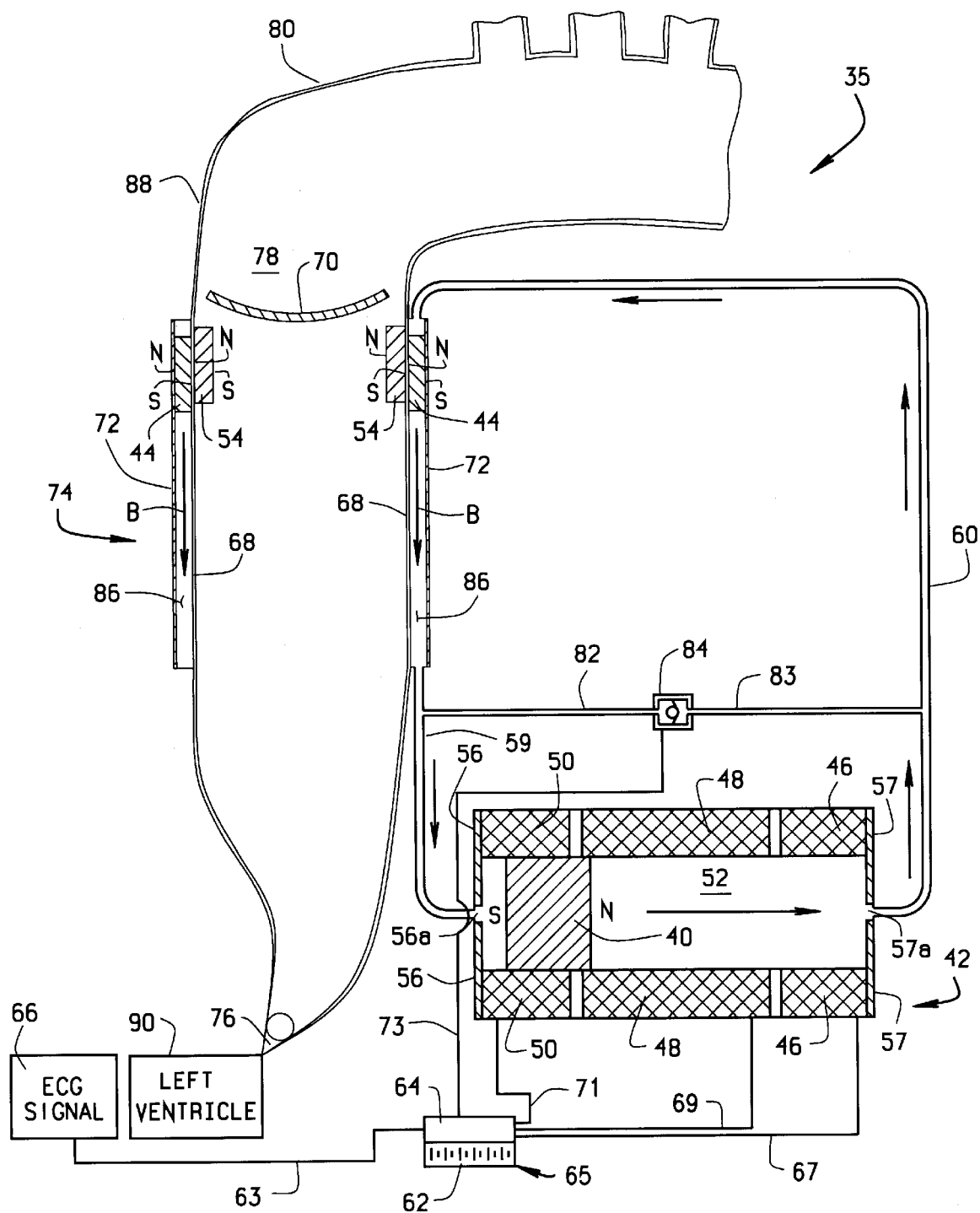
FIG. 3 is a schematic view of the L-VAD embodiment of a BEEP system of FIG. 1, wherein the system is at the beginning of the return stroke.

FIG. 3 depicts the state of BEEP system 35 at the beginning of the return stroke of valve-seat magnet 54. As driving magnet 40 reverses its previous motion along the length of hydraulic pump 42, the flow of hydraulic fluid 52 through main hydraulic line 60 is reversed as well, as indicated by the flow arrows in the Figure. The reverse flow of hydraulic fluid 52 places pressure on annular driven magnet 44, pushing it back along the length of the L-VAD 74, in the direction of aortic valve 76. As annular driven magnet 44 moves back along the length of L-VAD 74, valve-seat magnet 54 and one-way heart valve 70 move in a corresponding manner. One-way valve 70 is open as it moves toward aortic valve 76, allowing blood to flow freely through one-way valve 70 as it moves. Aortic valve 76 is closed at this time, preventing blood from flowing out of the L-VAD 74 and into left ventricle 90.

Figure 4:
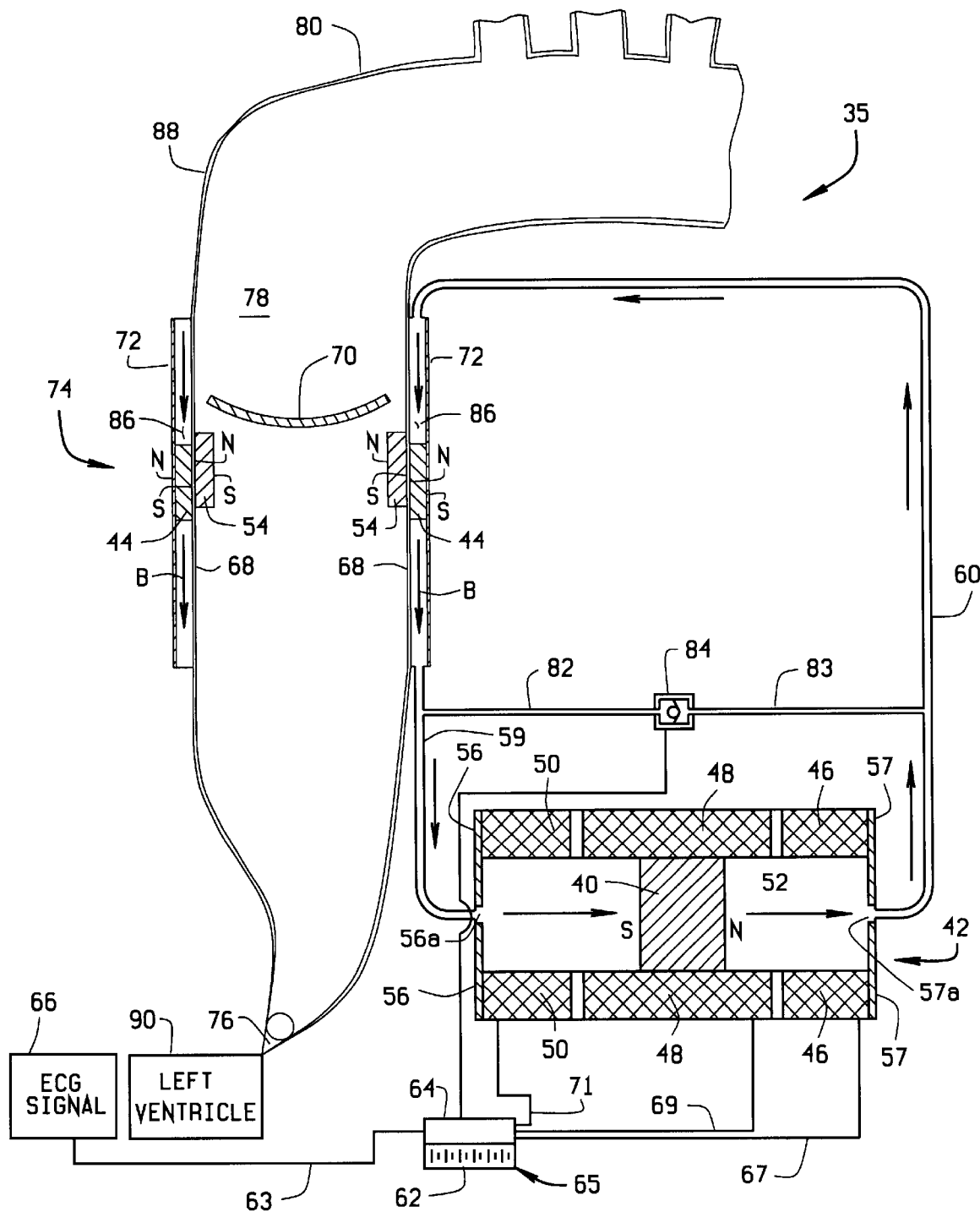
FIG. 4 is a schematic view of the L-VAD embodiment of a BEEP system of FIG. 1, wherein the system is near the middle of the return stroke.

FIG. 4 depicts the state of BEEP system 35 halfway through the return stroke of valve-seat magnet 54. Driving magnet 40 has moved back within the walls of electromagnetic coil 48, approximately halfway through its return motion along the length of hydraulic pump 42. The continued motion of driving magnet 40 has placed further pressure, via hydraulic fluid 52, on annular driven magnet 44, pushing it back down along the length of L-VAD 74. Valve-seat magnet 54 has moved approximately halfway through its return motion along the length of L-VAD 74. One-way valve 70 is still open, allowing blood to flow freely through it as it moves. Aortic valve 76 remains closed, preventing the flow of blood from L-VAD 74 into left ventricle 90.

Pulsatile Flow and the Present Approach:

The principles of fluid dynamics require a measurable work per cycle (and power output) from the heart to overcome the pressure difference in the passages of the circulatory system. Providing pulsatile instead of steady flow, accelerating and decelerating blood and muscle, consumes significant measurable additional work (and power) from that required for steady flow. If the natural heart provided continuous flow under constant pressure, then thrombi would tend to form and gradually enlarge in relatively stagnant or low-velocity flow regions. In steady flow conditions these thrombi would tend to become larger with time. Eventually the larger thrombi could potentially be dislodged by the surrounding flow causing blockage in narrower passages downstream. The results would be disastrous. The human body would not provide more pulsatile flow than that required for physiological reasons.

The human body requires pulsatile blood flow for survival, and a successful artificial heart pump or VAD should emulate the type of pulsatile blood flow provided by the native heart. Unlike known art devices, the present invention produces an optimized pulsatile flow. The VAD of the present invention provides the "vector" or "matrix" difference between the unsteady flow required by the human body and the unsteady flow provided by the native diseased heart, hence supplying only the required deficit. By "vector" or "matrix" difference we imply that this is not a simple subtraction of two quantities, as it will become evident in the following. In a total replacement configuration (TAH) the invention provides the total unsteady flow required by the human body. While other inventions purport to optimize the flow, the present invention illustrates the actual requirements (engineering principles) for this optimization.

The physical dimensions of the VAD or total replacement heart must be optimized to each application (i.e. to each patient). The moving mass, damping and stiffness of the combined system (moving parts of the VAD plus native heart, if any, plus driven blood flow through the vessels plus hydraulic fluid, surrounding tissue, electromagnetic dynamic phenomena, etc.) must be optimized to the dynamic response of the system (which is a form of the natural frequencies and damping of the overall system). If these conditions are not met, then the VAD or total replacement heart will be inefficient; it will require more power than the minimum to obtain the desired unsteady-flow output to the body. A good physical example of this is a yo—yo. If the string is pulled with the right forces at the right times (which corresponds to the optimized forcing function for the yo—yo), it requires minimum effort for maximum periodic travel and produces spectacular results. If either the forcing function or the timing are not exactly right, then it takes more effort to obtain any travel, and the results are not as good. Another equally important aspect of the invention is that the physical arrangement and dimensions of the invention are optimized to the desired amplitude and frequency of the unsteadiness in blood flow required by the circulatory system.

Thus the power input to TAHs and VADs must be optimized to the dynamic response of the system, otherwise the efficiency will be low (they will require a lot of power to drive them). One of the claims of the proposed VAD is that its driving force-time and force-distance relationships are optimized for minimum power input to the desired unsteady-flow characteristics, via a prescribed procedure, thus increasing its efficiency. This is done via a mathematical method described below. A pre-requisite for the use of this method is a deeper understanding of details of the flow and pressure conditions in the cardiovascular system than that in present medical and bioengineering practice. In other words, one needs to understand the details of the pressure and flow traces in the native as well as the artificial systems in order to design an efficient VAD or TAH.

While it is understood that the pressure trace changes phase and amplitude downstream from the aorta, there is no acknowledgement as to whether the measured pressure traces are static, stagnation or total pressures (defined in most fluids engineering texts). While it is clear that during most of systole the left ventricular pressure must be higher than the aortic pressure (otherwise flow would be in the reverse direction from the aorta to the ventricle), some texts indicate otherwise. The premise of this disclosure is that any TAH or VAD must be optimized around the details of the pumping system and match the requirements of the human body.

Static pressure $p_{st}$ is the pressure one would feel while traveling along with the velocity of the fluid in a channel. Stagnation pressure $p_0$ is the pressure one would feel with the fluid coming to rest against the measuring device. Total pressure $p_T$ is the stagnation pressure plus the static head of a column of fluid above the measuring point.

For a perfect incompressible fluid of constant density ρ (which is one of many frequently used mathematical models for blood) moving with velocity C the governing equations are:

$$p_0 = p_{st} + \rho C^2/2$$

$$p_T = p_{st} + \rho C^2/2 + \rho g z$$

The distinction between these three pressures in the blood flow is important in the design of the optimal VAD, as is the choice of measurement devices that are specialized to distinguish measurement of static, stagnation and total pressures, and the location of these measuring devices in the system. Optimum design of the present device is integrally related to the fundamental laws of fluid mechanics applied for unsteady flow conditions to the thermodynamic system enclosing the heart and circulatory system. Those skilled in the art of unsteady thermofluid dynamics will recognize that the system definition is of paramount importance to the solution of the problem, and must be defined with the accuracy and detail suggested in the text by Gyftopoulos and Beretta (1981); i.e. the system definition will require amounts and range of valves for: matter, parameters or constraints, and interacting forces between system elements. These fundamental laws are usually expressed as one equation for conservation of mass, three equations for conservation of momentum, for example, along (x, y, z), and a fifth equation for the energy balance (the first law of thermodynamics).

The following equations (1–5) are valid for any fluid continuum (compressible or incompressible, Newtonian or non-Newtonian), and they are general in nature. The nomenclature used is as follows:

| | |
|---|---|
| $E_t, e_t$ | energy and energy per unit volume, including internal, kinetic, and potential energy, etc. |
| e | specific internal energy |
| $\vec{f}_{bd}$ | external body forcing function per unit volume (gravity, electromagnetic, etc.) |
| $\vec{f}_{sf}$ | surface forcing function per unit volume (resulting in stress tensor τ) |
| $F_{nh}\{t\}$ | force as a function of time from the native heart |
| $F_{vad}\{t\}$ | force as a function of time from the VAD |
| h | specific enthalpy |
| m | mass |
| p | pressure |
| Q, $q_x$, $q_y$, $q_z$ | heat into control volume, and heat per unit volume in (x, y, z) coordinates |
| t | time |
| (x, y, z) | Cartesian coordinates |
| u, v, w | velocity components alone (x, y, z) coordinates |
| W | work into the control volume (from surface, from shaft, etc.) |
| x | axial direction |
| ρ | density |
| μ | dynamic viscosity |
| τ | stress tensor |
| $\tau_{ij}$ | element of stress tensor (includes pressure) along (i, j) coordinates |
| ∇ | divergence operator |
| D | total derivative operator |
| ∂ | partial derivative operator |

The mass balance (continuity) is given by:

$$\frac{\partial \rho}{\partial t} + \vec{\nabla}(\rho \vec{v}) = 0 \quad (1)$$

$$\frac{\partial \rho}{\partial t} + \frac{\partial (\rho u)}{\partial x} + \frac{\partial (\rho v)}{\partial y} + \frac{\partial (\rho w)}{\partial z} = 0$$

where the equation can be further simplified using certain assumptions such as incompressible fluid (but here we consider the general form of the equation with no restrictions other than continuous fluid).

The vector form of the equation for conservation of linear momentum can be written as the (x, y, z) momenta equations:

$$\frac{\partial (\rho \vec{v})}{\partial t} + \vec{\nabla}(\rho \vec{v} \vec{v}) = \vec{f}_{sf} + \vec{f}_{bd} = \vec{\nabla} \vec{\tau} + \vec{f}_{bd}$$

$$\frac{\partial (\rho u)}{\partial t} + \frac{\partial (\rho u^2)}{\partial x} + \frac{\partial (\rho u v)}{\partial y} + \frac{\partial (\rho u w)}{\partial z} = \quad (2)$$

$$\frac{\partial (\tau_{xx})}{\partial x} + \frac{\partial (\tau_{xy})}{\partial y} + \frac{\partial (\tau_{xz})}{\partial z} + \vec{f}_{x,bd}$$

$$\frac{\partial (\rho v)}{\partial t} + \frac{\partial (\rho v u)}{\partial x} + \frac{\partial (\rho v^2)}{\partial y} + \frac{\partial (\rho v w)}{\partial z} = \quad (3)$$

$$\frac{\partial (\tau_{yx})}{\partial x} + \frac{\partial (\tau_{yy})}{\partial y} + \frac{\partial (\tau_{yz})}{\partial z} + \vec{f}_{y,bd}$$

$$\frac{\partial (\rho w)}{\partial t} + \frac{\partial (\rho w u)}{\partial x} + \frac{\partial (\rho w v)}{\partial y} + \frac{\partial (\rho w^2)}{\partial z} = \quad (4)$$

$$\frac{\partial (\tau_{zx})}{\partial x} + \frac{\partial (\tau_{zy})}{\partial y} + \frac{\partial (\tau_{zz})}{\partial z} + \vec{f}_{z,bd}$$

where the body forces are exerted on the whole body of fluid (such as by gravity, when $\vec{f}_{bd} = \rho \vec{g}$; or by external electromagnetic fields); and the surface forces are exterted by the interior surface of the control volume of fluid. Some texts choose to separate the pressure terms from the stress tensor, but here the pressure terms are included in the stress tensor τ.

The energy balance equation is given by:

$$\frac{DE_t}{Dt} = \frac{DQ}{Dt} + \frac{DW}{Dt} \quad (5)$$

$$\frac{\partial (\rho e_t)}{\partial t} + \frac{\partial (\rho u e_t)}{\partial x} + \frac{\partial (\rho v e_t)}{\partial y} + \frac{\partial (\rho w e_t)}{\partial z} =$$

$$\frac{\partial (q_x + u\tau_{xx} + v\tau_{xy} + w\tau_{xz})}{\partial x} +$$

$$\frac{\partial (q_y + u\tau_{yx} + v\tau_{yy} + w\tau_{yz})}{\partial y} + \frac{\partial (q_z + u\tau_{zx} + v\tau_{zy} + w\tau_{zz})}{\partial z}$$

where $q_x$, $q_y$, $q_z$ are the external heat transfers (Q) in each direction, the work (W) terms are given by tensor times velocity applied to the surface of the control volume, and $E_t$ includes all the energy terms. For example, if these include only internal energy, kinetic energy, and potential energy, then $Ep_t = \sigma e_t = \sigma(e + |\vec{v}|^2/2 + \vec{g} \cdot \vec{r})$. However, in the general case, $E_t$ includes all energy terms affecting the solution of the equations.

The above five equations can be written in vector form as:

$$\frac{\partial G}{\partial t} + \frac{\partial A}{\partial x} + \frac{\partial B}{\partial y} + \frac{\partial C}{\partial z} = \frac{\partial X}{\partial x} + \frac{\partial Y}{\partial y} + \frac{\partial Z}{\partial z} \qquad (6)$$

where $G = [\rho, \rho u, \rho v, \rho w, \rho e_t]$ $A = [\rho u, \rho u^2, \rho u v, \rho u w, \rho u e_t]$ $B = [\rho v, \rho u v, \rho v^2, \rho w v, \rho v e_t]$ $C = [\rho w, \rho w u, \rho w v, \rho w^2, \rho w e_t]$ $X = \left[0, \tau_{xx} + \vec{f}_{x,bd}, \tau_{xy}, \tau_{xz}, q_x + u\tau_{xx} + v\tau_{xy} + w\tau_{xz}\right]$ $Y = \left[0, \tau_{yx}, \tau_{yy} + \vec{f}_{y,bd}, \tau_{yz}, q_y + u\tau_{yx} + v\tau_{yy} + w\tau_{yz}\right]$ $Z = \left[0, \tau_{zx}, \tau_{yx}, \tau_{zz} + \vec{f}_{z,bd}, q_z + u\tau_{zx} + v\tau_{zy} + w\tau_{zz}\right]$ (the native heart and VAD forcing function are terms $\vec{f}_{x,bd}$ in X, Y, Z).

The only restriction in the above equations 1–6 is that blood behaves as a continuous fluid (if it didn't, e.g. if there is cavitation, severe lysis, or severe clotting, then the model is inadequate, but the resulting VAD is also useless). These equations are valid for steady and unsteady flow (periodic and transient), with any external force field or surface forcing function, with heat transfer, with Newtonian or non-Newtonian fluids etc.

The resulting instantaneous equations of fluid motion (1–6) have instantaneous eigenvalues and eigenvectors that can be computed, and those must be matched with the combined forcing function from the native heart $F_{nh\{t\}}$ and the VAD $F_{nh\{t\}}$, i.e. the dynamic system of equations for the native cardio-rheology as modified by the presence of the operating VAD. The resulting instantaneous system of dynamic equations are of the form:

$$[M]\{\ddot{x}\}+[C]\{\dot{x}\}+[K]\{x\}=F\{t\}=F_{nh}\{t\}+F_{vad}\{t\} \qquad (7)$$

where [M], [C], [K] are the instantaneous non-linear mass, damping and stiffness matrices respectively of the dynamic model. They are non-linear because they change with time and with mathematical or experimental data model, because the human tissue and mechanical components are not linear, and because they change with instantaneous position and geometry (for example with open or closed valves), and also with daily condition of the patient. In any case the procedures to model the dynamic system are well established, and the fidelity of the dynamic model is improving with time as better experimental data and theoretical or numerical models become available for each component of the dynamic system.

The forcing function of the native heart $F_{nh}\{t\}$ to the dynamic system is provided by the human and can be measured (though it also can be modeled with basic physiological interactions). The forcing function of the VAD system is provided by the magnetic field to the coils, which is generated by the current and voltage to the coils, so that for a discretized dynamic system the instantaneous power (at any time t) by the VAD is balanced with:

$$W(t)=F_{vad}\{t\}\cdot\{\dot{x}\}+\text{losses}=V\{t\}\cdot i\{t\} \qquad (8)$$

where W(t) is the instantaneous power at any instant in time t, $\{\dot{x}\}$ are the elemental velocities at the displacements where elemental forces $F_{vad}\{t\}$ are acting, and the product V{t} i{t} represents the sum of the electric power (voltage times current) supplied to the coils. In one embodiment of the optimization procedure the physical dynamic systems are linked so that the left-hand side of equation (7) is linked directly in the optimization process to the right-hand side of equation (8). The losses are electromagnetic losses of transmitting magnetic flux from the coils to the magnets, and friction losses until this power reaches the elemental displacements {x} on which forces $F_{vad}\{t\}$ act, and other similar losses. These losses can be measured or modeled mathematically with techniques available in mechanics, fluid dynamics, electromagnetism, and other engineering texts. Thus the model includes muscle, tissue, blood, hydraulic fluid, and electromagnetic and mechanical effects of mass, damping and stiffness. For example, these include friction and leakage in the mechanical components and fluid passages, the hysteresis loop of the electromagnetic drive of the VAD (a condition commonly called "latching"), other electromagnetic losses, and the stress tensors in equations 1–6, so that the resulting fluid-structure system is driven in an optimal manner.

In general engineering systems, the power optimization and control-scheme optimization (such as those described later for the mechanical blood pumping device and patient) would be best applied to the actual system itself. In this particular system, namely the patient with the mechanical pump surgically implanted, it would be extremely difficult to perform the steady-state power optimization scheme, and difficult to perform the control-optimization scheme, as this may endanger the life of the patient. These best preferred embodiments of using the physical dynamic should eventually be possible after clinical trials. Alternative embodiments (alternative models) of the physical dynamic system are likely to be used for scientific development of the BEEP system. These are likely to use analytic, numerical, or experimental, etc., expressions, or their combination, to represent the physical dynamic system. These models can be of various degrees of complexity. Some of these models may represent the whole dynamic system, and others may represent only portions of the whole system. From the above it is easy to foresee that one group of such possible dynamic models may include the mechanical blood pump only, while others may, in addition, incorporate portions of the native heart and the circulatory system, etc. Similarly, one set of such models may concentrate on finding the optimum $F_{vad}\{t\}$, represented, for example, by forces and velocities acting on one of: a) valve seat magnet 54; b) driven magnet 44; or c)driving magnet 40, etc. With similar dynamic models of the electromagnetic and hydraulic systems, this forcing function, $F_{vad}\{t\}$, can be correlated with the instantaneous electric power to the coils (resulting in a form of equation (8)). The preferred embodiment of the dynamic system model directly correlates the forces on the left-hand side of equation (7) with the power on the right-hand side of equation (8). Alternative embodiments of the optimization schemes may use simplified portions of the whole dynamic system, such as those that find the force, $F_{vad}\{t\}$ on: a) valve-seat magnet 54; b) driven magnet 44; or c) driving magnet 40.

In this invention the forcing function F{t} in equation (7) consists of two parts, one provided by the native heart and the other provided by the VAD. For this purpose, "optimize" means minimizing the power required to drive the VAD while minimizing the shear stress imposed on the blood.

Again, the terms "optimize" and "complement" are used in reference to the devices and systems of the present invention, it is meant that at each heart beat and stroke of the VAD (used here to mean either the VAD or TAH as described below), several actions are carefully timed such that:

a) the native heart is allowed to pump as much blood as it can on its own before the VAD is activated;

b) as the blood-ejection phase of the native heart nears completion, the VAD is energized to provide additional pumping action;

c) the additional pumping action reduces the back pressure in that native ventricle so that the native ventricle pumps more than it would have pumped unaided;

d) the timing of the action, length of pumping stroke, and rate of pumping (stroke displacement versus time and resulting power input versus time) of the VAD are related to the native heart ejected blood volume and rhythm in a manner that minimizes power input to the VAD while meeting physiological constraints;

e) the optimization processes in d) take into account the dynamic interaction between the native heart and the VAD; and f) the optimization process and the control scheme are integrated with the resulting changes in blood ejected per heart beat and heart rate (beats per minute) by the combined action of the native heart and the VAD.

Specifically, the combination of the patient's native cardiovascular system and the VAD at any condition of flow rate and beating frequency supplied by the native heart will result in an optimal shape (function of location and time as shown in the Figure) for the forcing function provided by the VAD. The forcing function and frequency of the VAD are controlled as explained elsewhere in these documents. The equations presented above are general and they are not dependent on the details of the mathematical models. Some research teams will choose to simplify these equations using the incompressible fluid approximation, Newtonian fluid approximation, linear models in finite element method programs or linearized equations in computational fluid dynamics (CFD) approaches. All of these simplifications are fully included in the general equations (1–7).

The L-VAD is intended to be placed between the aortic root and the aortic arch. Thus, for VAD applications the length L and overall outside diameter $D_0$ of L-VAD 74 are limited by human physiology. There is a desire to directly wrap coils 46, 48 and 50 around the length of travel of driven magnet 54, but this not always possible, due to geometric constraints. For example, for an adult male L≈10 cm and $D_0$≈4 cm, the overall force that can be carried by a hollow magnet 54 is a function of the volume of the magnet, among other factors, for example, if cylindrical, approximated by $\pi(D_2^2-D_1^2)l/4$, where $D_2$ and $D_1$ are the outside and inside diameters of the magnet and l the length, the magnetic properties of the materials (factor k1), geometry (factor k2) and technology of components (e.g. leakage and friction characteristics, coil packing, heat transfer constraints (factor k3)).

$$f=F(k1, k2, k3)$$

where clearly, other factors being equal, the force is increased by increasing D2, the outside magnet diameter. Thus the outside diameter of electromagnetic coils used in the linear magnet motor of prior art becomes too big for VAD to fit into the human body in the vicinity of the aortic arch. This maximum-diameter issue is resolved with the use of driving magnet 44, the hydraulic fluid, and solid (or substantially solid) magnet 40. The following table is an indication for several distinct sizes of VADs, assuming that the diseased native heart provides 50% of the cardiac output required by the human body:

| | Weight (kg) | Height (m) | Area ($m^2$) | Normal Cardiac Output (cc) | Output of Diseased Native Heart (cc) | Required VAD Output (cc) |
|---|---|---|---|---|---|---|
| Child | 50 | 1.3 | 1.3 | 58 | 29 | 29 |
| Teen | 55 | 1.65 | 1.6 | 72 | 36 | 36 |
| Avg. Adult Female | 55 | 1.75 | 1.7 | 76 | 38 | 38 |
| Avg. Adult Male | 75 | 1.85 | 2.0 | 90 | 45 | 45 |
| Large Adult | 110 | 175 | 2.3 | 102 | 51 | 51 |

As can be seen by the equations above, several standard sizes of L-VAD 74 can be designed. As a guide, the smallest would be a pediatric device and the largest would be for a large adult. What follows is an example of calculations performed on a hypothetical individual, and is not intended to in any way limit the present invention.

The height and weight features of a person can be converted to body surface area by using the approximate formula below. Once body surface area is known, normal cardiac output for a given individual can be calculated. Normal cardiac output volume per body surface area is 45 cc/m².

$$\text{Body Surface Area } (m^2)=[ht(cm)]^{0.718}[wt(kg)]^{0.427}[0.007449]$$

Using a 75 kg 185 cm adult male as an example, the body surface area calculation results in a value of 2 m². Given the body surface area value of 2 m² calculated above, the normal stroke volume for the individual is 90 cc. In end-stage cardiomyopathy, the native heart provides approximately 50% of the required cardiac output. In the example above the native heart would provide approximately 45 cc. Therefore, the L-VAD would have to provide an additional 45 cc.

What follows is a general description of the approximate sizes of an L-VAD for the above patient at one ejection volume (45 cc) and one heart rate. The procedure must be repeated several times for different ejection volumes and heart rates before the optimum L-VAD dimensions for the patient are decided. The procedure is also affected by the size of available one-way valves 70, especially if these are of the standard artificial heart valves available commercially, which are available in several standard diameters, usually measured in millimeters (mm).

The maximum L-VAD displacement required in this example is 45 cc. A standard 29 mm valve nomenclature is used for one-way valve 70. This choice affects the length of L-VAD 74 as well as the force that must drive driven magnet 44 and valve-seat magnet 54. The axial length of driven magnet 44 and valve-seat magnet 54 is 13 mm. The wall thickness between driven magnet 44 and valve-seat magnet 54 is 1 mm, as is the thickness of outer sleeve 72.

For certain illustrative example cases the steady state and acceleration force required to pump blood through L-VAD 74 is 30 to 36 N (kg m sec$^{-2}$). This is based on an initial estimate of the pressure that will be supplied by L-VAD 74, multiplied by the area of the pumping diameter. This initial estimate accounts for the acceleration of fluids (blood and hydraulic) pumped in the system (about 6L in circulation), and the initial masses of the moving components. The volume of rare earth magnet in driven magnet 44 and valve-seat magnet 54 required to provide the 30 to 36 N is 3.83×10³ mm³. The resulting thickness of valve-seat magnet 54 with a length of 13 mm is about 3.2 mm. Thus, the inside diameter of valve-seat magnet 54 is 29 mm and the outside diameter is 35.4 mm. The inside diameter of driven magnet 44 is 37.4 mm. The thickness of driven magnet 44, with a length of 13 mm and an inside diameter of 37.4 mm, must be around 2.8 mm to achieve the desired 30–36 N. Thus, the outside diameter of driven magnet 44 is 43 mm. Therefore, the outside diameter of L-VAD 74 is 45 mm.

The stroke length required if one-way valve is to give the required 45 cc volume is 45.7 mm. Adding this to the axial length of valve-seat magnet (as required by the geometry of the device) the overall axial length of the pumping portion of L-VAD 74 becomes 58.7 mm. This length will be increased to allow for the cuffs for hydraulic fluid and blood. It is understood that several alternative embodiments for the cross-sectional shape of the heart valve 70, magnets 54, 44 and 40, and cuff (or "capsule") designs for the hydraulic connections for hydraulic fluid and blood can be used and will be apparent to one skilled in the art and thus they are hereby incorporated in this disclosure.

The above dimensions are used to provide geometric inputs for the models used in equation (7). The inputs result in elements for mass matrix [M], damping matrix [C], and stiffness matrix [K]. Elements of [M] are evaluated using material densities. Elements of [C] are evaluated using fluid dynamics for the flow passages, structural damping for tissues and electromagnetic properties for magnets, coils and other components, as needed. Elements of [K] are evaluated using material and surrounding tissue properties and electromagnetic properties for magnets, coils and other components, as needed. The surrounding tissue must extend to the control volume of the system where the tissue geometry is not moving. This means a little further out of the pericardium (to fully include pericardium tremors) and a little further out of the blood and hydraulic fluid vessels (to include stiffness and compliance, providing elements for [C] and for [K]). For example, the pressure drops in hydraulic lines 60 and 82 initially can be estimated using analytic calculations available in standard textbooks, and later evaluated by discretized mathematical models as elements of matrices in equation (7).

Continuing the above example, with certain engineering assumptions driving magnet 40 could be 3800 mm³ grade 37 rare earth magnet. In one embodiment this magnet could have radius 9.7 mm, and length 12.86 mm. The hydraulic volume displaced by 45.7 mm of stroke length of driven magnet 44 is 54.7 mm. Thus, the overall length of hydraulic pump 42 is about 81 mm (this length will be increased by the length of the hydraulic cuffs).

Additional secondary calculations are made to evaluate the geometries of auxiliary components such as hydraulic lines, and other components such as tissue in the myocardium and blood flow system. The inputs result in elements for matrices [M], [C], and [K] (some measured in clinical trials, others measured for individual patients). The elements of vector of displacements $\{x\}$ and its derivatives $\{\dot{x}\}$ and $\{\ddot{x}\}$ in equation (7) are elemental displacements. The equation is nonlinear and can be decomposed in a few or infinitely many degrees of freedom, depending on the fidelity of the dynamic model.

Figure 14:
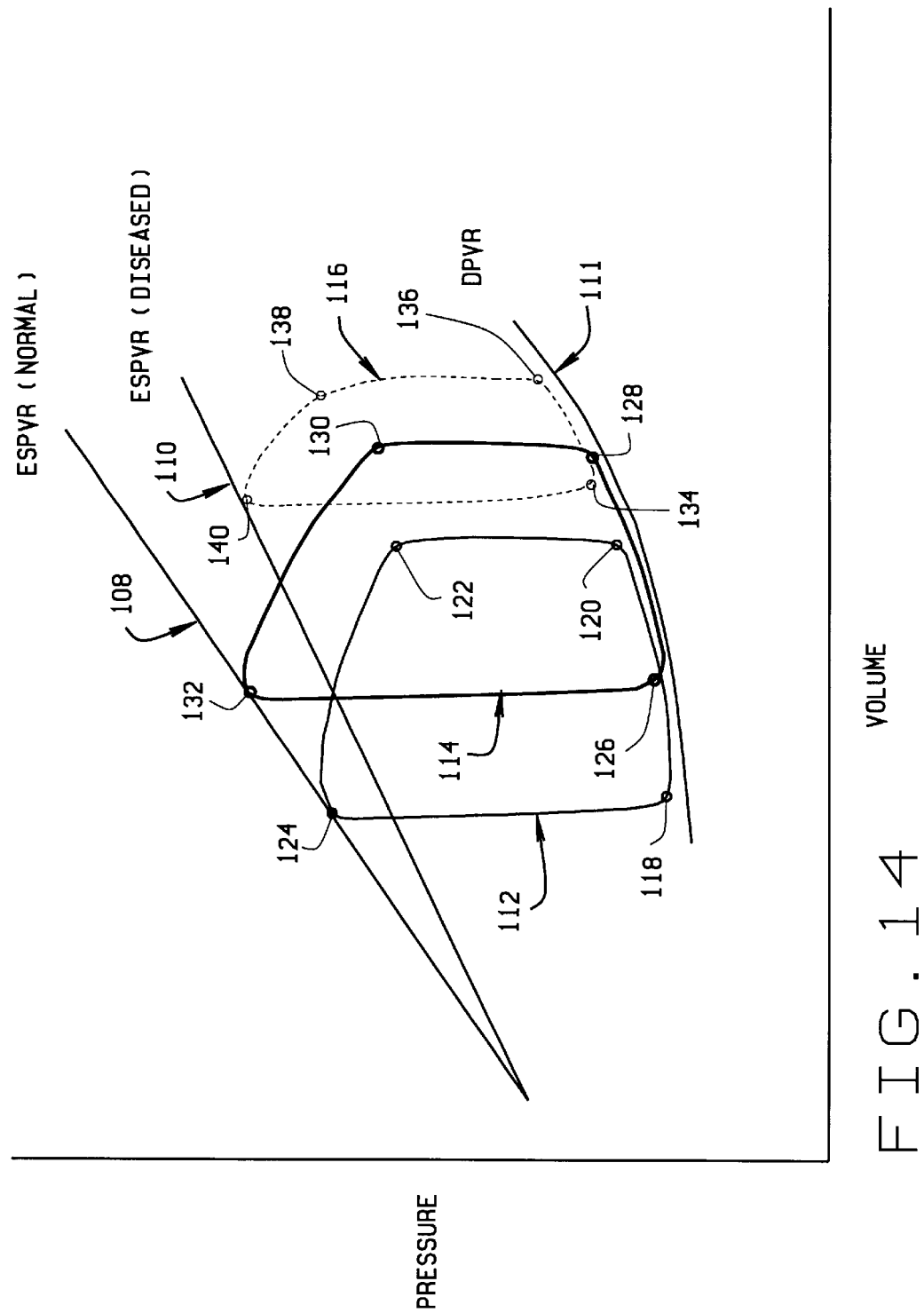
FIG. 14 is a graph illustrating typical pressure-volume diagrams of a native healthy heart and a native diseased heart.
Figure 15:
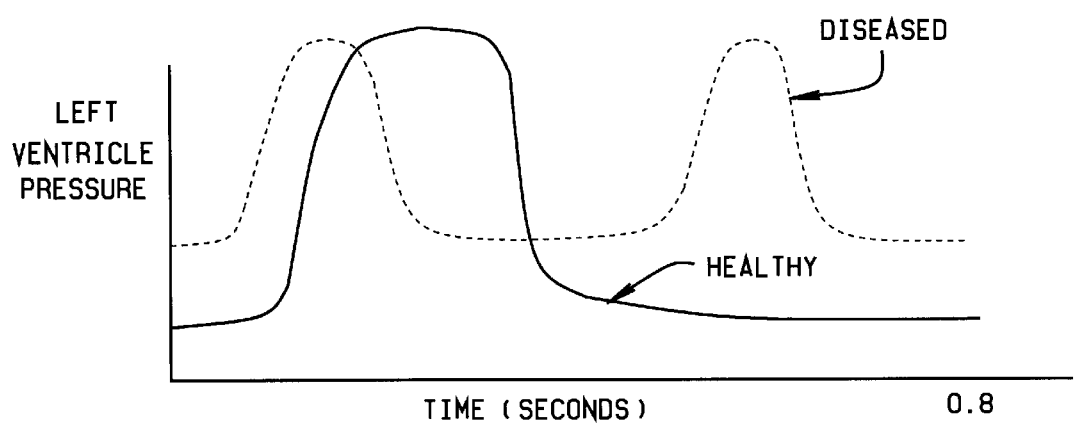
FIG. 15 is a left-ventricle pressure versus time diagram of a native healthy heart and a native diseased heart.

$F_{nh}\{t\}$ in equation (7) is measured for each condition (heart rate, ECG signal, volumes ejected from right and left ventricles, and pressures) of the patient. For L-VAD 74 this is given by the total pressure (static+dynamic+elevation components) provided by the diseased heart inside the left ventricle as a function of time (measured during the heartbeat) integrated over the inside surface area of the four chambers of the heart. This surface area is also measured with magnetic resonance imaging (MRI), echocardiography, or other similar technique. These give pressure-volume-time traces for the diseased heart as illustrated in FIGS. 14 and 15. The volume information is correlated with data from proximity sensors, such as 406 and 416 in FIG. 9, which may be, for example, proximity sensors. This information changes as the condition of the patient worsens or improves. This means that the data needs to be calibrated before surgery, and again soon after surgery, and monitored periodically so that the data provided by proximity sensors 406 and 416 reflect the forcing function provided by the native heart, where the mathematical expressions are:

$$dF_{nh}\{t\} = p(t)dA(t)$$

$$F_{nh}\{t\} \theta_A p(t)dA(t)$$

The resulting pressure-volume-time traces of the native heart have a phase associated with the timing of the forcing function $F_{nh}\{t\}$ during the beat. This can be modeled with Fourier series analysis of the pressure and volume signals of the native heart over time. Again, these vary with the rate (beats per minute) of the native heart and with the condition of the patient (i.e. the information changes as a function of time and needs periodic updating).

Figure 7:
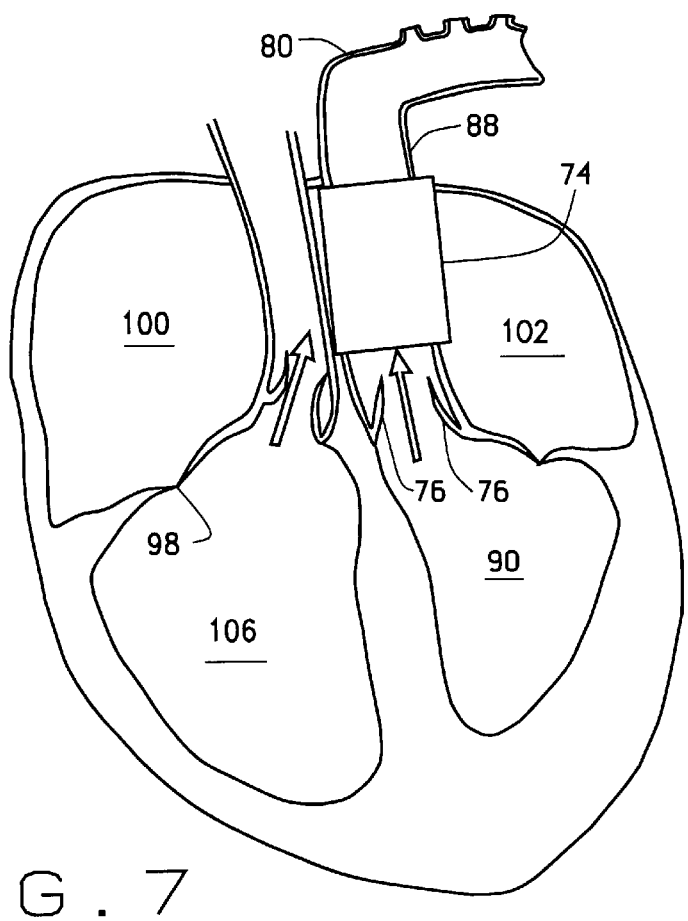
FIG. 7 is a schematic concept illustration of the human heart illustrating the location of an L-VAD in place of at least part of the ascending aorta.

FIG. 6 is a cross-sectional view of L-VAD 74, along line 6—6 of FIG. 1. By contrast, FIG. 7 is a concept illustration of the human heart showing the location of L-VAD 74 in place of ascending aorta 88. It is understood that the L-Vad may replace a portion, not necessarily the entire ascending aorta. Further in some embodiments the aorta may simply be transected to place the L-VAD outside the body, with blood conduits connecting the ends of the transected aorta to the L-VAD. Corresponding alternative embodiments are possible for the R-VAD, BI-VAd. Blood moves from left ventricle 90, through aortic valve 76 and into L-VAD 74, situated in place of the ascending aorta 88, pumps blood into aortic arch 80.

Figure 8:
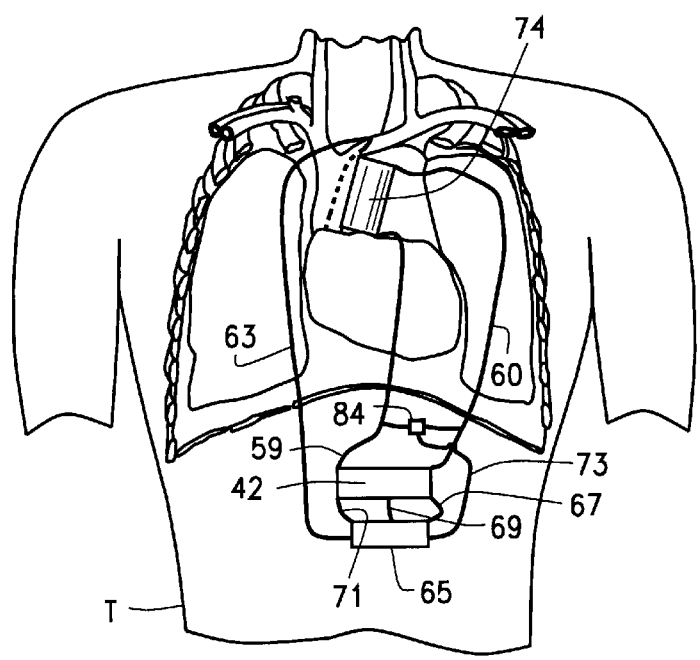
FIG. 8 a schematic sectional view of a human torso O, illustrating the location of the main components of an L-VAD embodiment of BEEP system 35 in the human body. The L-VAD is shown in place of the ascending aorta, and the hydraulic pump and battery/controller assembly are illustrated in the abdominal cavity.
Figure 20:
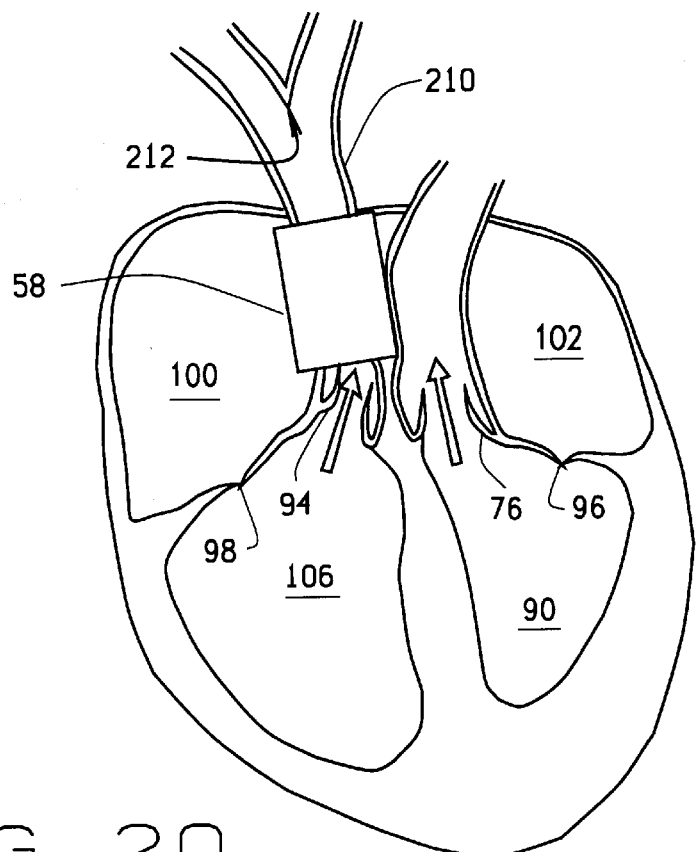
FIG. 20 is a concept illustration of the human heart illustrating the location of a right ventricular-assist device (R-VAD) embodiment of the BEEP system.
Figure 21:
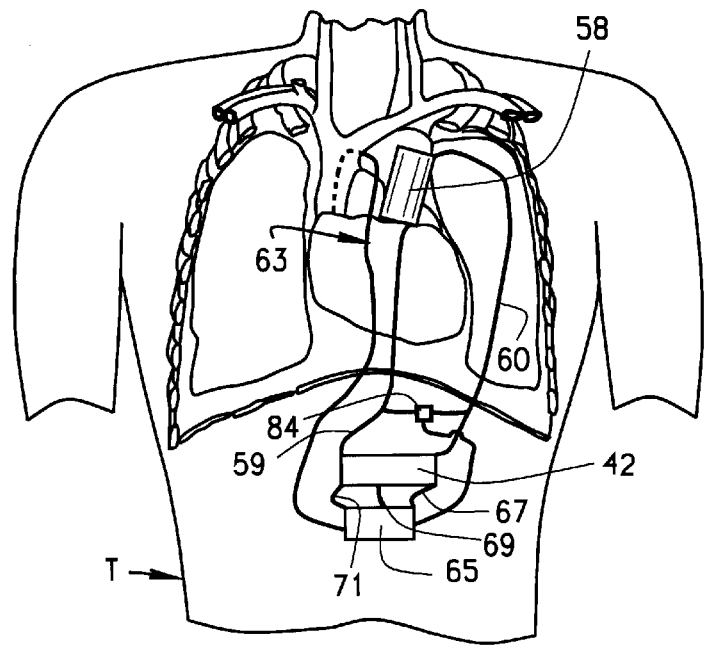
FIG. 21 a schematic view of the human torso illustrating the location of the main components of an R-VAD embodiment of a BEEP system in the human body.

FIG. 8 shows the placement of an entire BEEP system 35 within the human torso. The illustration depicts the spatial relationship between battery/controller assembly 65 and L-VAD 74. FIGS. 7 to 13 and 20 to 25 are schematic illustrations, not cross-sectional views, and the location of L-VAD 74 in FIG. 8 is at a different plane from the location of R-VAD 58 in FIG. 21. (The LVAD in FIG. 8 is correctly shown more to the right of the patient's chest than RVAD in FIG. 21, but FIGS. 8 and 21 are anatomically correct, while FIGS. 7 and 20 are simple arrangement illustrations).

Figure 9:
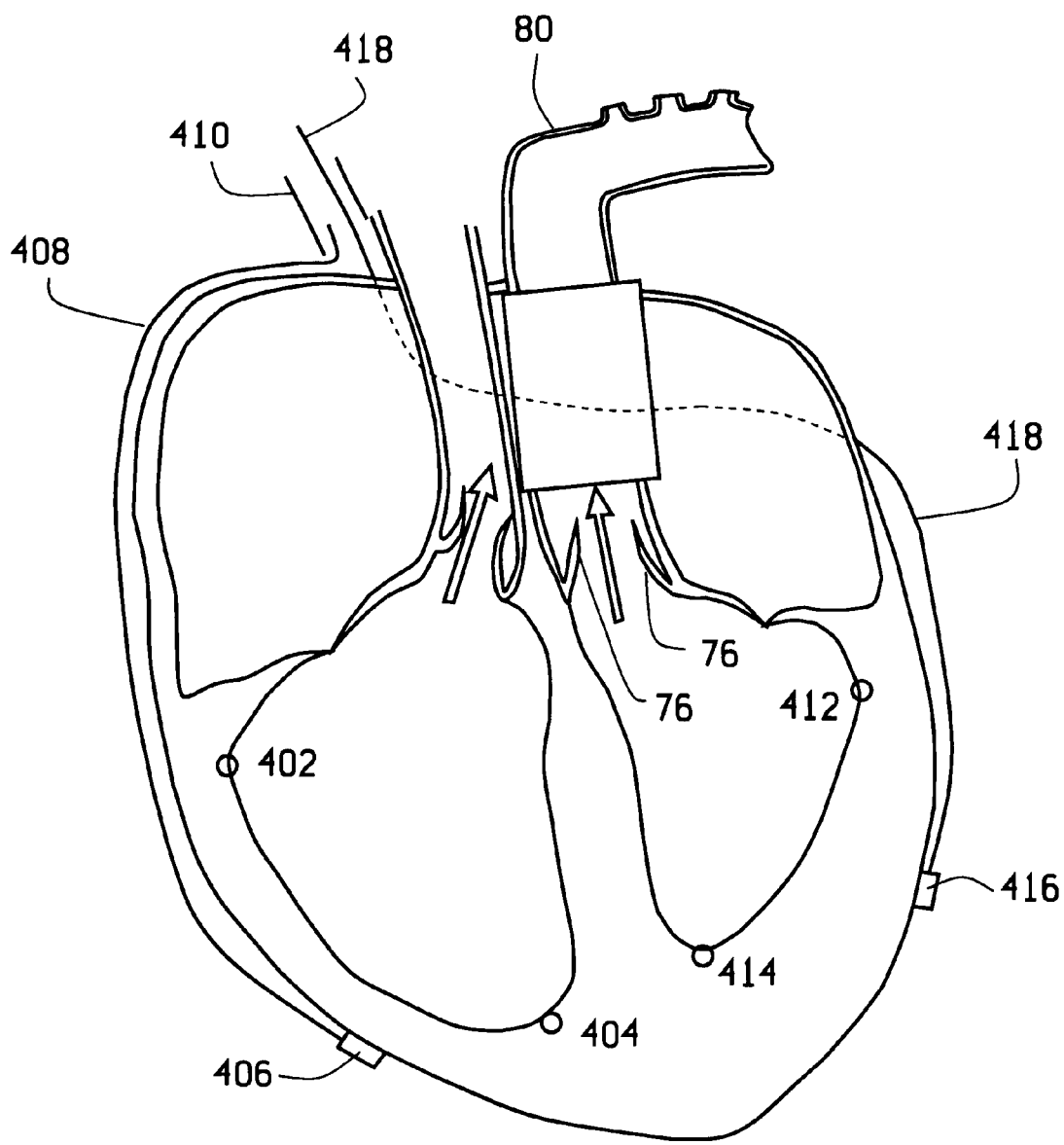
FIG. 9 is a concept illustration of the human heart illustrating location of proximity sensors embedded in the endocardial surface of the left and right ventricles, and mounted on the pericardium.

FIG. 9 is a concept illustration of the human heart, illustrating a technique to measure the volumes of the left and right ventricles, which is used in the control algorithm. Rare earth (or similar material) magnets 402 and 404 are embedded in the endocardial surface of the right ventricle, and their relative motion changes the magnetic field between them. These changes are measured by proximity sensor 406, mounted on the pericardium. The signal is transferred by electrical lead 408 to wire bundle 410. Rare earth or similar material magnets 412 and 414 are embedded in the endocardial surface of the left ventricle, and their relative motion changes the magnetic field between them. These changes are measured by proximity sensor 416, mounted on the pericardium. The signal is transferred by electrical lead 418 to wire bundle 410. The signals from wire bundle 410 are transmitted to controller 64 and used as described later.

The proximity sensors are currently available devices that may operate on the resistive, capacitative or inductive principles, or combinations, or other similar distance-measuring technology. Auxiliary (parallel horizontal) lines 1 through 6 in FIGS. 10 through 13 represent the motion of the ventricles and the KG diaphragm (see below) during a cardiac cycle. It has traditionally been thought that the valves of the heart open to let the blood through when the chambers contract, and snap shut to prevent it from flowing backward as the chambers relax. While this is correct, the valves also act as pumping pistons for at least a portion of the cardiac cycle, a fact not known to be previously recognized in the literature. The plane of the valves and the supporting tissue on the perimeter of the valves form an internal diaphragm, approximately in the horizontal plane, which buckles and moves in 3D, which is also not known to be named in the existing literature. For the purposes of this document this diaphragm will be the Korakianitis-Grandia (KG) diaphragm, illustrated in FIGS. 10 to 13, and generally designated at 92. KG diaphragm 92 has four quadrants with a valve in each quadrant. It is activated by the surrounding cardiac muscle, which forces the diaphragm into a periodically-changing three-dimensional surface. (Thus FIGS. 10–13 are illustrations rather than cross-sections of the human heart). During the cardiac cycle the aortic valve and pulmonary valve stay nearly immobile (which allows one to place the VAD on the outlet side of these two valves); but the mitral and tricuspid valves move substantially, contributing at least in part to the pumping action of the ventricles. The mitral valve movement is comparable to the movement of the inside wall of the left ventricle. The tricuspid valve exhibits an even greater excursion and corresponding pumping action and is actually used in current medical practice as a measure of right ventricular ejection fraction.

While the exterior surface of the heart moves slightly during the cardiac cycle, the volume of the four-chamber heart does not change appreciably in time. However, the known art does not recognize that the total overall volume of each of the two sides, left and right, of the heart does not change appreciably during the cardiac cycle, even though the ventricular and atrial septa move. In operation of the native heart, during left ventricular ejection, the left atrium concurrently expands (while filling for the next cycle), and KG diaphragm 92 begins to move towards the apex of the heart, with complementing motions of the atrial septum and of the ventricular septum, thus keeping the overall volume of the left side of the heart about constant. Apex of the heart is a common term for the tip of the left ventricle. Similar arguments keep the right-side volume approximately constant, while the right and left sides of the heart expel blood to the lungs and the aorta about simultaneously. Minor deviations from these equal-volume considerations on each side, right and left, occur due to one side of the heart beating slightly before the other, heart-muscle and blood-vessel elasticity, transient accelerations or decelerations of the overall cardiac cycle (governed by the body's demand), and blood compressibility (which at circulatory system pressures is practically negligible).

The human cardiac cycle consists of two phases, conventionally called diastole and systole. During diastole (FIGS. 10 and 13) the ventricular muscle is relaxing, KG diaphragm 92 moves toward the base of the heart while the aortic and pulmonary valves are closed, and the mitral and tricuspid valves are open and moving towards the base of the heart, thus increasing the volume inside the ventricles while concurrently decreasing the volumes inside the atria. Base of the heart is a common term for the posterior aspect of the heart, behind the atria in the heart's anatomical position. The open mitral and tricuspid valves move upwardly (when the body is upright) to engulf blood from what was volume inside the atria (thus concurrently increasing the volume inside the ventricles while decreasing the volumes inside the atria). In a model of ventricular flow this volume exchange would affect the thermodynamic system definition, mentioned previously. A scrutinizing review of echocardiography tapes reveals that radial volume changes around the vertical axes of the ventricles account for roughly 75% of the volume change, with the corresponding movement of the KG diaphragm accounting for the remaining 25% volume change. There is heart-muscle work associated with these changes in volume that must be accounted with the correct mathematical model in any attempt to model flow in the heart or in VAD mimicking the function of the heart By the end of diastole, the relaxing ventricle allows KG diaphragm 92 to move toward the base of the heart. During initial systole (FIG. 11) the aortic and pulmonary valves remain closed while pressure is building up inside the ventricles. Subsequently the blood pressure inside the left ventricle becomes higher than the pressure in the ascending aorta, and the aortic valve is opened by blood flowing out of the ventricle. Substantially concurrently the blood pressure inside the right ventricle becomes higher than the pressure in the pulmonary trunk, and the pulmonary valve opens. The motion of the KG diaphragm carrying the mitral valve toward the apex of the heart, along with the simultaneous concentric contraction of the ventricle, ejects blood into the ascending aorta.

Correspondingly, the movement of KG diaphragm 92 carrying the tricuspid valve towards the apex of the heart, along with the simultaneous contraction of the right ventricle, ejects blood into the pulmonary trunk. This same motion of the KG diaphragm with the tricuspid and mitral valves closed increases the volumes inside the atria, hence refilling the atria with blood from the pulmonary veins (left atrium) and the vena cava (right atrium). Towards the end of systole the aortic and pulmonic valves close, then the mitral and tricuspid valves open and the cycle starts anew. Each cycle takes approximately one second.

The double throb ("lub dub") of the beating heart is generated by the snapping of the closing valves, but also from the accompanying vibrations of the surrounding heart muscle and contained blood.

The three-dimensional motion of KG diaphragm 92 forces each one of the four one-way valves to act as pumping pistons for at least part of the cardiac cycle. The blood flow must be optimized around artificial heart valves to provide the desirable flow and pressure pattern while minimizing shear stresses on blood cells.

FIG. 10 represents late diastole. At this point KG diaphragm 92 is at its uppermost position (horizontal lines 1–3). Pulmonary valve 94 and aortic valve 76 are closed, and mitral valve 96 and tricuspid valve 98 are open, completing filling of ventricles 106 and 90 following contraction of right atrium 100 and left atrium 102. Ventricular myocardium 104 is in its relaxed state.

FIG. 11 represents early systole. At this point ventricular myocardium 104 is thickened concentrically, and KG diaphragm 92 is moving downward (horizontal lines 2–4), the tricuspid valve side more so than the mitral valve side. Due to this motion, the volume of ventricles 106 and 90 is decreased while that of atria 100 and 102 is increased. Hence, the total volume of the heart remains essentially constant.

FIG. 12 represents late systole. At this point ventricles 106 and 90 have maximally thickened concentrically, and KG diaphragm 92 has been pulled maximally downward (lines 4–6). This completes the emptying of the ventricles.

FIG. 13 represents early systole. At this point KG diaphragm 92 is beginning to return upward (lines 3–5) toward atria 100 and 102, while ventricular myocardium 104 relaxes concentrically. As a result of this motion, the volume of atria 100 and 102 decreases while that of ventricles 106 and 90 increases, hence the overall volume of the heart remains essentially constant.

There are minor variations to the basic steps outlined above, due to damping and elasticity of the heart tissues, and small amounts of native heart valve leakage, which can be accounted for in the thermodynamic system definition mentioned earlier.

FIG. 14 represents pressure-volume loops for healthy (solid lines) and diseased (broken lines) hearts, with pressure plotted along the Y axis and volume plotted along the X axis. Line 112 represents a healthy heart. Point 118 to point 120 represents ventricular filling. Point 120 to point 122 represents "isovolumetric contraction". Point 122 to point 124 represents ejection during systole. Point 124 to point 118 represents isovolumetric relaxation.

Line 114 represents the normal response in accordance with the Frank Starling law to an increase in volume. Points 126, 128, 130 and 132 correspond to points 118, 120, 122, and 124, on line 112, respectively, and represent the corresponding phases of the cardiac cycle. Notice that points 124 and 132 lie on the same line, commonly referred to as the End Systolic Pressure Volume Relationship (ESPVR).

Line 116 represents a diseased heart which has exceeded the limits of the Frank Starling curve. In these hearts, the end diastolic pressure and volume are elevated but the end systolic pressure is decreased from that associated with normal myocardium, as noted by a lesser slope of the ESPVR line. Points 134, 136, 138 and 140 correspond with points 118, 120, 122 and 124 of line 112, respectively.

FIG. 15 represents ventricular pressure over time of the healthy and diseased hearts. Again, the end diastolic ventricular pressure is greater in the diseased heart than in the healthy heart, and because the ejection fraction is decreased in the diseased heart, the heart rate is increased so that the total cardiac output is maintained.

VADs are activated by either ECG signal, or via a fill-to-empty mode. The control algorithm of the present device utilizes inputs from the ECG of the native heart, as well as a measurement of the ejection volume and pressures of both the right and left ventricles. As a result, the prior art complication of mismatch of ejection volume between the right and left ventricles is eliminated.

Figure 16:
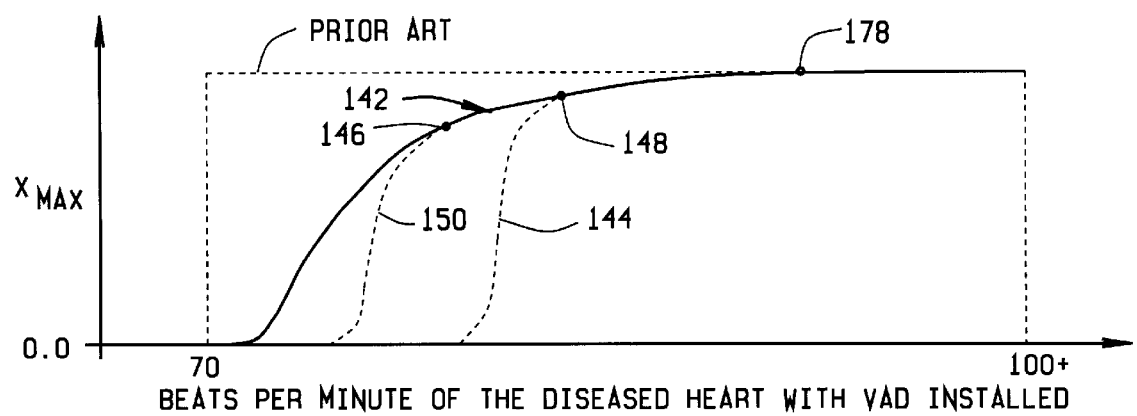
FIG. 16 is a graph illustrating the relationship between the travel of the piston of the present device and the residual cardiac output provided by the native diseased heart.

FIG. 16 is a concept illustration of the pumping travel of new BEEP system 35, as compared to that of known cardiac pumping devices. The abscissa is the number of beats per minute of the native heart. The ordinate is the length of travel of driving magnet 40 along the length of hydraulic pump 42. The known devices are either on or off (travel X is always equal to maximum travel Xmax), as shown by the dotted line. In the present device, the length of travel of driving magnet 40 along hydraulic pump 42 varies, following solid line 142, depending on the number of beats per minute of the native heart. As the number of beats per minute of the native heart increase, they reach high threshold dotted line 144 at which point controller 64 signals for driving magnet 40 to start moving along the length of hydraulic pump 42 smoothly increasing the stroke travel, approaching solid line 142.

Over time, due to augmentation of ejected volume by the VAD, the end diastolic volume of the native heart decreases. This allows the internal volume of the ventricle to become smaller, which subsequently allows the muscle of the native heart to begin to recover, and hence eject a greater volume of blood per stroke. As cardiac output is the product of ejected blood volume times heart rate, the increased ejected volume allows the heart rate to decrease. These changes are sensed by controller 64, which reduces the stroke length of the VAD as a greater portion of the cardiac output is now being supplied by the native heart. The stroke length of the VAD progresses to the left, from point 148 toward point 146. When the beats per minute reach the lower threshold point 146 (reflecting at least partial recovery of the native myocardium), this will cause a decrease in stroke length along line 150, which effectively reduces the stroke length of the VAD. If recovery of the native heart continues, the stroke volume of the L-VAD is reduced to zero along line 150. At this point the native heart is once again providing the total cardiac output on its own, without the assistance of the VAD. The shape of line 142 is actively manipulated by controller 64 using additional inputs for the measurement of the ejection volume and pressures of the right and left ventricles provided by the measurement system shown in FIG. 9 and described in relation thereto.

A critical factor in the success of a newly-installed L-VAD is satisfactory operation of the right ventricle during the immediate peri-operative period. The ejection fractions of the right and left ventricles are monitored by mechanisms such as those illustrated in FIG. 9 and alternative embodiments thereof. This allows the volumetric outputs of the right ventricle and the assisted left ventricle to be the same by manipulating the shape of line 142 up or down. For example, suppose that a short time after activation, the right ventricle is measured to give 50 cc per beat and the left ventricle gives 25 cc per beat. In this case, the stroke length of L-VAD 74 will be adjusted to give 25 cc per beat. If, a short time later, the right ventricle starts to fail and now only ejects 40 cc per beat (while the left ventricle still gives 25 cc per beat), this discrepancy in the ejection fractions will be detected by proximity sensors 406 and 416. In response, controller 64 will lower the level of line 142, resulting in a shorter stroke length of L-VAD 74, to give 15 cc per beat, for a total of 40 cc from the assisted left ventricle. The human body will compensate with a corresponding increase in heart rate (beats per minute). In this fashion, controller 64 matches the ejection volumes of the right and left sides. Should the right ventricle continue to fail, a decision will have to be made as to the appropriateness of installing an R-VAD, making this a BI-VAD system.

Assuming that a patient is supported on an L-VAD alone, the length of the pumping stroke of the L-VAD is determined as a function of beats per minute, as shown in FIG. 16, and manipulated by matching the ejection volumes of the left and right sides of the heart. For example, starting from point 148, if the beats per minute continue to increase, then the piston stroke also continues to increase smoothly to point 178. Starting from any operating point to the right of point 178, as beats per minute decrease, at point 178 the device reduces the travel of driving magnet 40 from its maximum travel along hydraulic pump 42. If the number of beats of the native heart is reduced sufficiently to reach low threshold line 150, then the travel of driving magnet 40 is reduced smoothly until it becomes zero following low threshold line 150. Lines 150 and 142 may coincide over the length of line 150. Line 142 to the left of point 146 in FIG. 16 can represent the initial activation of the L-VAD after surgical installation thereof.

The locations, magnitudes and exact shape of lines 142, 150 and 144 shown in FIG. 16 are for purposes of illustration and will vary from patient to patient, and device to device. In addition, during normal operation of the L-VAD, small up or down variations of the level of line 142 are made by controller 64 in order to match the ejection volumes, measured as described in FIG. 9, of the left and right sides of the system. The control algorithm has several input variables; among others, beats per minute measured by the ECG (as described below), the ejection volume and pressures from the right and left side of the system as illustrated in FIG. 9. For clarity, in the remaining Figures the concepts are illustrated using beats per minute to represent the function of controller 64.

Figure 17:
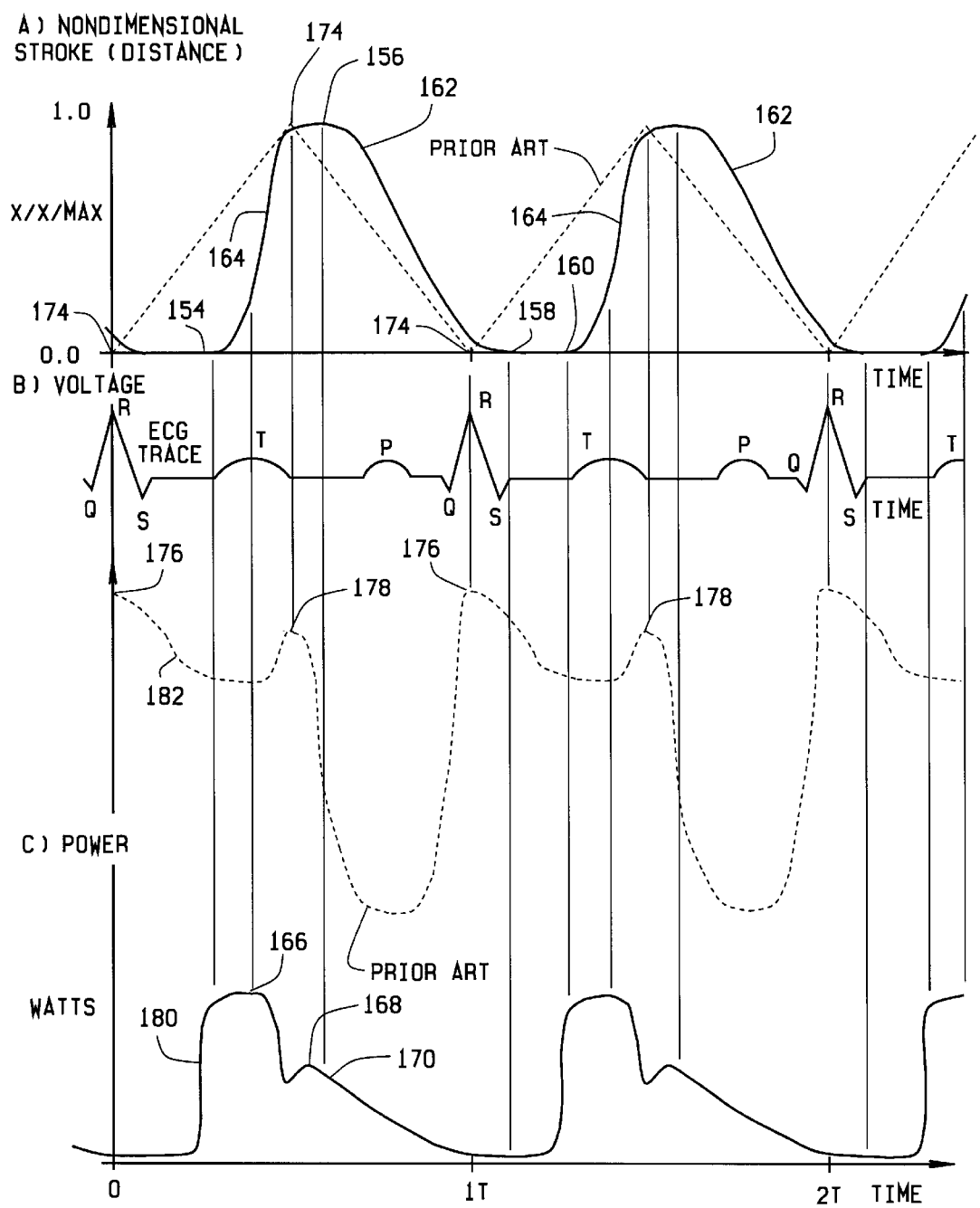
FIG. 17 is a series of graphs comparing the position and power requirements of a prior art pumping system and the present BEEP system with respect to a typical electro cardio gram (ECG) trace.

FIG. 17 is a chart comparing the activation sequence of the known Larson et al. device and that of the present BEEP system, as well as the corresponding power requirements, in relation to the ECG trace of the native heart. The solid lines represent the present device and the dotted liens represent the known device of Larson et al. The common abscissa is the time period required for two beats of the native heart. The ECG trace has characteristic spikes Q, R, S (commonly known as the QRS complex), and waves T and P, whose physiological function and importance is described in detail in medical texts. The beginning and end of the stroke of Larson's device occurs at or near point R of the QRS signal.

The graph shown in portion A of FIG. 17 shows non-dimensional stroke distance traveled by driving magnet 40 (X to Xmax) from 0.0 to 1.0, according to FIG. 16. Portion B of FIG. 17 illustrates a typical ECG voltage trace during cardiac operation. The beginning of the stroke of the present system is at or about the beginning of the T wave, allowing the rapid ejection phase of the native heart to precede the augmentation of the VAD. The pumping phase (points 154 to 156) of the present system occurs between the end of the T wave and the beginning of the P wave. The return stroke begins at this time point 156) and ends at or just after the QRS complex (point 158).

Driving magnet 40 rests at the center of electromagnetic coil 46 (X=0) during the time period between the end of the return stroke (point 158) and the beginning of a new stroke (point 160). The resting period between the end of the return stroke (point 158) and the beginning of the next stroke point 160 corresponding to 154) is important for a number of reasons. For example, acceleration at the beginning 154 and end 156 points of the stroke is minimal. This resting period allows time for depolarization of electromagnetic coils 46, 48 and 50 between strokes. When necessary, it also allows driving magnet 40 to be centered within electromagnetic coil 46, thereby allowing driven magnet 44 and valve seat magnet 54 to return to the beginning of the stroke of L-VAD 74. This return function is accomplished by opening and closing check valve 84, as necessary.

Due to leakage of hydraulic fluid around magnets 40 and 44 it is possible that one of the two magnets is stopped at one of the two ends of its travel while the other magnet is somewhere in the middle of its stroke. For example, if annular driven magnet 44 is at the end of its travel at the pump inlet (by the aortic valve as shown in FIG. 1) but driving magnet 40 is not yet all the way back to the beginning of its stroke (as shown in FIG. 4), then high hydraulic pressure will arise between driving magnet 40 and end cap 57. This condition would be sensed by the large increase in the power required by the coils. At that time the controller would open check valve 84 and would pull driving magnet 40 by the coils towards end cap 57, until it touches end cap 57, thus bringing the two magnets back into phase, and normal operation would resume. The procedure is similar if driving magnet 40 reaches the end of its pumping travel (as shown in FIG. 3) while driven magnet 44 is near the middle of its travel (as shown in FIG. 2). It is also possible to correct for these leakages at the end of every pumping stroke, or ever few pumping strokes. A similar procedure can be used for initial activation of the device, to start the device after it has been stopped, and to re-lock magnets 54 and 44 if they are not locked relative to each other at any time during operation. The latter condition is sensed by a large decrease in the power required by the coils.

The shape of line 164 in FIG. 17 (portion A) is determined by the optimization procedure described later herein. Acceleration begins smoothly (point 154 on line 164) so that less power is required than if the device started with a constant velocity. Maximum acceleration is achieved somewhere in the middle of the stroke, based on the optimization procedure. The VAD of the present system approaches maximum stroke travel with minimum velocity at point 156 so that it does not impact against the mechanical stop at the end of travel and no energy is lost due to impact. Thus, less energy is required to start the return stroke. The return stroke is less critical than the pumping stroke because one-way valve 70 is open and less energy is required to return the new VAD (e.g. L-VAD 74) to its starting position. Even so, the shape of line 162 is optimized by the procedure. Velocity is zero at X=Xmax, requiring less power than if there was a change in velocity at Xmax. The shape of lines 164 and 162, and resting period between points 158 and 160 is optimized by the procedure.

FIG. 17C shows the power requirements of the present device in Watts during usage. The maximum power requirement (point 166) occurs somewhere along line 164, as optimized by the procedure. During the return stroke, power peak at point 168 occurs slightly before X=Xmax at point 156, which corresponds to the power requirement at point 170. This occurs because of the sequence of energization of electromagnetic coils 46, 48, and 50 as explained further in FIG. 18.

In comparison, the known device, illustrated by the dotted lines in FIG. 17, begins the pumping stroke at or near R of the QRS complex, with constant velocity, until the point of maximum travel, which occurs at or near the end of the T wave. The return stroke is with constant velocity from the point of maximum travel until the R peak of the next QRS complex, requiring large acceleration at the two ends 172 and 174 of its stroke. This requires correspondingly large power input. In addition, the velocities are not optimized for the unsteady flow and the time varying magnetic fluxes, requiring large power input at all points during the stroke. Points 172 and 174 correspond to power peaks 176 and 178, respectively. As a result, the present device will take less power (solid line 180) than the prior art device (dotted line 182), and the peaks occur at different times.

Further with reference to FIG. 17, power peak 166 of the present device occurs during the T wave of the native heart, allowing the native heart to finish its rapid ejection. This increases the volume of blood pumped due to the combination of the native heart and the VAD with respect to the prior art (due to summation of volume), requires less power than the prior art device, and allows the native heart a chance to recover by decreasing left ventricular volume. These combinations make the BEEP system bio-compatible.

Figure 18:
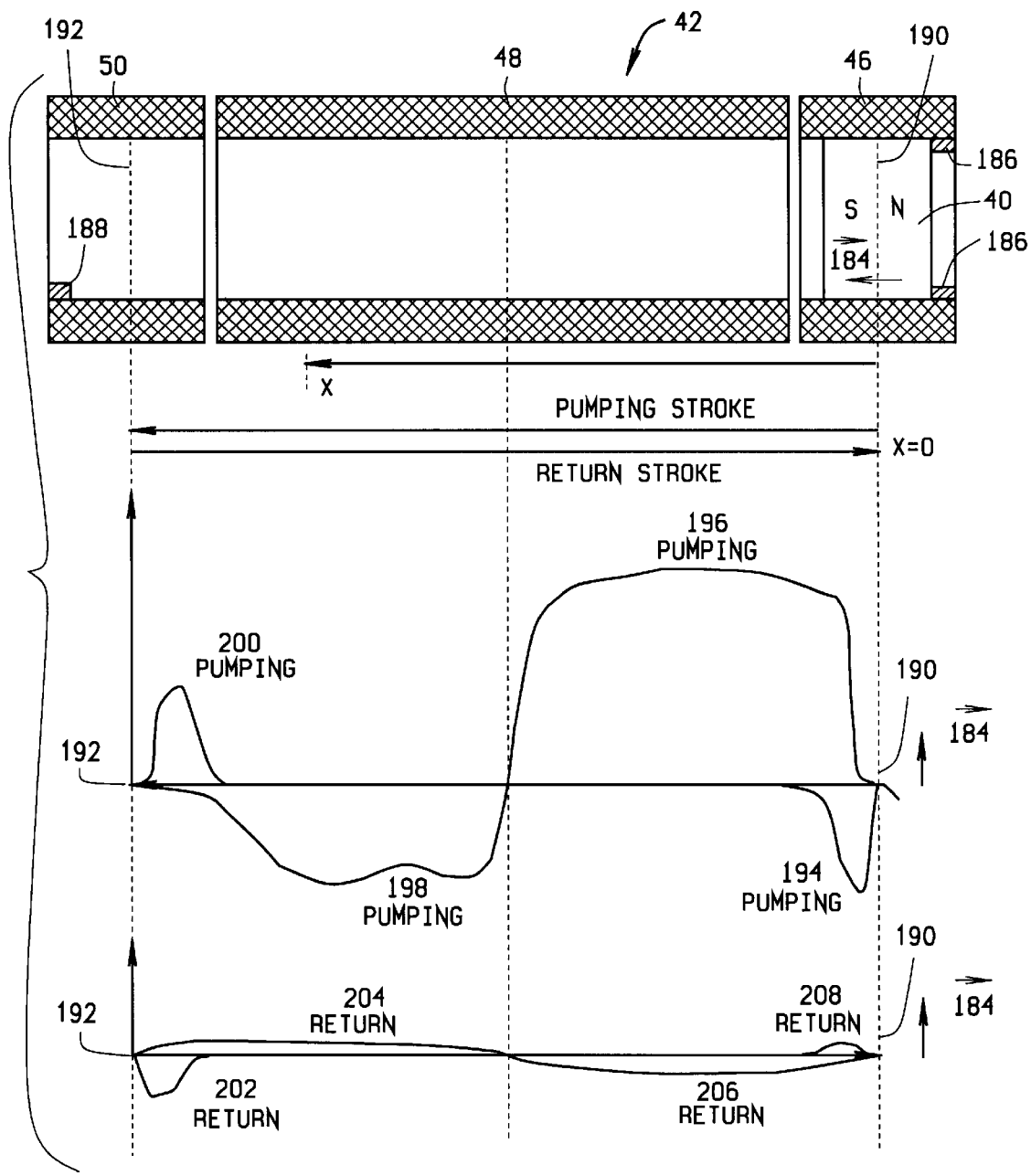
FIG. 18 illustrates the location of three coils of one embodiment of the BEEP system and the corresponding current flow sequence in the coils.

FIG. 18 is a schematic illustration of the embodiment of BEEP system 35 shown in FIG. 1, using three electromagnetic coils 46, 48 and 50 along the length of hydraulic pump 42 showing the corresponding magnetic flux of the driving magnet and the electromagnetic coils. Vector 184 represents the magnetic flux of driving magnet 40. Position X=0 is at the center of electromagnetic coil 46. Position X/Xmax is at the center of electromagnetic coil 50. The top portion of the Figure shows electromagnetic coils 46, 48 and 50 and positive stops 186 and 188. The middle portion of the Figure is an illustration of the typical periodic representation of the magnetic fluxes of electromagnetic coils 46, 48 and 50 during the pumping stroke from X=0 to X=Xmax. The bottom portion of the Figure is an illustration of the typical periodic representation of the magnetic fluxes of electromagnetic coils 46, 48 and 50 during the return stroke from X=Xmax to X=0.

With reference to the middle portion of FIG. 18, the abscissa is the axial position of driving magnet 40 from the center of coil 46 (point 190) to the center of electromagnetic coil 50 at X=Xmax (point 192).

With reference to the bottom portion of FIG. 18, the abscissa is axial position of driving magnet 40 from the center of coil 50 at X=Xmax (point 192) to the center of electromagnetic coil 46 at X=0 (point 190). Starting from X=0 in FIG. 18(*b*) (point 190, which corresponds to point 154 in FIG. 17), positive stop 186 ensures that activation of magnetic fields 194 and 196 in electromagnetic coils 46 and 48, respectively, will force driving magnet 40 from the center of electromagnetic coil 46 towards the center of electromagnetic coil 48. Magnetic field 194 is reduced to zero soon after driving magnet 40 is a little outside electromagnetic coil 46. As driving magnet 40 approaches the center of coil 48, magnetic field 196 in coil 48 is reversed in direction to magnetic field 198. The reversal in magnetic field 196 does not necessarily coincide with the point in time when magnet 40 is at the center of coil 48. The exact location of reversal is dependent upon an optimization procedure.

Magnetic field 200 is initiated just before driving magnet 40 enters electromagnetic coil 50. The combination of magnetic fields 198 and 200 die out by point 192 (corresponding to point 156 in FIG. 17) and smoothly bring the magnet to position X=Xmax, against positive stop 188. At that position, the magnetic fields in coils 48 and 50 are reversed as shown at point 192 in FIG. 18(*c*). Positive stop 188 ensures that magnetic fields 202 and 204 from coils 50 and 48, respectively, push driving magnet 40 from X=Xmax (point 192) towards the center of coil 48. Magnetic field 202 is reduced to zero soon after driving magnet 40 is a little outside electromagnetic coil 50. As driving magnet 40 approaches the center of coil 48, magnetic field 204 in coil 48 is reversed in direction to magnetic field 206. The reversal in magnetic field 204 does not necessarily coincide with the center of coil 48.

The exact location of reversal is dependent upon the optimization procedure. Magnetic field 208 is initiated just before driving magnet 40 enters electromagnetic coil 46. The combination of magnetic fields 206 and 208 die out by point 190 (corresponding to point 158 in FIG. 17) and smoothly bring the magnet to position X=0, against positive stop 186. At that position, from point 158 to point 160 in FIG. 17, magnetic field 208 (or its residual effects) will retain driving magnet 40 at X=0, whereupon the cycle repeats itself. All of the magnetic fields 194–208 will be optimized to give $F_{vad}\{t\}$. The power to obtain magnetic fields 196–208 will be minimized based on the resistance, inductance, and capacitance of the electromagnetic system, including the coils and magnets, and voltage source, using constitutive relations or experimental data for the dynamic representation of the systems in equation (7), established in electromagnetic theory.

In general, the magnitudes of magnetic fields 194–200 will be greater than those of magnetic fields 202–208, because the former occur during the pumping phase with one-way valve 70 closed and pushing blood, while the latter occur during the return stroke with one-way valve 70 open. Even though the above embodiment utilizes three electromagnetic coils, it is contemplated that the present device may contain more or fewer electromagnetic coils. In the limit, a linear stepper motor may be used.

FIG. 19 is a schematic illustration of the embodiment of Beep System 35 illustrated in FIG. 1, wherein only two electromagnetic coils 46 and 48 are activated and used to move driving magnet 40. This is done in order to obtain some stroke length X less than Xmax, as shown in FIG. 16. Similar relative functioning, as described with respect to FIG. 18, is found in the displacements and magnetic fluxes of FIG. 19 as well.

FIG. 20 is a concept illustration of the human heart depicting the placement of R-VAD 58 in place of a portion of the pulmonary trunk 210. Blood moves from right ventricle 106 through pulmonary valve 94 and into the pulmonary trunk 210 before its bifurcation point 212.

FIG. 21 shows the placement of an R-VAD embodiment of BEEP system 35 within the human torso O. The illustration depicts the spatial relationship between battery battery/controller assembly 65, hydraulic pump 42, and R-VAD 58. As mentioned previously, FIGS. 7, 9–13 and 20, 22, 24 and 27 are simple arrangement illustrations, not anatomically-correct views.

Figure 22:
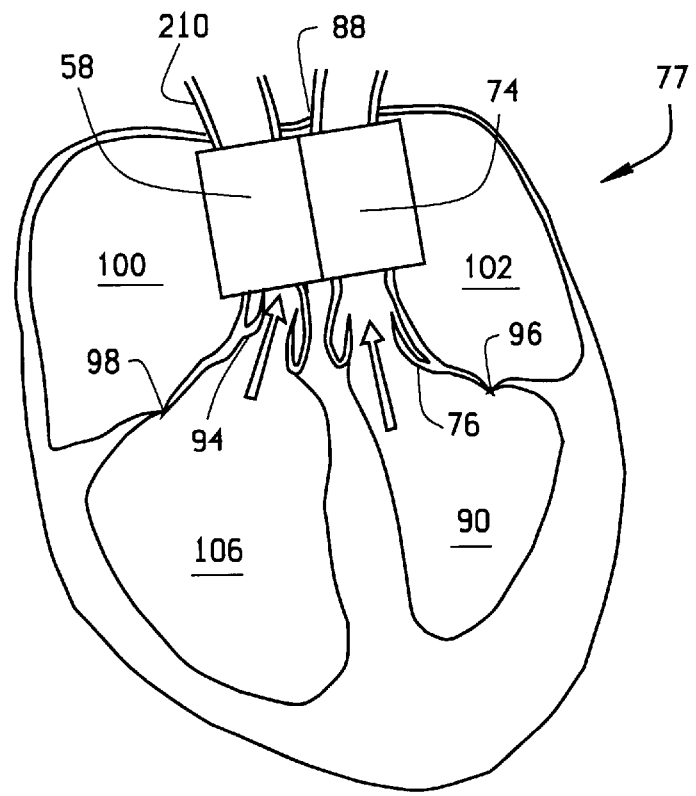
FIG. 22 is a concept illustration of the human heart illustrating the location of a bi-ventricular-assist device (BI-VAD) embodiment of the BEEP system.

FIG. 22 shows the placement of a BI-VAD, generally designated 77, which consists of a combined assembly of L-VAD 74 and R-VAD 58 in the same system. In this embodiment L-VAD 74 is located in place of at least part of the ascending aorta 88. In use of BI-VAD 77 blood moves from left ventricle 90 through the aortic valve 76 and into ascending aorta 88; i.e. in this system L-VAD 74 pumps blood into the aortic arch 80, just as in use of the L-VAD alone. R-VAD 58, as part of the BI-VAD 77, is located in place of at least part of the pulmonary trunk 210, just as it is used in the embodiment (R-VAD alone) shown in FIG. 20. Blood moves from the right ventricle 106 through pulmonary valve 94 and into pulmonary trunk 210 as R-VAD 58 portion of BI-VAD 77 pumps blood into the bifurcation 212 (hidden from view) of the pulmonary arteries.

Figure 23:
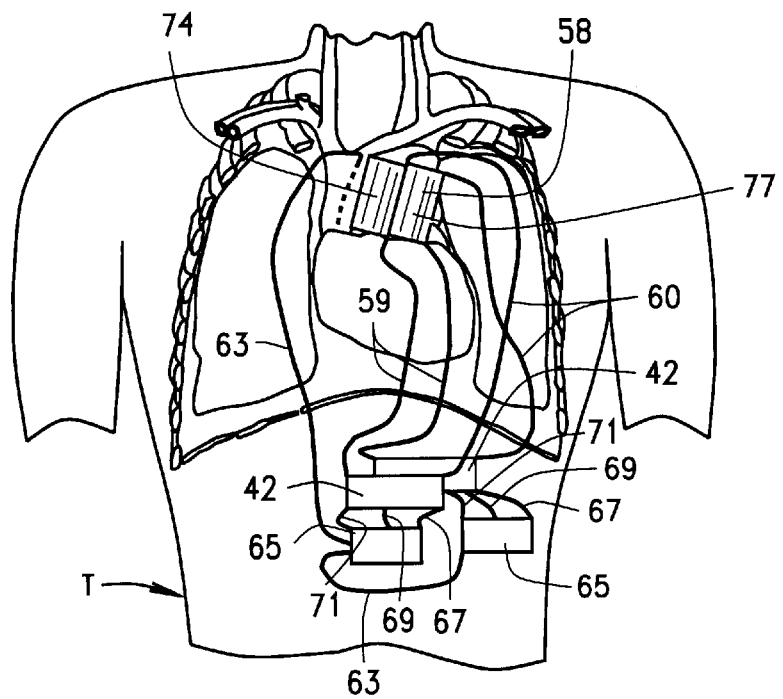
FIG. 23 a schematic view of the human torso illustrating the location of the main components of a BI-VAD embodiment of a BEEP system in the human body.

FIG. 23 shows the general placement of the BI-VAD 77 embodiment of the BEEP system in the human torso O. The illustration depicts the relative spatial relationship of BI-VAD 77 in the chest and of battery/controller assembly 65 and hydraulic pump 42 in the abdomen. (The LVAD in FIG. 23 is correctly shown more to the right of the patient's chest than RVAD, but FIG. 23 is anatomically correct, while FIG. 22 is a simple arrangement illustration).

Figure 24:
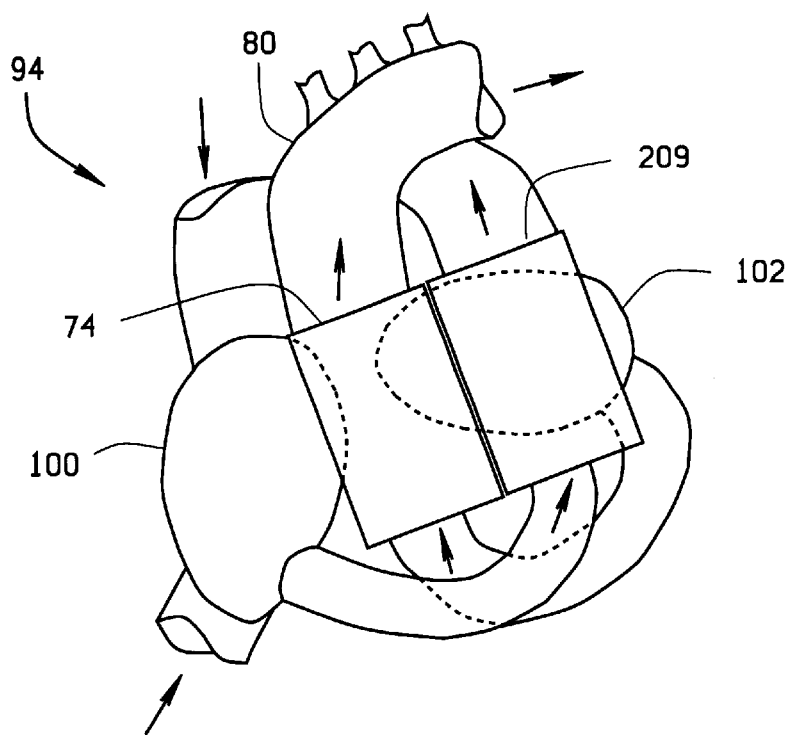
FIG. 24 is a concept illustration of a total artificial heart (TAH) embodiment of the BEEP system.

FIG. 24 is a schematic illustration of the Total Artificial Heart (TAH) embodiment, generally designated 95, for use in a variation of the new BEEP system 35. In this TAH embodiment, atria 100 and 102, along with ECG signal 66, are retained from the native heart. The TAH is comprised of a BI-VAD system with a greater stroke volume than the assist embodiment, as the total cardiac output is now being supplied by the BEEP system. In some TAH embodiments it is possible to use the mitral valve 96 and tricuspid valve 98, shown in previous Figures, provided their papillary muscles and chordae tendineae are functioning, and insert he L-VAD and/or R-VAD portions of the BI-VAD into the respective ventricles. However, in other alternative TAH embodiments artificial valves may be necessary or preferred. In addition, all, some or non of the native ventricle may be retained. In the embodiment illustrated in FIG. 24 L-VAD 74 completely takes the place of left ventricle 90 (seen in FIG. 7, for example), and hence its inlet is grafted to an artificial valve (not shown) and its outlet is grafted into the ascending aorta 88. Right ventricle 106 is replaced with an R-VAD 58, which has its inlet grafted to an artificial heart valve (not shown) and its outlet grafted into the pulmonary trunk 210.

Figure 25:
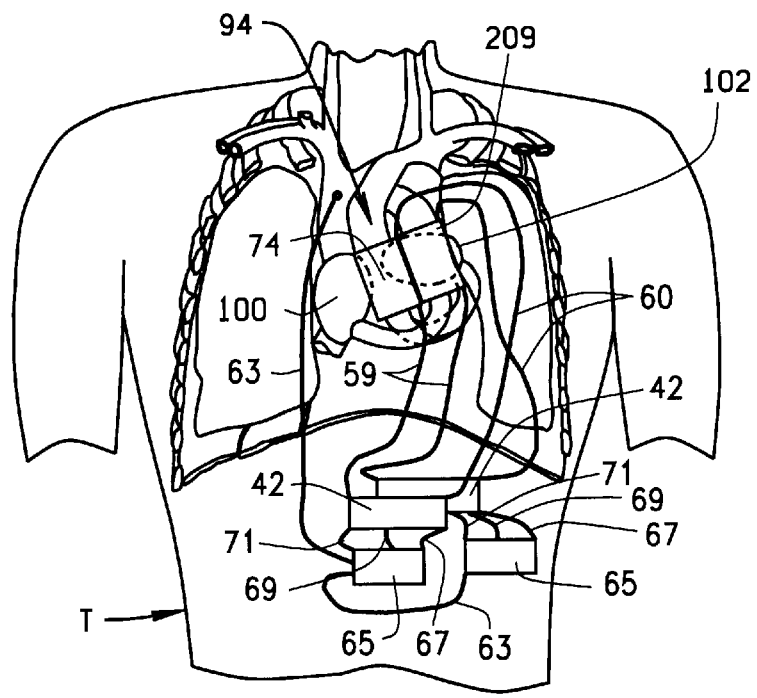
FIG. 25 a schematic view of the human torso illustrating the location of the main components of a TAH embodiment of a BEEP system in the human body

FIG. 25 shows the general placement of the TAH embodiment 95 of the new BEEP system within a human torso O. The illustration depicts the spatial relationship among battery 62, controller 64, in the abdomen, and TAH 95, in the chest cavity. In various embodiments of the TAH a portion or all of the native heart may be removed. If the chordae tendinae and papillary muscles are intact, then the TAH would consist of an LVAD and an RVAD placed inside the respective ventricles. If the mitral and tricuspid valves of the native heart are not utilized, then the TAH would require a one-way valve at the inlet of the LVAD and a one-way valve at the inlet of the RVAD, and the combination that would make the overall TAH. If the entire native heart (including the sino-atrial node) is removed, then the LVAD and RVAD system that would comprise the TAH will be triggered by an electrical signal driven by sensors that indicate the level of oxygen in the blood stream and other sensors of body functions.

Figure 26:
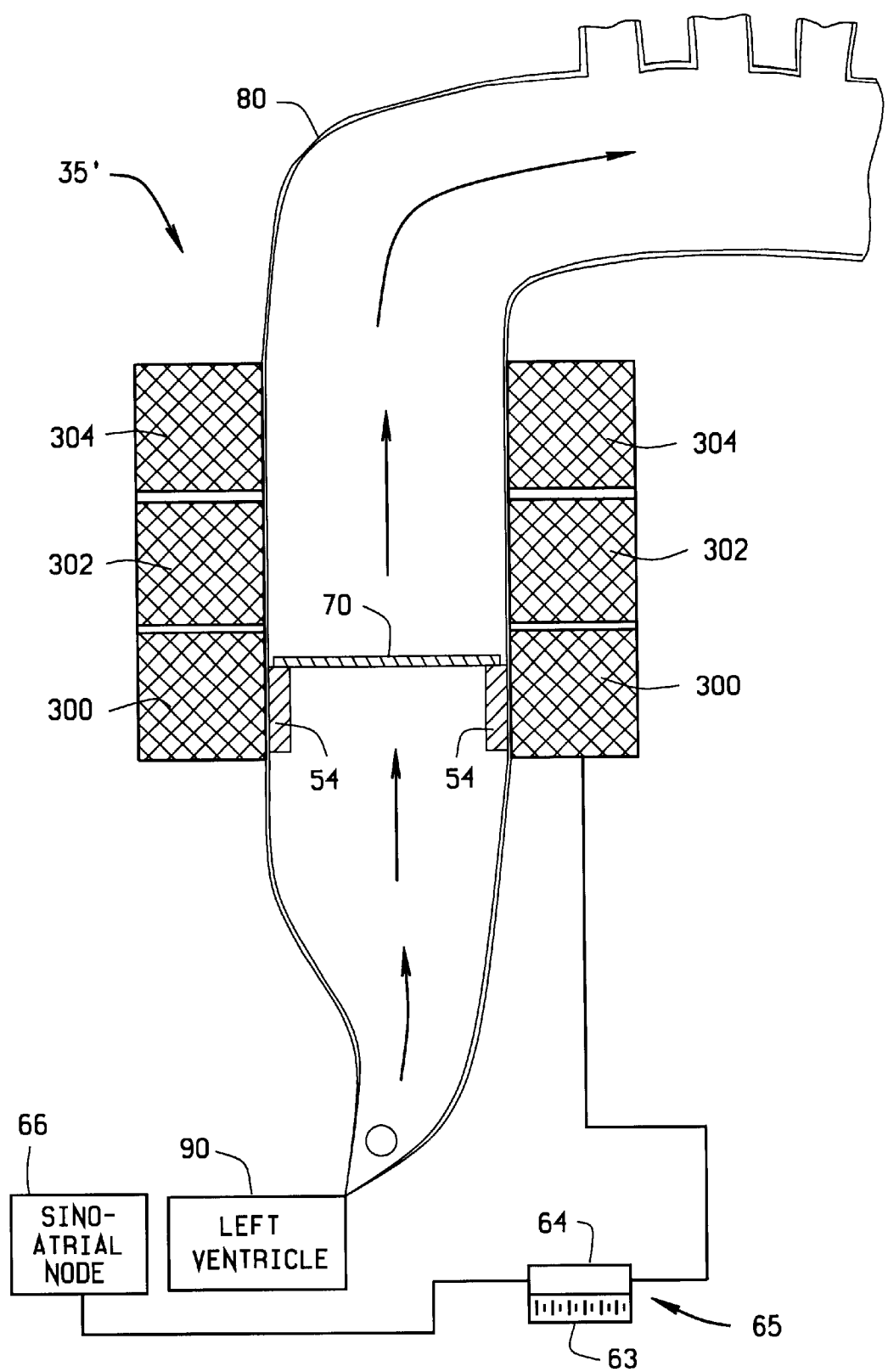
FIG. 26 is a schematic view generally identifying an alternative-component configuration of an L-VAD embodiment of a BEEP system.

FIG. 26 represents an alternative embodiment, generally designated 35', of an L-VAD version of BEEP system 35. In this version, two or more electromagnetic coils, 300, 302 and 304 are used to drive valve seat magnet 54 in a reciprocal fashion. In this alternative embodiment, no hydraulic pump is required. The Figure represents the beginning of the pumping stroke, at which time one-way valve 70 is closed and electromagnetic coils 300, 302 and 304 are energized in a manner similar to that illustrated in FIG. 18b or 19b to drive valve seat magnet 54 down the length of L-VAD 306, pumping blood into aortic arch 80. At the end of the pumping phase, the direction of current in electromagnetic coils 300, 302 and 304 is changed, again in a manner similar to that depicted in FIG. 18c or 19c, driving valve seat magnet 54 (this time with one-way valve 70 open) back down the length of L-VAD 306 to its original position. Electromagnetic coils 300, 302 and 304 are energized by controller 64, in response to the ECG signal 66, and the ejection volumes and pressures of the right and left sides of the system as illustrated in FIG. 9, in a similar manner as described in the preferred embodiment.

Figure 27:
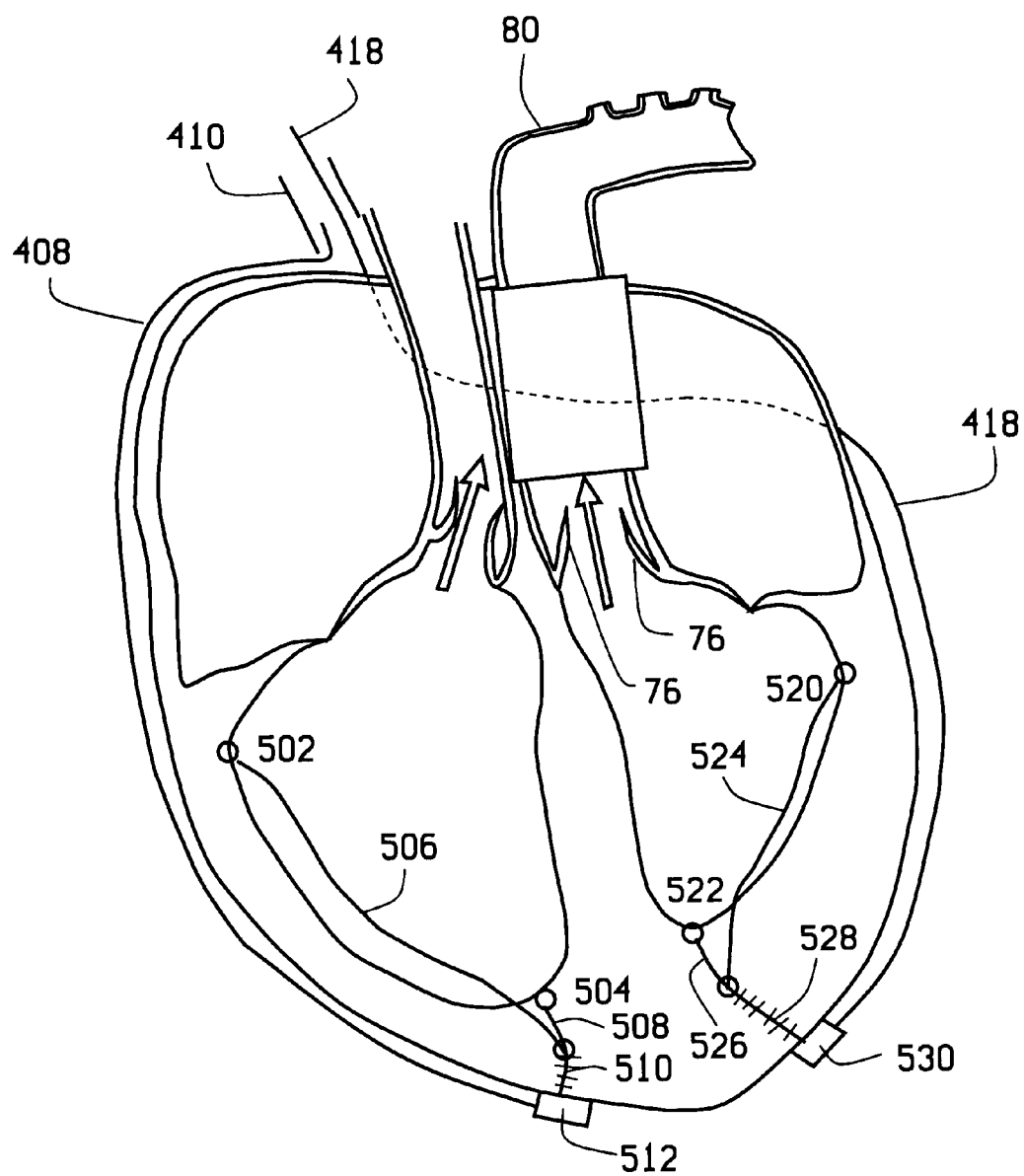
FIG. 27 is a concept illustration of the human heart illustrating the design and location of an alternative ejection volume measuring apparatus.

FIG. 27 represents an alternative embodiment of the ejection volume measuring apparatus for use in an alternative BEEP system, generally designated 35" (only a portion of which is shown). In embodiment 35", instead of rare earth magnets 402, 404, 412, and 414 (shown in FIG. 9), any proximity sensor 502, 504, 520 and 522, can be substituted. Such proximity sensors may be included in any or all of the four chambers of the heart. These proximity sensors may or may not need to be coupled with conductors 506, 508, 524, and 526. Proximity sensor output can be fed to signal converters 512 and 530 directly, or with conductors 510 and 528. The output from signal converter 512 is directed with lead 408 into wire bundle 410, and the output from signal converter 530 is directed with lead 418, also into wire bundle 410. Wire bundle 410 can, but does not necessarily, include inside it conductor 63, shown in FIGS. 1–4, which transmits the ECG signal to controller 64. The signals from these conductors become inputs to controller 64.

Optimization Procedure and Control Sequence:

The following optimization process can be applied to any VAD or TAH device. During normal operation the native heart interacts with the VAD so that the overall system/control responds to X/Xmax, the ECG signal, and φ of the combined system of the native heart and VAD.

FIGS. 28–34 illustrate the basic procedure of the optimization and control process for new BEEP system 35, 35' or 35". It is to be understood throughout the discussion herein that, unless otherwise specified, "VAD" shall be interpreted to mean either the L-VAD, R-VAD, BI-VAD or TAH.

The main steps of the process are the following:
  (a) Develop a mathematical model of the dynamic behavior of the desired part of the physical system
  (b) Identify the system inputs, outputs and desired constraints for the physical part of the system in (a) above
  (c) Optimize power input to the VAD to complement the action of the diseased native heart
  (d) Develop an optimized control scheme for the inputs and outputs
  (e) Perform tests on the individual patient
  (f) Maintenance: updating the dynamic optimization and control schemes as the condition of the patient changes with time.

The inlet and outlet boundary conditions, and other engineering inputs to the model, and corresponding dynamic inputs, will depend on the dynamic system definition (Gyftopoulos and Beretta, 1991). Several alternative embodiments of the definition of the dynamic system that will perform the optimization can be defined, and the following examples are given to illustrate the flexibility and potential of the power optimization method and control optimization method.

Figure 28:
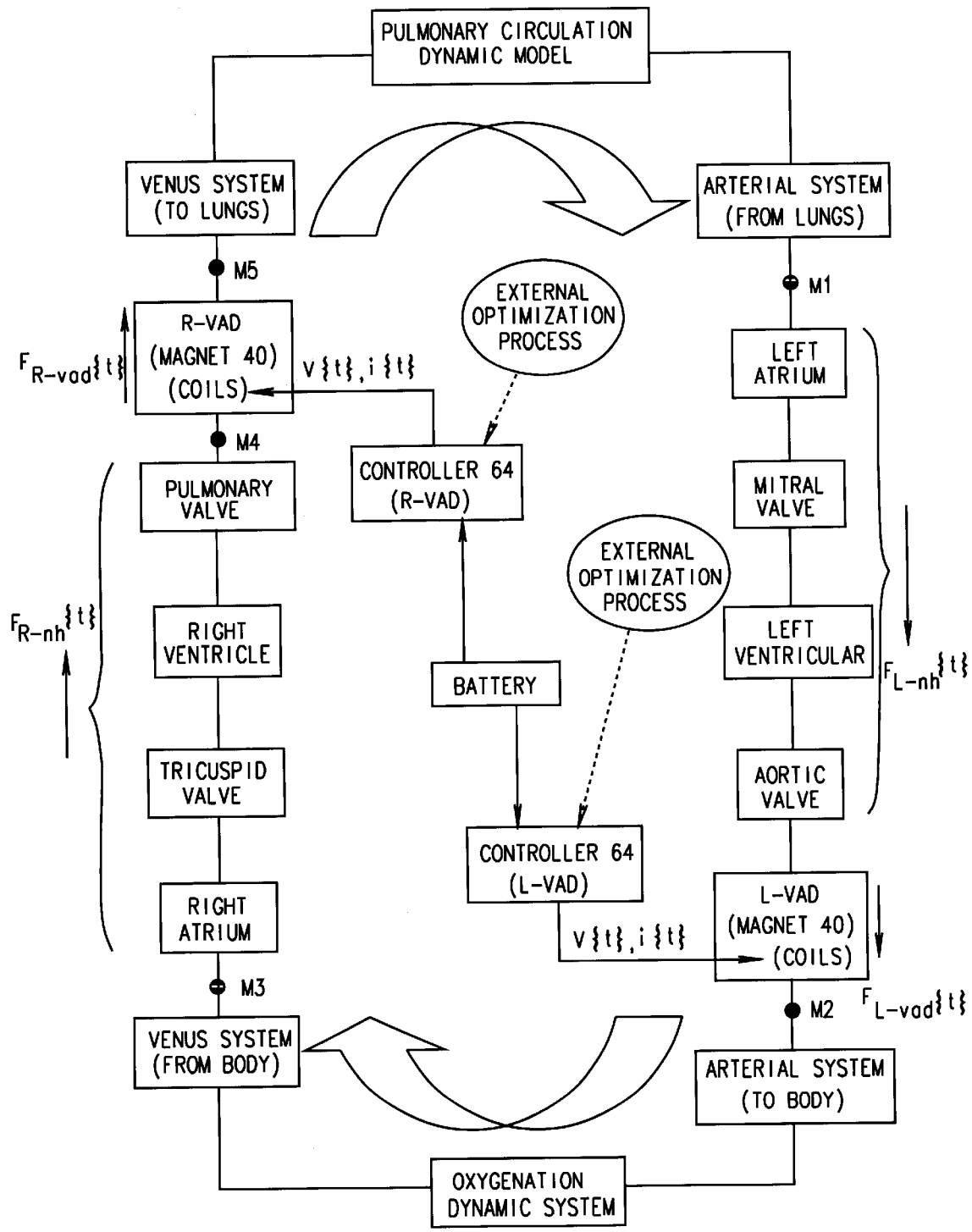
FIG. 28 is a diagrammatic illustration of the main components of the circulation system in the BI-VAD embodiment.

FIG. 28 illustrates the main components of the circulation system with the main BI-VAD components in place, with the right and left side forcing functions from the native heart and the VAD. The level of detail of system components shown in FIG. 28 is for illustration purposes only, and several alternative models with more or fewer details of system components can be drawn. One could choose to obtain the dynamic response of the whole system, including theoretical, numerical or experimental models for the pulmonary system (lungs) and oxygenation dynamic systems. A continuous model (differential equations expressing the dynamic response at any position and time of the component) for all components of the system would be of enormous complexity, though still theoretically possible. Continuous models can also lead to distributed parameter analyses. With current (2001) technology those skilled in the art would likely (and straining computational resources) choose to model: the L-VAD system from points M1 to M2; the "right side" of the heart system from points M3 to M4 without R-VAD; and from M3 to M5 with the R-VAD. These M1 to M5 points (or other similar points that may be used for the optimization) are used to separate suitable portions of the physical system in order to develop a dynamic model of portions of the system rather than the whole system shown in FIG. 28. Points such as M1 to M5 (or other similar points) used in order to simplify the model, may represent physical cross-sections of the flow passages, usually in the main blood vessels. Those with ordinary skill in the art may choose to develop the dynamic model using combinations of:
  (a) discretized finite element method programs (FEM, for example Szabo and Babuska, 1991; Bathe, 1995). For example, FEM models may be used for the cardiac muscle, for structural mechanical components, and other components;
  (b) computational fluid dynamics models (CFD, for example Anderson et al., 1984; Kiris et al., 1997). For example, CFD models may be used for the blood and hydraulic fluid flows, and other components of the system;

(c) analytic solutions for some dynamic elements. For example, analytic models may be used for some of the fluid leakage in narrow passages, using lubrication theory, and other boundary-layer techniques. Samples of such methods for different sub-components of the system are presented by (Nichols and O'Rourke, 1998; Panton, 1984; White, 1991; Schlichting, 1979; Hinze, 1987);

(d) specialized information for select parts of the cardiovascular system. For example, select such models are described by (Fung, 1984; Braunwald, 1984; Verdonck, 2000; Peskin and McQueen, 1997);

(e) lumped parameter models for some of the dynamic components. For example, some of the mechanical components may be represented with techniques described by (Meirovich, 1975); and (f) experimental data (which are usually the most reliable models) can be used for any aspect of the dynamic components of the system.

Thus the overall dynamic model can be based on continuum mechanics (or their variant of distributed parameter models), can be discretized, can be based on lumped parameters, rely on experimental data, or any combination thereof. Some of the component models will be linear, others will be non-linear, and some will be discrete or piecewise continuous (for example valve 70 is sometimes open, sometimes closed, and sometimes in the process of opening or closing). The overall dynamic model is likely to be complex, requiring significant computational resources. In alternative embodiments useful information can also be derived from simpler piecewise-continuous lumped-parameter non-linear dynamic models for the main components. For example, such extremely simplified models can consist of several masses, springs and dampers for each of the main components shown in FIG. 28, so that the overall dynamic model could be run on a conventional desktop personal computer.

Figure 29:
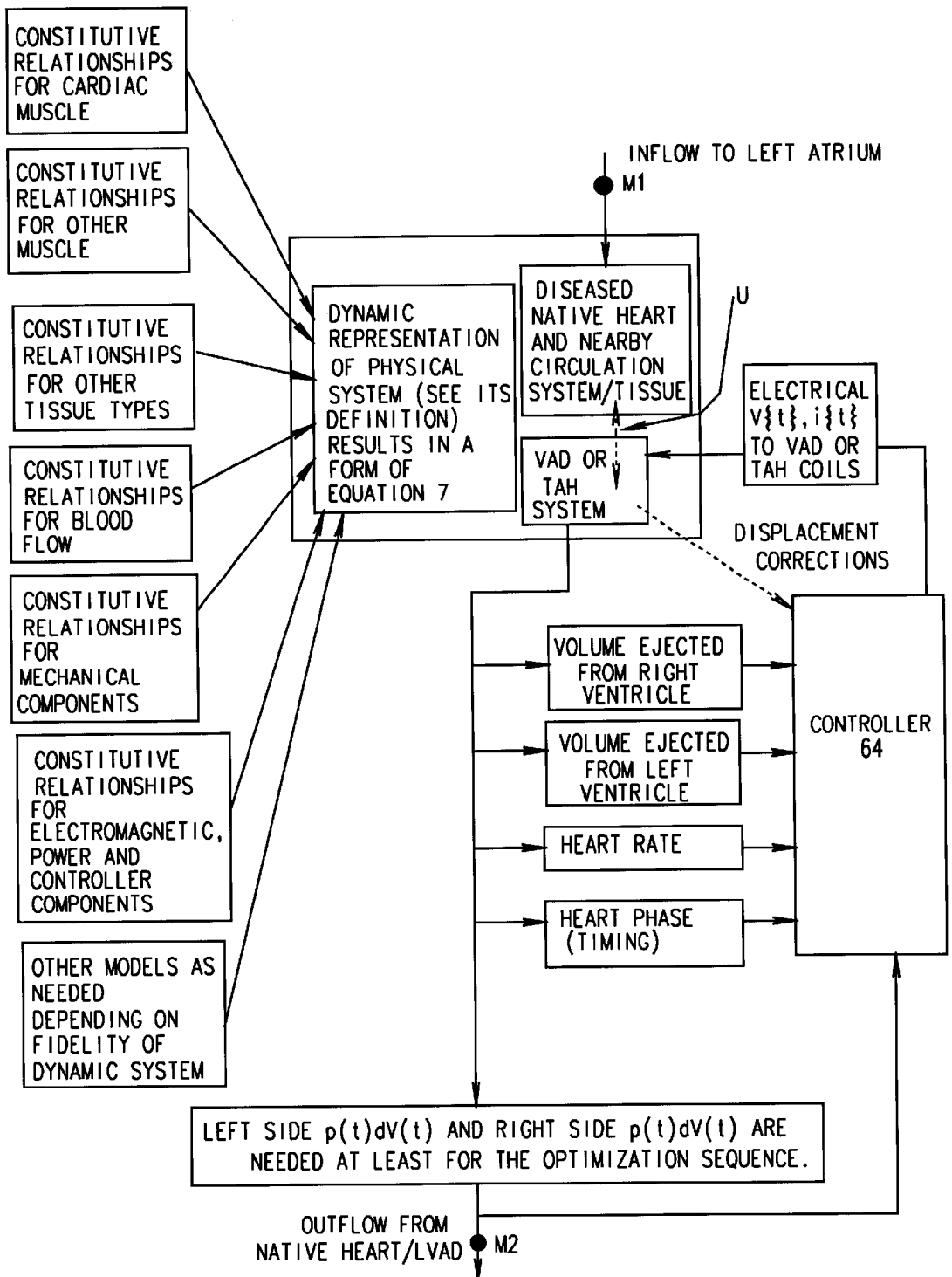
FIG. 29 is a flow chart schematically illustrating the development of the mathematical model (equations 7 and 8) for the dynamic system including the new VAD, in this case the L-VAD.

Once a suitable part of the physical prototype has been defined with points such as M1 to M5 for development of the dynamic model, the suitable inputs, outputs, boundary conditions, and other system constraints must be carefully defined (this is referring to the correct system definition, mentioned above). FIG. 29 is an example of one possible dynamic-system representation of the main components of the left side of the diseased native heart plus the L-VAD. Alternative embodiments of the model may include portions of the right side of the native heart and/or the R-VAD. If the sample model for FIG. 29 extends between points Ml and M2 in FIG. 28, then inlet and outlet boundary conditions would involve combinations of blood pressures and velocities at M1 and M2 as functions of time. In FIG. 29 the center diagram illustrates the dynamic model of the physical system. The dynamic model can be developed with experimental data or with equations or a combination thereof. There are two basic physical components to the center block of FIG. 29. One physical component is the diseased native heart and surrounding tissue to the native heart; and the other physical component is the VAD or BI-VAD or TAH system. The two physical components interact and dynamically affect each other during normal operation as shown by the dashed line R. The combination of the two main components of the system, whether presented mathematically or with experimental data, results in a dynamic representation of the physical system from M1 to M2 that can be described by a form of equation (7). The engineering definitions of the thermodynamic system (dynamic, thermodynamic, fluid dynamic, mechanical, etc., as discussed earlier) are crucial to the analysis and must be such that the patient's tissue surrounding both the native heart and the VAD or TAH are sufficiently removed from the components so that the dynamic operation does not affect the boundary surface that separates the dynamic system from the surrounding tissue. This is an imaginary boundary surface typical of the boundary surfaces in thermofluid dynamics texts that define the boundary of the engineering system being analyzed. The input for the dynamic representation of subsystems and components (shown on the left side of FIG. 29) can come from different sources. Some of the input can be experimental data, which is usually the preferred source of data, but other input can come from other adequate mathematical representations. Such inputs may come from the constitutive relationships of cardiac muscle or other muscle, or of the surrounding tissue, or the constitutive relationships for blood flow, whether it is modeled as Newtonian or non-Newtonian, incompressible or compressible. Several illustrations of these models are published in the above references. The mathematical representation of the physical system depicted in FIG. 29 from M1 to M2 can use constitutive relationships for the mechanical components, or constitutive relationships for electromagnetic components, or experimental data, or any combination thereof, or experimental data and mathematical expressions of constitutive relations, as shown on the left side of FIG. 29.

Other components of the physical system can also be incorporated, as needed, depending upon how many or how few of the system components are used in the dynamic model represented by the final form of "process equations" (7) and (8). The level of detail of the dynamic model will affect the complexity of the required solution. It will also affect the fidelity and thus accuracy of the results. In general, the higher the complexity and the fidelity the more accurate the results, but at some point there is a limit; i.e., a point of diminishing returns, where the increased complexity does not justify the higher accuracy. A judgment must be made on the fidelity of the dynamic model required for the particular application of the invention. The final decision on this issue will also depend on the sophistication of engineering tools available, (CFD, FEM etc) and the level of accuracy required of the results.

There are several alternative types of controllers suitable for the application. In the simplest case the controllers may give constant (battery) voltage, and vary the currents as a function of time to the three coils of FIG. 18 (for example $i_1\{t\}$, $i_2\{t\}$ and $i_3\{t\}$). Other controllers may give constant current but varying voltages. Other controllers may vary both the voltage and the current. The latter is the most likely embodiment. The third solution is likely to give the least power required than the other two controllers, as the electrical resistance, inductance and impedance of the coils, driving magnet 40, and surrounding ferromagnetic material impose non-linear effects on the unsteady flows of voltage and current, and the third type of controller allows one to take full advantage of the "natural frequencies" of the dynamic magnetic system in relation to the forcing function required by the patient-VAD system.

Figure 30:
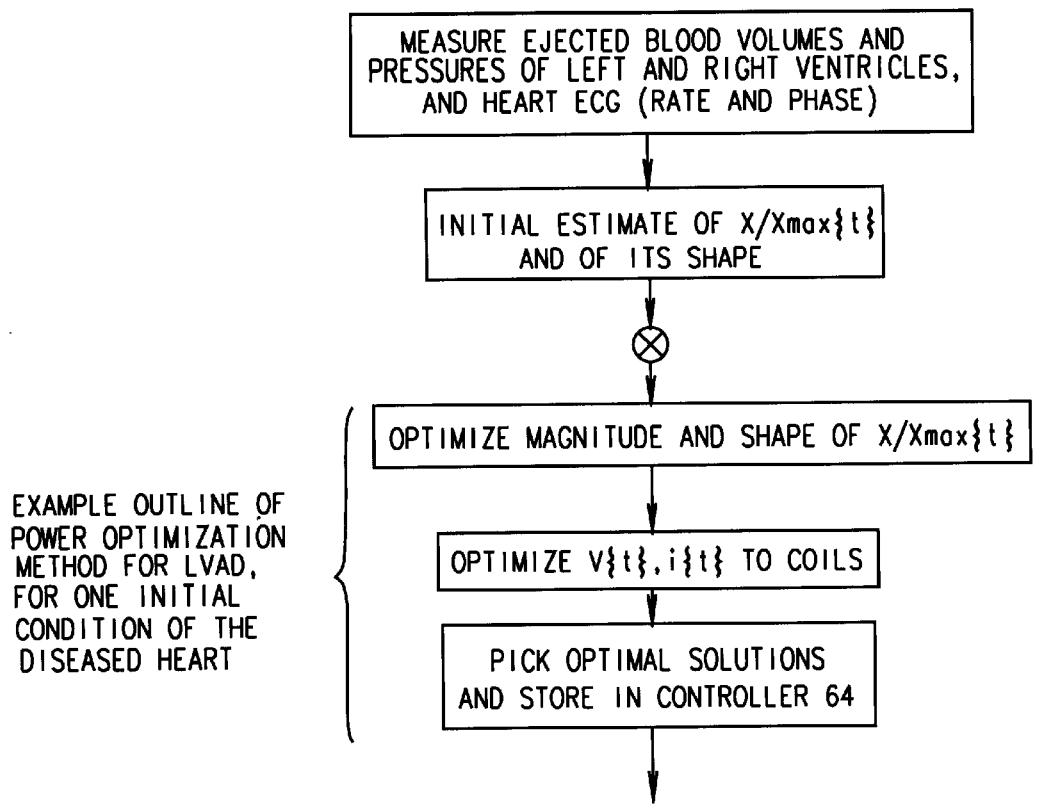
FIG. 30 is a flow chart schematically illustrating application of the power optimization process in a system including the new ventricular assist device (VAD), in this case the L-VAD.

The dynamic model developed above is used in the power optimization method, an example of which is illustrated in FIG. 30. The purpose of this optimization method is to minimize power requirements and maximize battery life between recharges. This is accomplished by identifying the minimum electrical power required to the coils for each operating condition of the VAD. Since the diseased native heart and VAD affect each other's dynamic performance (broken line U in FIG. 29), the optimization process must be repeated separately for each initial operating condition of the unaided native heart. The inputs for the specific illustration example are the initial condition of the diseased native heart, comprised of the ECG trace and the ejected blood volumes and pressures of the right and left side (atria and ventricles) as functions of time over the period of the heart rate. In one embodiment of the optimization process an intermediate output of the power optimization method is X/Xmax{t} and $F_{vad}\{t\}$ of the R-VAD and L-VAD. In an alternative embodiment of the optimization process the output is the voltage and current fed to each coil as a function of time as shown in FIG. 30. This optimization process must be repeated for each initial condition of the diseased native heart identified above.

One or more of the several potential optimal solutions V{t} and i{t} are stored in controller 64. The choice of optimal solution to insert in the controller is illustrated with an example below.

The example power optimization method of FIG. 30 searches for shapes of X/Xmax{t} that require the minimum power. In one example embodiment of this optimization process, the ejection volume of the native left ventricle is evaluated using MRI, echocardiography, or other similar techniques such as correlation with the movement of proximity sensors as described earlier. The desired additional volume that must be provided by L-VAD 74 is evaluated by methods illustrated in the earlier table of potential sizes of VAD. This dictates the required travel X/Xmax of L-VAD 74 in FIG. 16. Next, an initial estimate for the trace of line 162 in FIG. 17 (starting with an initial shape resembling that of line 162) is input into the power optimization method. This line shape may also be modeled with Fourier series analysis, and the amplitudes and phases in these Fourier series have a phase difference from the ECG trace of the native heart in $F_{nh}\{t\}$. One measure of these phases is graphically reflected in the phase difference φ from the phase of R in the QRS complex (phase zero) to point 154 in the trace of X/Xmax in FIG. 17.

This concept is commonly referred to as "phase" in dynamic systems. The pressures of the four chambers as functions of time are required at least for the optimization sequence, and it may also be required during the normal running of the device. However, the pressures and the volumes can also be correlated by other means in normal running of the device (for examples the ECG signal alone, or the ECG signal plus volume traces, or ECG signal plus volume plus pressure traces).

The forcing function of the native heart can be measured (for example with measurements of ventricular and atrial pressures and volumes, or their correlations) as described elsewhere in the text. The forcing function of the VAD is an input to the optimization process as described below. There are several alternative combinations of specifying this forcing function as an input to the optimization process. For example, one way is to prescribe the displacement X/Xmax of driving magnet 40 as a function of time, (FIGS. 16 and 17), evaluate the required force on driving magnet 40 from the coils, and then evaluate the electrical power required from the controller (voltages and/or currents to the coils) to accomplish this motion. This is further elaborated below. Then in an iterative process the displacement versus time (of driving magnet 40) can be changed until the electrical power to the coils is minimized while the displacement of driving magnet 40 provides corresponding displacements of driven magnet 54 that result in acceptable ranges of volumetric blood throughput and heart rate.

This initial estimate of the forced motion of X/Xmax{t} results in changes in the pressure supplied by the combined diseased left ventricle plus L-VAD 74. The result is that the pressure and volume traces of the diseased heart shown in FIGS. 14 and 15 are modified, because the dynamic response of the native heart system and L-VAD system affect each other. (In simple terms, the motion of the one-way valve 70 from the aortic valve to the aortic arch sucks additional blood per heart beat from that accomplished by the diseased native ventricle alone, thus increasing ejected blood volume per beat, so that the whole system would tend to operate at lower heart rates).

The initial estimate of the shape of X/Xmax{t} results in a required forcing function $F_{vad}\{t\}$ that must be provided by driving magnet 40 to the hydraulic fluid and from there to the blood, and this corresponds to the distribution of voltage and current over time that the coils must provide to the driving magnet 40. The forcing function on driving magnet 40 is computed using the dynamic model described above in equation (7). This forcing function of the optimized design is compared with the 30–36 N maximum force estimated in the discussion of FIGS. 1–4, above. The electrical power (V{t} and i{t}) required to provide this force (FIG. 17, line 180) is computed using dynamic models of the transmission of power from the coils to the magnet, or measured experimentally, or with a similar technique, reflecting equation (8). The shape of Xmax{t} versus time is iteratively manipulated until the electrical power required is minimized.

In alternative embodiments of the power optimization method this minimization can be done numerically or experimentally, or by neural networks to handle the volume of data and computations required. The optimization of the transmission of electromagnetic power can be done for at least three different cases, depending on the type of controller 64: (a) the coils are supplied with constant voltage and power changes are obtained with changes in the electrical current; (b) The coils are supplied with constant current and power changes are obtained with changes in the voltage; and (c) the controller can vary both the current and voltage applied to each coil as a function of time.

It is expected that for a given initial diseased heart condition (for example, a heart rate of 100 beats per minute and ejected volume from the unaided left ventricle 50 cc) the power optimization process will result in several combinations of modified heart rates and ejected volumes (from the combined left ventricle and L-VAD) with slightly different power requirements. For example, three potential L-VAD solutions, each with a different shape of X/Xmax in FIGS. 16 and 17 to the above diseased-heart condition, may be:

(a) 80 beats per minute, 80 cc per beat, 7.0 Joules per beat (560 Joules/minute);
(b) 130 beats per minute, 60 cc per beat, 3.0 Joules per beat (465 Joules/min);
(c) 60 beats per minute, 90 cc per beat, 8.0 Joules per beat (480 Joules/min).

In the last step of FIG. 30, for most practical applications a cardiologist would choose to store in controller 64 either solution (a) or solution (c) rather than the lower-energy solution (b). These "optimal" solutions are obtained in an "external optimization process" shown in FIG. 28 for a wide range of diseased heart conditions and stored in controller 64. The combined output of the diseased native heart and the new VAD/TAH is optimized both for the individual diseased native heart of the patient and for the power required to drive the artificial device. The output of the power optimization method is the electrical power, and combinations of voltage and current, that must be applied by the controller to the coils.

In alternative embodiments this power optimization method can be carried out mathematically (equations (7) and (8) for the chosen system), or experimentally (with patient and VAD) in clinical trials for groups of patients, or individuals patients. In either case these optimization processes would benefit by the use of neural networks.

Figure 31:
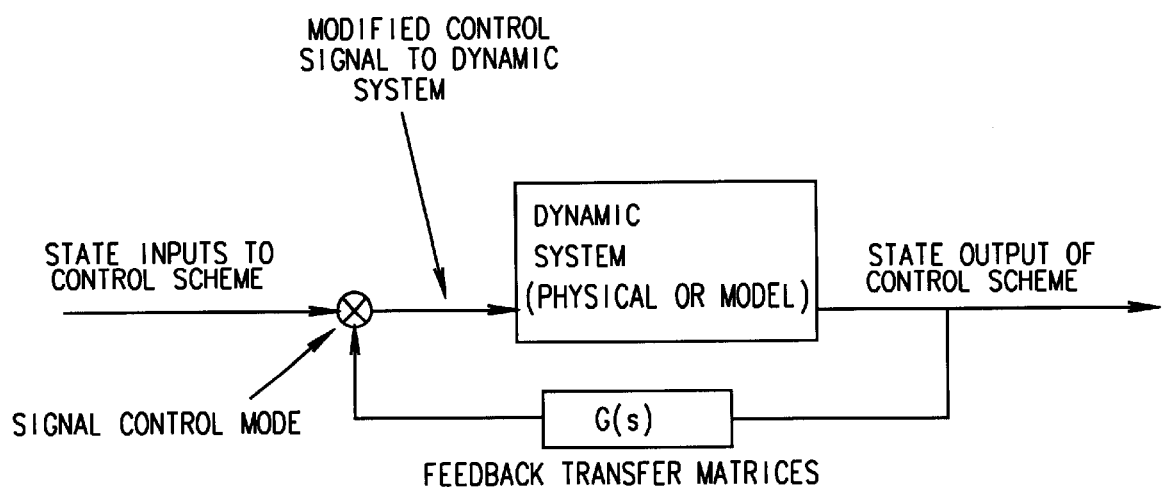
FIG. 31 is a flow chart schematically illustrating the multi-input, multi-output control system for performing the new process, and the controller optimization process.

The VAD installed in the patient must be able to adapt to dynamic changes from one condition to the other, as the patient with the VAD implanted in normal operative condition goes through normal daily activities requiring changes in heart rates and ejected blood volumes. The optimal design of the multi-input multi-output dynamic system of the patient is illustrated in FIG. 31. In one alternative embodiment of the control optimization method the physical dynamic system in FIG. 31 is the patient with the VAD installed, or in other words the control optimization method is experimental and is done clinically. In another alternative embodiment the control optimization method is done with the dynamic model of the physical prototype, reflected in expressions of "process equations" (7) and (8).

Examples of the dynamic system shown in FIG. 31 are dynamic models such as those shown in FIGS. 28 and 29, and incorporate the results of the power optimization method of FIG. 30 (that defines the steady-state, non-dynamically changing conditions of the system). In control-system terminology this is a multivariate control scheme (as opposed to more usual control schemes for simpler linear mechanical systems). For purposes of this document, "multivariate" means that the output state of the dynamic system is characterized by several input variables and several output variables, illustrated by the incoming and outgoing arrows on the left and right side of FIG. 31.

Examples of these output-state variables are the ECG trace, the blood volumes ejected from the ventricles, the flow rates through points such as M1, M2, M3 and M5, the blood pressures or hydraulic-fluid pressures at various points in the flow system, other similar quantities, rates of change of these variables with time, or combinations thereof. The state of these variables is measured by various pressure, velocity, position, etc., transducers. Information about the output state variables is fed back to the control node (x in circle) via the feedback transfer matrices G(s). The purpose of the control optimization method is:

(a) to find the optimum output variables for the control scheme;

(b) to find the types and values of these feedback transfer matrices G(s), which feed back signals to the control node; and (c) to find the optimum input state variables for the control scheme.

This optimization method is a multivariate input-output control method with several input-output state variables. The input state can be defined with variables such as beats per minute, the phase φ of the distance from point Q to point 154 in FIG. 17 (in units of degrees or in units of time), the value of X/Xmax, the shape of X/Xmax, several other similar quantities, or their rates of change with time, and combinations thereof. In general, these input-state control variables would be different from any similar quantities that were computed in the power optimization process. This does not preclude using the quantities from the power optimization process, but this may lead to system instabilities during transients.

Thus the inputs to the dynamic system are manipulated by functions of the outputs of the dynamic system (which can be the physical patient and VAD, or the dynamic model developed above) as affected by the feedback transfer matrices G(s). The modified inputs are fed into the dynamic system and affect its output state. This optimization of the control method can be done analytically, experimentally, or with various heuristic methods. Essentially these control methods ensure that corrections to the dynamic system to accommodate transient operations do not become unstable.

Simplified versions of this control sequence can be analyzed with linear control theory. However it is more likely that development of the control method will require well established analytic and experimental techniques of non-linear, discrete or continuous systems control, as several of the elements of the dynamic system (e.g. in FIG. 29) are non-linear.

Suitable analytic optimal control techniques have been published in the open literature (Brogan, 1990; Glad and Ljung, 2000; Fradkov et al., 1999; Schroder, 2000). However, it is envisioned that in alternative embodiments neural networks, adaptive control techniques, and observer-based methodologies will be suitable alternative embodiments of the new control optimization method. The final step in the control optimization sequence is to store the optimized feedback transfer matrices G(s), and associated control scheme, into controller 64.

Figures 32, 33:
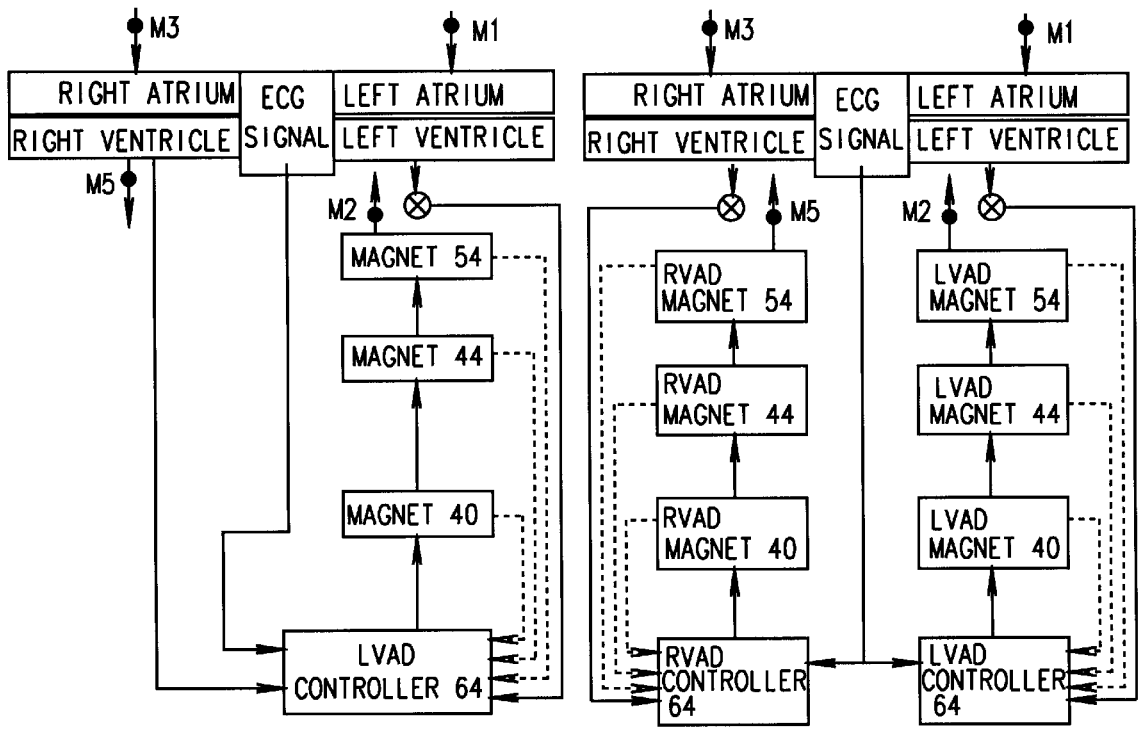
FIG. 32 is a flow chart schematically illustrating application of the new process in a system including the new VAD in an L-VAD arrangement.
FIG. 33 is a flow chart schematically illustrating application of the new process in a system including the new VAD in a BI-VAD arrangement.
Figure 34:
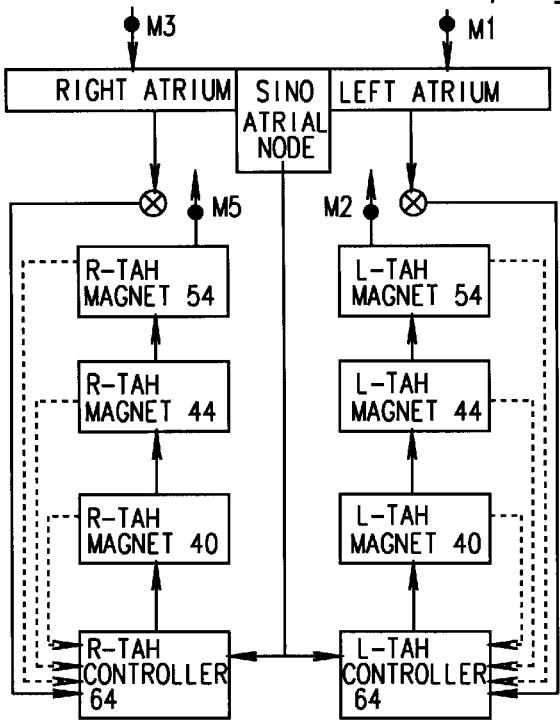
FIG. 34 is a flow chart schematically illustrating application of the new process in an alternative system including the new total artificial heart (TAH).

An additional way to illustrate the flow of information flow in the new device during normal operation is shown in the flow charts of FIGS. 32, 33 and 34, all of which include points M1, M2, M3 and M5 that are also in FIGS. 28 and 29. FIG. 32 shows the application to an L-VAD. The figure shows at the top the native heart as right and left sides, atria and ventricles, and in the center there is an illustration of the ECG signal, which feeds information to the controller. In this case, shown in FIG. 32, the information would be the ECG trace, or heart rate and phase entering the L-VAD controller. (Alternative embodiments may include measures of volumes and pressures in atria and/or ventricles). The left ventricle provides some output that goes into the control junction, shown by an X in a circle, which is also fed into the controller. The controller, using information provided by the power optimization method and control optimization method that were shown and discussed with reference to FIGS. 30 and 31, provides electric power, V{t} and i{t} to the coils, that dictates the movement of driving magnet 40. Driving magnet 40 in turn dictates the movement of driven magnet 44, and that in turn dictates the movement of valve-seat magnet 54, which affects the output of the left ventricle point M2). A similar arrangement could be drawn for the R-VAD, but it is exactly symmetrical to the one shown here so this is not drawn or described further.

The flow chart of FIG. 33 illustrates the application of the new optimization process to a bi-ventricular assist device (BI-VAD, described above). The flow chart is split into two parts, for the L-VAD and the R-VAD, right and left respectively. The components themselves and the logic flow paths are similar to those shown in FIG. 32, and thus are not discussed further herein.

FIG. 34 shows the application of the new optimization process to the total artificial heart (TAH) embodiment, in which the left and right ventricles are removed, but signals are still received from the sinoatrial node. These signals are provided to the L-TAH and R-TAH controllers 64. In response, the controllers drive magnets 40, 44 and 54, and finally these magnets provide the overall volumetric throughput for the cardiac system, corresponding to points M2 and M5 in FIGS. 30 and 31, as previously discussed.

These mathematical and engineering techniques will be augmented by clinical trials on groups of patients, and standard-sized or unique VAD devices sized for individual patients devices may be optimized to the individual patients. As the condition of the patient changes with time, the control variables and control scheme stored on controller 64 will need to be updated to the new condition of the patient. The power and control optimization sequences are identical to the sequences described above. The new data for controller 64 can be transmitted to the controller inside the patient's body using established infra-red data transmission techniques, or other similar techniques.

Several alternative embodiments to the described systems and methods are also conceived. For example, one alternative embodiment entails the use of neural networks, or comparable technology, to optimize the displacements shown in FIG. 28 (X/Xmax and their shape), with the ejected blood volume. For example, with reference to FIG. 29, dynamic measurement of volume ejected and phase may be eliminated, because volume and phase can be correlated (with neural networks) with the motion of two or more proximity sensors, as shown in FIG. 27.

Alternative embodiment of the above-described methods are conceived in which the optimization processes for FIGS. 30 and 31 is not done mathematically, but it largely depends on clinical trials with extensive use of neural networks to expedite the computation process.

Another enhancement of the new system is that the controller can detect the presence of certain arrhythmias, such as ventricular tachycardia, for example. In this event, the electromagnetic pump coils would be de-energized and no current would be supplied to such coils, as it would be undesirable for the VAD to be activated. As a "fail-safe", if the VAD was in fact de-energized, in such a case, the one-way valve 70 inside of valve-seat magnet 54 would respond to the pressure gradient of the blood flowing past it, and would open and close via the forces applied to it by the flowing blood.

In view of the foregoing, it will be seen that the several objects of the invention are achieved and other advantages are attained. Although the foregoing includes a description of the best mode contemplated for carrying out he invention, various modifications are conceivable.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. A method of optimizing a mechanical cardiac pumping device wherein unsteady fluid mechanics are used to optimize the forcing function imposed by the mechanical cardiac pumping device such that the power required by the mechanical cardiac pumping device is the minimum power required to complement the cardiac output of the diseased native heart, said method comprising the steps of:
   a. modeling the dynamic response of the diseased native heart and of the mechanical cardiac pumping device with experimental data;
   b. using the instantaneous non-linear mass, [M], damping, [C], and stiffness, [K] matrices of the dynamic model, and corresponding elemental displacements $\{x\}$ and its derivatives $\{\ddot{x}\}$ and $\{\dot{x}\}$, as inputs into an equation which sums these matrices to calculate the forcing function, $F\{t\}$, of the dynamic system;
   c. calculating the forcing function of the diseased native heart, $F_{nh}\{t\}$;
   d. calculating the required forcing function of the mechanical cardiac pumping device, $F_{vad}\{t\}$;
   e. inputing the value of $F_{vad}\{t\}$ from step d, above, into a controller; and
   f. connecting operatively the controller to a mechanical cardiac pumping device, such that the controller is able to direct to the mechanical cardiac pumping device the minimum power required to achieve $F_{vad}\{t\}$.

2. A method of optimizing a mechanical cardiac pumping device wherein unsteady fluid mechanics are used to optimize the forcing function imposed by the mechanical cardiac pumping device such that the power required by the mechanical cardiac pumping device is the minimum power required to complement the cardiac output of the diseased native heart, said method comprising the steps of:
   a. modeling the dynamic response of the diseased native heart and of the mechanical cardiac pumping device with experimental data;
   b. using the instantaneous non-linear mass, [M], damping, [C], and stiffness, [K] matrices of the dynamic model, and corresponding elemental displacements $\{x\}$ and its derivatives $\{\ddot{x}\}$ and $\{\dot{x}\}$, as inputs into an equation of the form:

$$[M]\{\ddot{x}\}+[C]\{\dot{x}\}+[K]\{x\}=F\{t\}$$

to calculate the forcing function, $F\{t\}$, of the dynamic system;
   c. calculating the forcing function of the diseased native heart, $F_{nh}\{t\}$;
   d. calculating the required forcing function of the mechanical cardiac pumping device, $F_{vad}\{t\}$, using an equation of the form:

$$F\{t\}=F_{nh}\{t\}+F_{vad}\{t\}$$

e. inputing the value of $F_{vad}\{t\}$ from step d, above, into a controller; and
   f. connecting operatively the controller to a mechanical cardiac pumping device, such that the controller is able to direct to the mechanical cardiac pumping device the optimal power required to achieve $F_{vad}\{t\}$.

3. A method of optimizing a mechanical cardiac pumping device wherein unsteady fluid mechanics are used to optimize the forcing function imposed by the mechanical cardiac pumping device such that the power required by the mechanical cardiac pumping device is the minimum power required to complement the cardiac output of the diseased native heart, said method comprising the steps of:
   a. modeling the dynamic response of the diseased native heart and of the mechanical cardiac pumping device with experimental data;
   b. using the instantaneous non-linear mass, [M], damping, [C], and stiffness, [K] matrices of the dynamic model, and corresponding elemental displacements $\{x\}$ and its derivatives $\{\ddot{x}\}$ and $\{\dot{x}\}$, as inputs into an equation of the form:

$$[M]\{\ddot{x}\}+[C]\{\dot{x}\}+[K]\{x\}=F\{t\}$$

to calculate the forcing function, $F\{t\}$, of the dynamic system;
   c. calculating the forcing function of the diseased native heart, $F_{nh}\{t\}$;

d. calculating the required forcing function of the mechanical cardiac pumping device, $F_{vad}\{t\}$, using an equation of the form:

$$F\{t\}=F_{nh}\{t\}+F_{vad}\{t\}$$

e. balancing the instantaneous power at any time t utilized by the mechanical cardiac pumping device with an equation of the form:

$$W(t)=F_{vad}\{t\}\cdot\{\dot{x}\}+\text{losses}=V\{t\}\cdot i\{t\}$$

f. inputing the value W(t) from step e, above, into a controller; and g. connecting operatively the controller to a mechanical cardiac pumping device, such that the controller is able to direct to the mechanical cardiac pumping device the optimal power required to achieve $F_{vad}\{t\}$.

* * * * *

UNITED STATES PATENT AND TRADEMARK OFFICE
CERTIFICATE OF CORRECTION

PATENT NO. : 6,632,169 B2
DATED : October 14, 2003
INVENTOR(S) : Korakianitis, Theodosios It is certified that error appears in the above-identified patent and that said Letters Patent is hereby corrected as shown below:

<u>Title page,</u>
Item [75], Inventors, please replace "Theodosios Korakianitis, St. Louis, MO (US); Lonn Grandia, Brussels, IL (US)" with -- Theodosios Korakianitis --.

Signed and Sealed this

Twentieth Day of July, 2004

JON W. DUDAS
*Acting Director of the United States Patent and Trademark Office*